US012700100B2

(12) United States Patent
Voronenko et al.

(10) Patent No.:  US 12,700,100 B2
(45) Date of Patent:      Aug. 4, 2026

(54) METHODS FOR AUTOMATIC TARGET IDENTIFICATION, TRACKING, AND SAFETY EVALUATION FOR RADIOTHERAPY

(71) Applicant: RefleXion Medical, Inc., Hayward, CA (US)

(72) Inventors: Yevgen Voronenko, Sunnyvale, CA (US); Maksat Haytmyradov, Hayward, CA (US); Peter Demetri Olcott, Los Gatos, CA (US); Lingxiong Shao, Saratoga, CA (US); Manoj V. Narayanan, Mentor, OH (US)

(73) Assignee: RefleXion Medical, Inc., Hayward, CA (US)

( * ) Notice: Subject to any disclaimer, the term of this patent is extended or adjusted under 35 U.S.C. 154(b) by 225 days.

(21) Appl. No.: 18/456,396

(22) Filed: Aug. 25, 2023

(65) Prior Publication Data

US 2024/0104767 A1     Mar. 28, 2024

Related U.S. Application Data

(63) Continuation of application No. PCT/US2022/017375, filed on Feb. 22, 2022.
(Continued)

(51) Int. Cl.
*G06T 7/11* (2017.01)
*A61N 5/10* (2006.01)
(Continued)

(52) U.S. Cl.
CPC ............... *G06T 7/11* (2017.01); *A61N 5/103* (2013.01); *A61N 5/1031* (2013.01);
(Continued)

(58) Field of Classification Search
CPC .... A61N 5/1031; A61N 5/1039; A61N 5/103; A61N 5/1067; A61N 5/1037;
(Continued)

(56) References Cited

U.S. PATENT DOCUMENTS

| | | | |
|---|---|---|---|
| 3,794,840 A | 2/1974 | Scott | |
| 3,906,233 A | 9/1975 | Vogel | |

(Continued)

FOREIGN PATENT DOCUMENTS

| | | |
|---|---|---|
| CA | 1121072 A | 3/1982 |
| CN | 1681436 A | 10/2005 |

(Continued)

OTHER PUBLICATIONS

Bangert, M. et al. (2016). "Accelerated iterative beam angle selection in IMRT," Medical Physics 43.3:1073-1082.
(Continued)

*Primary Examiner* — John Villecco
(74) *Attorney, Agent, or Firm* — Cooley LLP

(57) ABSTRACT

Disclosed herein are methods and systems for identifying the location of a target region using a tumor identification (ID) profile. A tumor ID profile includes identification parameters that characterize the target region. The tumor ID profile may be used to facilitate the identification of multiple target regions and to evaluate whether it is safe to deliver radiation to the target regions at their updated locations. Also disclosed herein are methods for analyzing a dose distribution to a target region by generating a bounded dose volume histogram (bDVH) based on gamma criteria comprising a distance-to-agreement (DTA) criterion and a dose difference (DD) criterion. In one variation, a gamma-derived bDVH is used in a method for selecting gamma criteria values for evaluating a radiotherapy treatment plan.

29 Claims, 26 Drawing Sheets

Related U.S. Application Data

(60) Provisional application No. 63/246,212, filed on Sep. 20, 2021, provisional application No. 63/221,859, filed on Jul. 14, 2021, provisional application No. 63/154,295, filed on Feb. 26, 2021.

(51) Int. Cl.

| | | |
|---|---|---|
| *G06T 7/00* | (2017.01) | |
| *G06T 7/12* | (2017.01) | |
| *G06T 7/70* | (2017.01) | |
| *G06T 7/73* | (2017.01) | |

(52) U.S. Cl.
CPC .......... *A61N 5/1039* (2013.01); *G06T 7/0012* (2013.01); *G06T 7/12* (2017.01); *G06T 7/70* (2017.01); *G06T 7/73* (2017.01); *A61N 2005/1052* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/20076* (2013.01); *G06T 2207/30096* (2013.01)

(58) Field of Classification Search
CPC .......... A61N 5/1071; A61N 2005/1052; A61N 5/1064; G06T 2207/30096; G06T 7/0012; G06T 7/12; G06T 2207/10081; G06T 2207/10104; G06T 7/70; G06V 10/25; G06V 2201/103; G06V 20/695
See application file for complete search history.

(56) References Cited

U.S. PATENT DOCUMENTS

| | | | |
|---|---|---|---|
| 4,389,569 A | 6/1983 | Hattori et al. | |
| 4,503,331 A | 3/1985 | Kovacs, Jr. et al. | |
| 4,529,882 A | 7/1985 | Lee | |
| 4,563,582 A | 1/1986 | Mullani | |
| 4,575,868 A | 3/1986 | Ueda et al. | |
| 4,642,464 A | 2/1987 | Mullani | |
| 4,647,779 A | 3/1987 | Wong | |
| 4,677,299 A | 6/1987 | Wong | |
| 4,868,844 A | 9/1989 | Nunan | |
| 5,015,851 A | 5/1991 | Singh et al. | |
| 5,075,554 A | 12/1991 | Yunker et al. | |
| 5,206,512 A | 4/1993 | Iwao | |
| 5,207,223 A | 5/1993 | Adler | |
| 5,317,616 A | 5/1994 | Swerdloff et al. | |
| 5,329,567 A | 7/1994 | Ikebe | |
| 5,351,280 A | 9/1994 | Swerdloff et al. | |
| 5,390,225 A | 2/1995 | Hawman | |
| 5,394,452 A | 2/1995 | Swerdloff et al. | |
| 5,396,534 A | 3/1995 | Thomas | |
| 5,418,827 A | 5/1995 | Deasy et al. | |
| 5,442,675 A | 8/1995 | Swerdloff et al. | |
| 5,548,627 A | 8/1996 | Swerdloff et al. | |
| 5,647,663 A | 7/1997 | Holmes | |
| 5,661,773 A | 8/1997 | Swerdloff et al. | |
| 5,724,400 A | 3/1998 | Swerdloff et al. | |
| 5,751,781 A | 5/1998 | Brown et al. | |
| 5,813,985 A | 9/1998 | Carroll | |
| 5,818,902 A | 10/1998 | Yu | |
| 5,851,182 A | 12/1998 | Sahadevan | |
| 5,937,028 A | 8/1999 | Tybinkowski et al. | |
| 6,180,943 B1 | 1/2001 | Lange | |
| 6,184,530 B1 | 2/2001 | Hines et al. | |
| 6,188,748 B1 | 2/2001 | Pastyr et al. | |
| 6,239,438 B1 | 5/2001 | Schubert | |
| 6,260,005 B1 | 7/2001 | Yang et al. | |
| 6,281,505 B1 | 8/2001 | Hines et al. | |
| 6,385,288 B1 | 5/2002 | Kanematsu | |
| 6,449,331 B1 | 9/2002 | Nutt et al. | |
| 6,449,340 B1 | 9/2002 | Tybinkowski et al. | |
| 6,455,856 B1 | 9/2002 | Gagnon | |
| 6,473,634 B1 | 10/2002 | Barni | |
| 6,504,899 B2 | 1/2003 | Pugachev et al. | |
| 6,552,693 B1 | 4/2003 | Leisten | |
| 6,560,311 B1 | 5/2003 | Shepard et al. | |
| 6,618,467 B1 | 9/2003 | Ruchala et al. | |
| 6,661,866 B1 | 12/2003 | Limkeman et al. | |
| 6,696,694 B2 | 2/2004 | Pastyr et al. | |
| 6,700,949 B2 | 3/2004 | Susami et al. | |
| 6,714,620 B2 | 3/2004 | Caflisch et al. | |
| 6,730,924 B1 | 5/2004 | Pastyr et al. | |
| 6,735,277 B2 | 5/2004 | McNutt et al. | |
| 6,794,653 B2 | 9/2004 | Wainer et al. | |
| 6,810,103 B1 | 10/2004 | Tybinkowski et al. | |
| 6,831,961 B1 | 12/2004 | Tybinkowski et al. | |
| 6,865,254 B2 | 3/2005 | Näfstadius | |
| 6,888,919 B2 | 5/2005 | Graf | |
| 6,914,959 B2 | 7/2005 | Bailey et al. | |
| 6,934,363 B2 | 8/2005 | Seufert | |
| 6,965,661 B2 | 11/2005 | Kojima et al. | |
| 6,976,784 B2 | 12/2005 | Kojima et al. | |
| 6,990,175 B2 | 1/2006 | Nakashima et al. | |
| 7,020,233 B1 | 3/2006 | Tybinkowski et al. | |
| 7,026,622 B2 | 4/2006 | Kojima et al. | |
| 7,110,808 B2 | 9/2006 | Adair | |
| 7,154,096 B2 | 12/2006 | Amano | |
| 7,167,542 B2 | 1/2007 | Juschka et al. | |
| 7,199,382 B2 | 4/2007 | Rigney et al. | |
| 7,227,925 B1 | 6/2007 | Mansfield et al. | |
| 7,242,750 B2 | 7/2007 | Tsujita | |
| 7,263,165 B2 | 8/2007 | Ghelmansarai | |
| 7,265,356 B2 | 9/2007 | Pelizzari et al. | |
| 7,280,633 B2 | 10/2007 | Cheng et al. | |
| 7,291,840 B2 | 11/2007 | Fritzler et al. | |
| 7,297,958 B2 | 11/2007 | Kojima et al. | |
| 7,298,821 B2 | 11/2007 | Ein-Gal | |
| 7,310,410 B2 | 12/2007 | Sohal et al. | |
| 7,386,099 B1 | 6/2008 | Kasper et al. | |
| 7,397,901 B1 | 7/2008 | Johnsen | |
| 7,397,902 B2 | 7/2008 | Seeber et al. | |
| 7,453,983 B2 | 11/2008 | Schildkraut et al. | |
| 7,453,984 B2 | 11/2008 | Chen et al. | |
| 7,469,035 B2 | 12/2008 | Keall et al. | |
| 7,555,103 B2 | 6/2009 | Johnsen | |
| 7,558,378 B2 | 7/2009 | Juschka et al. | |
| 7,560,698 B2 | 7/2009 | Rietzel | |
| 7,564,951 B2 | 7/2009 | Hasegawa et al. | |
| 7,596,209 B2 | 9/2009 | Perkins | |
| 7,627,082 B2 | 12/2009 | Kojima et al. | |
| 7,639,853 B2 | 12/2009 | Olivera et al. | |
| 7,656,999 B2 | 2/2010 | Hui et al. | |
| 7,715,606 B2 | 5/2010 | Jeung et al. | |
| 7,742,575 B2 | 6/2010 | Bourne | |
| 7,755,055 B2 | 7/2010 | Schilling | |
| 7,755,057 B2 | 7/2010 | Kim | |
| 7,778,691 B2 | 8/2010 | Zhang et al. | |
| 7,792,252 B2 | 9/2010 | Bohn | |
| 7,795,590 B2 | 9/2010 | Takahashi et al. | |
| 7,839,972 B2 | 11/2010 | Ruchala et al. | |
| 7,885,371 B2 | 2/2011 | Thibault et al. | |
| 7,949,095 B2 | 5/2011 | Ning et al. | |
| 7,957,507 B2 | 6/2011 | Cadman | |
| 7,965,819 B2 | 6/2011 | Nagata | |
| 7,983,380 B2 | 7/2011 | Guertin et al. | |
| 8,059,782 B2 | 11/2011 | Brown | |
| 8,063,376 B2 | 11/2011 | Maniawski et al. | |
| 8,093,568 B2 | 1/2012 | Mackie et al. | |
| 8,116,427 B2 | 2/2012 | Kojima et al. | |
| 8,139,713 B2 | 3/2012 | Janbakhsh | |
| 8,139,714 B1 | 3/2012 | Sahadevan | |
| 8,144,962 B2 | 3/2012 | Busch et al. | |
| 8,148,695 B2 | 4/2012 | Takahashi et al. | |
| 8,160,205 B2 | 4/2012 | Saracen et al. | |
| 8,232,535 B2 | 7/2012 | Olivera et al. | |
| 8,280,002 B2 | 10/2012 | Bani-Hashemi et al. | |
| 8,295,906 B2 | 10/2012 | Saunders et al. | |
| 8,304,738 B2 | 11/2012 | Gagnon et al. | |
| 8,335,296 B2 | 12/2012 | Dehler et al. | |
| 8,357,903 B2 | 1/2013 | Wang et al. | |

(56) References Cited

U.S. PATENT DOCUMENTS

| | | | |
|---|---|---|---|
| 8,384,049 B1 | 2/2013 | Broad | |
| 8,406,844 B2 | 3/2013 | Ruchala et al. | |
| 8,442,287 B2 | 5/2013 | Fordyce, II et al. | |
| 8,447,387 B2 | 5/2013 | Xu et al. | |
| 8,461,539 B2 | 6/2013 | Yamaya et al. | |
| 8,483,803 B2 | 7/2013 | Partain et al. | |
| 8,536,547 B2 | 9/2013 | Maurer, Jr. et al. | |
| 8,537,373 B2 | 9/2013 | Humphrey | |
| 8,581,196 B2 | 11/2013 | Yamaya et al. | |
| 8,588,367 B2 | 11/2013 | Busch et al. | |
| 8,606,349 B2 | 12/2013 | Rousso et al. | |
| 8,617,422 B2 | 12/2013 | Koschan et al. | |
| 8,641,592 B2 | 2/2014 | Yu | |
| 8,664,610 B2 | 3/2014 | Chuang | |
| 8,664,618 B2 | 3/2014 | Yao | |
| 8,712,012 B2 | 4/2014 | O'Connor | |
| 8,716,669 B2 | 5/2014 | Miyaoka et al. | |
| 8,745,789 B2 | 6/2014 | Saracen et al. | |
| 8,748,825 B2 | 6/2014 | Mazin | |
| 8,767,917 B2 | 7/2014 | Ruchala et al. | |
| 9,155,909 B2 | 10/2015 | Ishikawa | |
| 9,283,403 B2 | 3/2016 | Mazin et al. | |
| 9,649,509 B2 | 5/2017 | Mazin et al. | |
| 9,694,208 B2 | 7/2017 | Mazin et al. | |
| 9,731,148 B2 | 8/2017 | Olivera et al. | |
| 9,764,161 B2 | 9/2017 | Mazin et al. | |
| 9,895,554 B2* | 2/2018 | Nguyen | A61N 5/1049 |
| 10,143,857 B2 | 12/2018 | Mazin et al. | |
| 10,159,852 B2 | 12/2018 | Mazin et al. | |
| 10,166,405 B2* | 1/2019 | Nguyen | A61N 5/1064 |
| 10,456,600 B2* | 10/2019 | Owens | A61B 6/463 |
| 10,617,890 B2 | 4/2020 | Mazin et al. | |
| 10,688,320 B2* | 6/2020 | Voronenko | A61N 5/1045 |
| 10,695,583 B2 | 6/2020 | Mazin et al. | |
| 10,745,253 B2 | 8/2020 | Saracen et al. | |
| 10,918,884 B2 | 2/2021 | O'Connor et al. | |
| 10,946,215 B2* | 3/2021 | Sjolund | A61N 5/1038 |
| 10,960,230 B2* | 3/2021 | Nguyen | A61B 6/5217 |
| 11,033,757 B2* | 6/2021 | Voronenko | A61N 5/1036 |
| 11,141,607 B2 | 10/2021 | Mazin et al. | |
| 11,358,008 B2 | 6/2022 | Voronenko et al. | |
| 11,406,846 B2 | 8/2022 | Voronenko et al. | |
| 11,633,626 B2* | 4/2023 | Voronenko | A61N 5/1031 |
| | | | 378/65 |
| 11,801,398 B2 | 10/2023 | Voronenko et al. | |
| 12,002,216 B2* | 6/2024 | Albrecht | G06T 7/50 |
| 12,115,386 B2* | 10/2024 | Voronenko | A61N 5/1039 |
| 12,214,218 B2* | 2/2025 | Kolesnick | A61K 41/0038 |
| 12,233,286 B2 | 2/2025 | Voronenko et al. | |
| 12,303,718 B2* | 5/2025 | Owens | A61B 6/032 |
| 2002/0051513 A1 | 5/2002 | Pugachev et al. | |
| 2002/0163994 A1 | 11/2002 | Jones | |
| 2002/0191734 A1 | 12/2002 | Kojima et al. | |
| 2002/0193685 A1 | 12/2002 | Mate et al. | |
| 2003/0036700 A1 | 2/2003 | Weinberg | |
| 2003/0128801 A1 | 7/2003 | Eisenberg et al. | |
| 2003/0219098 A1 | 11/2003 | McNutt et al. | |
| 2003/0235531 A1 | 12/2003 | Adair | |
| 2004/0024300 A1 | 2/2004 | Graf | |
| 2004/0030246 A1 | 2/2004 | Townsend et al. | |
| 2004/0057557 A1 | 3/2004 | Nafstadius | |
| 2004/0158416 A1 | 8/2004 | Slates | |
| 2005/0213705 A1 | 9/2005 | Hoffman | |
| 2005/0228255 A1 | 10/2005 | Saracen et al. | |
| 2006/0072699 A1 | 4/2006 | Mackie et al. | |
| 2006/0113482 A1 | 6/2006 | Pelizzari et al. | |
| 2006/0173294 A1 | 8/2006 | Ein-Gal | |
| 2006/0182326 A1 | 8/2006 | Schildkraut et al. | |
| 2006/0193435 A1 | 8/2006 | Hara et al. | |
| 2006/0237652 A1 | 10/2006 | Kimchy et al. | |
| 2007/0014391 A1 | 1/2007 | Mostafavi et al. | |
| 2007/0025513 A1 | 2/2007 | Ghelmansarai | |
| 2007/0041500 A1 | 2/2007 | Olivera et al. | |
| 2007/0043289 A1 | 2/2007 | Adair | |
| 2007/0053491 A1 | 3/2007 | Schildkraut et al. | |
| 2007/0055144 A1 | 3/2007 | Neustadter et al. | |
| 2007/0075273 A1 | 4/2007 | Birgy et al. | |
| 2007/0085012 A1 | 4/2007 | Thompson | |
| 2007/0211857 A1 | 9/2007 | Urano et al. | |
| 2007/0221869 A1 | 9/2007 | Song | |
| 2007/0242801 A1 | 10/2007 | Mackie et al. | |
| 2007/0265230 A1 | 11/2007 | Rousso et al. | |
| 2007/0265528 A1 | 11/2007 | Xu et al. | |
| 2008/0002811 A1 | 1/2008 | Allison | |
| 2008/0031404 A1 | 2/2008 | Khamene et al. | |
| 2008/0128631 A1 | 6/2008 | Suhami | |
| 2008/0130825 A1 | 6/2008 | Fu et al. | |
| 2008/0152085 A1 | 6/2008 | Saracen et al. | |
| 2008/0156993 A1 | 7/2008 | Weinberg et al. | |
| 2008/0177179 A1 | 7/2008 | Stubbs et al. | |
| 2008/0205588 A1 | 8/2008 | Kim | |
| 2008/0230705 A1 | 9/2008 | Rousso et al. | |
| 2008/0253516 A1 | 10/2008 | Hui et al. | |
| 2008/0273659 A1 | 11/2008 | Guertin et al. | |
| 2008/0298536 A1 | 12/2008 | Ein-Gal | |
| 2009/0003655 A1 | 1/2009 | Wollenweber | |
| 2009/0086909 A1 | 4/2009 | Hui et al. | |
| 2009/0116616 A1 | 5/2009 | Lu et al. | |
| 2009/0169082 A1 | 7/2009 | Mizuta et al. | |
| 2009/0256078 A1 | 10/2009 | Mazin | |
| 2009/0309046 A1 | 12/2009 | Balakin | |
| 2010/0040197 A1 | 2/2010 | Maniawski et al. | |
| 2010/0054412 A1 | 3/2010 | Brinks et al. | |
| 2010/0067660 A1 | 3/2010 | Maurer, Jr. et al. | |
| 2010/0069742 A1 | 3/2010 | Partain et al. | |
| 2010/0074400 A1 | 3/2010 | Sendai | |
| 2010/0074408 A1 | 3/2010 | Bert et al. | |
| 2010/0074498 A1 | 3/2010 | Breeding et al. | |
| 2010/0166274 A1 | 7/2010 | Busch et al. | |
| 2010/0176309 A1 | 7/2010 | Mackie et al. | |
| 2010/0198063 A1 | 8/2010 | Huber et al. | |
| 2010/0220832 A1 | 9/2010 | Ning et al. | |
| 2010/0237259 A1 | 9/2010 | Wang | |
| 2010/0258138 A1 | 10/2010 | Sorensen et al. | |
| 2011/0006212 A1 | 1/2011 | Shchory et al. | |
| 2011/0044429 A1 | 2/2011 | Takahashi et al. | |
| 2011/0073763 A1 | 3/2011 | Subbarao | |
| 2011/0092814 A1 | 4/2011 | Yamaya et al. | |
| 2011/0215248 A1 | 9/2011 | Lewellen et al. | |
| 2011/0249088 A1 | 10/2011 | Hannibal et al. | |
| 2011/0272600 A1 | 11/2011 | Bert et al. | |
| 2011/0297833 A1 | 12/2011 | Takayama | |
| 2011/0309252 A1 | 12/2011 | Moriyasu et al. | |
| 2011/0309255 A1 | 12/2011 | Bert et al. | |
| 2011/0313231 A1 | 12/2011 | Guertin et al. | |
| 2011/0313232 A1 | 12/2011 | Balakin | |
| 2012/0138804 A1 | 6/2012 | Miyaoka et al. | |
| 2012/0161014 A1 | 6/2012 | Yamaya et al. | |
| 2012/0174317 A1 | 7/2012 | Saracen et al. | |
| 2012/0230464 A1 | 9/2012 | Ling et al. | |
| 2012/0320055 A1 | 12/2012 | Pekar et al. | |
| 2013/0025055 A1 | 1/2013 | Saracen et al. | |
| 2013/0060134 A1 | 3/2013 | Eshima et al. | |
| 2013/0102830 A1 | 4/2013 | Otto | |
| 2013/0266116 A1 | 10/2013 | Abenaim et al. | |
| 2014/0105355 A1 | 4/2014 | Toimela et al. | |
| 2014/0107390 A1 | 4/2014 | Brown et al. | |
| 2014/0107460 A1* | 4/2014 | Nguyen | A61N 5/1049 |
| | | | 600/407 |
| 2014/0163368 A1 | 6/2014 | Rousso et al. | |
| 2014/0193336 A1 | 7/2014 | Rousso et al. | |
| 2014/0217294 A1 | 8/2014 | Rothfuss et al. | |
| 2014/0228613 A1* | 8/2014 | Mazin | G01T 1/2985 |
| | | | 600/1 |
| 2014/0239204 A1 | 8/2014 | Orton et al. | |
| 2014/0257096 A1 | 9/2014 | Prevrhal et al. | |
| 2014/0275962 A1* | 9/2014 | Foo | A61B 5/055 |
| | | | 600/411 |
| 2015/0055849 A1 | 2/2015 | Galavis et al. | |
| 2015/0087960 A1 | 3/2015 | Treffert | |
| 2015/0094519 A1* | 4/2015 | Kuusela | A61N 5/1071 |
| | | | 600/1 |
| 2015/0251017 A1 | 9/2015 | De Crevoisier et al. | |
| 2015/0355347 A1 | 12/2015 | Pratx | |

(56)                    References Cited

U.S. PATENT DOCUMENTS

| | | | |
|---|---|---|---|
| 2015/0367143 A1 | 12/2015 | Muraki et al. | |
| 2016/0296766 A1 | 10/2016 | El Fakhri et al. | |
| 2016/0331997 A1 | 11/2016 | Vilsmeier | |
| 2016/0361566 A1 | 12/2016 | Larkin et al. | |
| 2017/0014642 A1 | 1/2017 | An et al. | |
| 2017/0368372 A1 | 12/2017 | Mazin et al. | |
| 2018/0001109 A1 | 1/2018 | Mazin et al. | |
| 2018/0369611 A1* | 12/2018 | Owens | A61N 5/1067 |
| 2019/0001152 A1 | 1/2019 | O'Connor et al. | |
| 2019/0083815 A1 | 3/2019 | Mazin et al. | |
| 2019/0091487 A1 | 3/2019 | Pal et al. | |
| 2019/0255362 A1 | 8/2019 | Voronenko et al. | |
| 2019/0262630 A1* | 8/2019 | Voronenko | A61B 6/5205 |
| 2020/0016432 A1* | 1/2020 | Maolinbay | A61B 5/0036 |
| 2022/0096867 A1 | 3/2022 | Mazin et al. | |
| 2023/0067048 A1 | 3/2023 | Voronenko et al. | |
| 2023/0230253 A1* | 7/2023 | Albrecht | G06N 7/01 |
| | | | 382/131 |
| 2023/0256266 A1* | 8/2023 | Voronenko | A61N 5/107 |
| | | | 600/1 |
| 2023/0285777 A1* | 9/2023 | Bassalow | A61N 5/1067 |
| 2024/0082605 A1 | 3/2024 | Voronenko et al. | |
| 2024/0189624 A1* | 6/2024 | Olcott | G16H 20/40 |
| 2025/0121211 A1* | 4/2025 | Mazin | A61N 5/1067 |
| 2025/0262460 A1 | 8/2025 | Voronenko et al. | |

FOREIGN PATENT DOCUMENTS

| | | | |
|---|---|---|---|
| CN | 1960780 A | 5/2007 | |
| CN | 101013095 A | 8/2007 | |
| CN | 101247852 A | 8/2008 | |
| CN | 101305297 A | 11/2008 | |
| CN | 101970043 A | 2/2011 | |
| CN | 102068763 A | 5/2011 | |
| CN | 102160913 A | 8/2011 | |
| CN | 102553089 A | 7/2012 | |
| CN | 102641561 A | 8/2012 | |
| CN | 103006253 A | 4/2013 | |
| CN | 103126713 A | 6/2013 | |
| CN | 103517737 A | 1/2014 | |
| CN | 103845068 A | 6/2014 | |
| CN | 104866928 A | 8/2015 | |
| CN | 104994909 A | 10/2015 | |
| DE | 10 2008 053321 A1 | 5/2010 | |
| EP | 1 402 761 B1 | 8/2008 | |
| EP | 2 188 815 B1 | 5/2010 | |
| EP | 1 660 175 B1 | 2/2012 | |
| EP | 2 687 259 A1 | 1/2014 | |
| EP | 2 777 768 A1 | 9/2014 | |
| EP | 3 175 886 B1 | 6/2018 | |
| JP | 09-33658 A | 2/1997 | |
| JP | 9-189769 A2 | 7/1997 | |
| JP | 2000-105279 A | 4/2000 | |
| JP | 2001-340474 A | 12/2001 | |
| JP | 2002-522128 A | 7/2002 | |
| JP | 2003-534823 A | 11/2003 | |
| JP | 2004/073404 A | 3/2004 | |
| JP | 2004-513735 A | 5/2004 | |
| JP | 2006-007464 A | 1/2006 | |
| JP | 2006-145281 A | 6/2006 | |
| JP | 2007-502166 A | 2/2007 | |
| JP | 2007-507246 A | 3/2007 | |
| JP | 2007-083036 A | 4/2007 | |
| JP | 2008-173299 A | 7/2008 | |
| JP | 2009-005440 A | 1/2009 | |
| JP | 2009-502249 A | 1/2009 | |
| JP | 2009-544101 A | 12/2009 | |
| JP | 2010-517655 A | 5/2010 | |
| JP | 2011-514213 A | 5/2011 | |
| JP | 2011-528977 A | 12/2011 | |
| JP | 2012-035072 A | 2/2012 | |
| JP | 2014-023741 A | 2/2014 | |
| JP | 2016-168077 A | 9/2016 | |
| JP | 6210972 B2 | 10/2017 | |
| JP | 6571816 B2 | 9/2019 | |
| JP | 6796886 B2 | 12/2020 | |
| JP | 7274773 B2 | 5/2023 | |
| WO | WO-89/10090 A1 | 11/1989 | |
| WO | WO-94/28971 A2 | 12/1994 | |
| WO | WO-94/28971 A3 | 12/1994 | |
| WO | WO-00/015299 A1 | 3/2000 | |
| WO | WO-2004/017832 A2 | 3/2004 | |
| WO | WO-2004/017832 A3 | 3/2004 | |
| WO | WO-2005/018734 A2 | 3/2005 | |
| WO | WO-2005/018734 A3 | 3/2005 | |
| WO | WO-2005/018735 A2 | 3/2005 | |
| WO | WO-2005/018735 A3 | 3/2005 | |
| WO | WO-2005/110495 A1 | 11/2005 | |
| WO | WO-2007/045076 A1 | 4/2007 | |
| WO | WO-2007/124760 A1 | 11/2007 | |
| WO | WO-2008/019118 A2 | 2/2008 | |
| WO | WO-2008/024463 A2 | 2/2008 | |
| WO | WO-2008/024463 A3 | 2/2008 | |
| WO | WO-2009/111580 A2 | 9/2009 | |
| WO | WO-2009/111580 A3 | 9/2009 | |
| WO | WO-2009/114117 A2 | 9/2009 | |
| WO | WO-2010/015358 A1 | 2/2010 | |
| WO | WO-2010/018477 A2 | 2/2010 | |
| WO | WO-2010/018477 A3 | 2/2010 | |
| WO | WO-2010/110255 A1 | 9/2010 | |
| WO | WO-2012/135771 A1 | 10/2012 | |
| WO | WO-2013/093852 A1 | 6/2013 | |
| WO | WO-2015/168431 A1 | 11/2015 | |
| WO | WO-2016/061877 A1 | 4/2016 | |
| WO | WO-2016/064750 A1 | 4/2016 | |
| WO | WO-2017/048852 A1 | 3/2017 | |
| WO | WO-2017/156316 A1 | 9/2017 | |
| WO | WO-2018/093933 A1 | 5/2018 | |
| WO | WO-2018/222751 A1 | 12/2018 | |
| WO | WO-2019/060764 A1 | 3/2019 | |
| WO | WO-2020/144134 A1 | 7/2020 | |
| WO | WO-2021/011207 A1 | 1/2021 | |

OTHER PUBLICATIONS

Bao, Q. et al. (2010). "Estimation of the minimum detectable activity of preclinical PET imaging systems with an analytical method," Med. Phys. 37:6070-6083.

Chang, J.Y. et al. (2008). "Image-Guided Radiation Therapy for Non-Small Cell Lung Cancer," J. Thorac. Oncol. FEB 3(2):177-186.

Chen, X. et al. (2012). "Smoothing proximal gradient method for general structured sparse regression," The Annals of Applied Statistics 6:719-752.

Dieterich, S. et al. (2003). "Skin respiratory motion tracking for stereotactic radiosurgery using the CyberKnife," Elsevier Int'l Congress Series 1256:130-136.

Erdi, Y.E. (Feb. 2007). "The Use of PET for Radiotherapy," Current Medical Imaging Reviews 3(1):3-16.

Extended European Search Report mailed on Oct. 7, 2015, for European Application No. 12 763 280.0, filed on Mar. 30, 2012, 11 pages.

Extended European Search Report mailed on Nov. 21, 2018, for European Application No. 18 168 947.2, filed on Mar. 30, 2012, 8 pages.

Extended European Search Report mailed on Oct. 15, 2019, for European Application No. 17 764 132.1, filed on Mar. 9, 2017, 4 pages.

Extended European Search Report mailed on Oct. 15, 2021, for European Application No. 19 754 923.1, filed on Feb. 13, 2019, 11 pages.

Fan, Q. (Nov. 2012). "Emission Guided Radiation Therapy for Lung and Prostrate Cancers: A Feasibility Study on a Digital Patient," Med. Phys. 39(11):7140-7152.

Fan, Q. et al. (Aug. 2013). "Toward a Planning Scheme for Emission Guided Radiation Therapy (EGRT): FDG Based Tumor Tracking in a Metastatic Breast Cancer Patient," Med. Phys. 40(8):081708, 12 pages.

(56) References Cited

OTHER PUBLICATIONS

Final Office Action mailed on Aug. 2, 2018, for U.S. Appl. No. 15/684,710, filed Aug. 23, 2017, 8 pages.

Final Office Action mailed on Aug. 21, 2023, for U.S. Appl. No. 17/485,059, filed Sep. 24, 2021, 10 pages.

Fredriksson (2013). "Robust optimization of radiation therapy accounting for geometric uncertainty," KTH Engin. Sciences, pp. 8-14.

Gibbons, J.P. (2004). "Dose calculation and verification for tomotherapy," 2004 ACMP Meeting, Scottsdale, AZ., 71 total pages.

Handsfield, L.L. et al. (2014). "Phantomless patient-specific TomoTherapy QA via delivery performance monitoring and a secondary Monte Carlo dose calculation," Med. Phys. 41:101703-1-101703-9.

Internal Atomic Energy Agency (Oct. 2008). "The Role of PET/CT in Radiation Treatment Planning for Cancer Patient Treatment," located at https://www-pub.iaea.org/MTCD/Publications/PDF/te_1603_web.pdf, 40 total pages.

International Search Report mailed on Jul. 20, 2012, for PCT Patent Application No. PCT/US2012/31704, filed on Mar. 30, 2012, 2 pages.

International Search Report mailed on Jun. 27, 2017, for PCT Patent Application No. PCT/US2017/021647, filed on Mar. 9, 2017, 3 pages.

Japanese Office Action mailed Dec. 25, 2015, For Japanese Patent Application No. 2014-502881 filed Mar. 20, 2012, 14 pages (with English Translation).

Kapatoes, J.M. et al. (2001). "A feasible method for clinical delivery verification and dose reconstruction in tomotherapy," Med. Phys. 28:528-542.

Kapatoes, J. M. (2001). "On the accuracy and effectiveness of dose reconstruction for tomotherapy," Physics in Med. Biol. 46:943-966.

Keall, P.J. et al. (2001). "Motion adaptive x-ray therapy: a feasibility study," Physics in Med. Biol. 46:1-10.

Krouglicof, N. et al. (Nov. 2013). "Development of a Novel PCB-Based Voice Coil Actuator for Opto-Mechatronic Applications," presented at IEEE/RSJ International Conference on Intelligent Robots and Systems (IROS), Tokyo, Japan, Nov. 3-7, 2013, pp. 5834-5840.

Lee, S. et al. (2015). "Treatment plan comparison of Linac step and shoot, tomotherapy, RapidArc, and proton therapy for prostate cancer using dosimetrical and biological index," J. Korean Physical Society 67:7-16 (with tables 1-5), 28 total pages.

Lu, W. (2008). "Real-time motion-adaptive delivery (MAD) using binary MLC: I. Static beam (topotherapy) delivery," Phys. Med. Biol. 53:6491-6511.

Lu, W. (2009). "Real-time motion-adaptive-optimization (MAO) in tomotherapy," Phys. Med. Biol. 54:4373-4398.

Mackie, T.R. et al. (Nov-Dec. 1993). "Tomotherapy: A New Concept for the Delivery of Dynamic Conformal Radiotherapy," Med. Phys. 20(6):1709-1719.

Manikandan et al. (2013). "Role of step size and max dwell time in anatomy based inverse optimization for prostate implants," J. Med. Phys. 38:148-154.

Mazin, S.R. et al. (Dec. 2010). "Emission-Guided Radiation Therapy: Biologic Targeting and Adaptive Treatment," Journal of American College of Radiology 7(12):989-990.

Mcmahon, R. et al. (2008). "A real-time dynamic-MLC control algorithm for delivering IMRT to targets undergoing 2D rigid motion in the beam's eye view," Med. Phys. 35:3875-3888.

Non-Final Office Action mailed on Feb. 24, 2017, for U.S. Appl. No. 15/069,390, filed Mar. 14, 2016, 6 pages.

Non-Final Office Action mailed on Feb. 21, 2018, for U.S. Appl. No. 15/684,710, filed Aug. 23, 2017, 10 pages.

Non-Final Office Action mailed on Mar. 27, 2018, for U.S. Appl. No. 15/684,693, filed Aug. 23, 2017, 7 pages.

Non-Final Office Action mailed on Aug. 30, 2019, for U.S. Appl. No. 16/193,725, filed Nov. 16, 2018, 5 pages.

Non-Final Office Action mailed on Sep. 19, 2019, for U.S. Appl. No. 16/217,417, filed Dec. 12, 2018, 7 pages.

Non-Final Office Action mailed on Jun. 26, 2020, for U.S. Appl. No. 16/122,735, filed Sep. 5, 2018, 16 pages.

Non-Final Office Action mailed on Oct. 29, 2020, for U.S. Appl. No. 16/834,956, filed Mar. 30, 2020, 7 pages.

Non-Final Office Action mailed on Dec. 21, 2021, for U.S. Appl. No. 16/412,780, filed May 15, 2019, 15 pages.

Non-Final Office Action mailed on Mar. 3, 2022, for U.S. Appl. No. 16/274,962, filed Feb. 13, 2019, 12 pages.

Non-Final Office Action mailed on Jan. 27, 2023, for U.S. Appl. No. 17/485,059, filed Sep. 24, 2021, 11 pages.

Notice of Allowance mailed on May 18, 2017, for U.S. Appl. No. 15/069,390, filed Mar. 14, 2016, 5 pages.

Notice of Allowance mailed on Jul. 19, 2017, for U.S. Appl. No. 15/499,671, filed Apr. 27, 2017, 8 pages.

Notice of Allowance mailed on Oct. 3, 2018, for U.S. Appl. No. 15/684,693, filed Aug. 23, 2017, 5 pages.

Notice of Allowance mailed on Oct. 25, 2018, for U.S. Appl. No. 15/684,710, filed Aug. 23, 2017, 7 pages.

Notice of Allowance mailed on Mar. 13, 2020, for U.S. Appl. No. 16/217,417, filed Dec. 12, 2018, 6 pages.

Notice of Allowance mailed on Dec. 11, 2020, for U.S. Appl. No. 16/122,735, filed Sep. 5, 2018, 10 pages.

Notice of Allowance mailed on Jun. 21, 2021, for U.S. Appl. No. 16/834,956, filed Mar. 30, 2020, 7 pages.

Notice of Allowance mailed on Apr. 12, 2022, for U.S. Appl. No. 16/274,962, filed Feb. 13, 2019, 8 pages.

Notice of Allowance mailed on Jun. 8, 2022, for U.S. Appl. No. 16/412,780, filed May 15, 2019, 8 pages.

Notice of Allowance mailed on Apr. 4, 2023, for U.S. Appl. No. 17/831,105, filed Jun. 2, 2022, 9 pages.

Notice of Allowance mailed on Jul. 5, 2023, for U.S. Appl. No. 17/831,105, filed Jun. 2, 2022, 7 pages.

Olivera, G.H. et al. (2000). "Modifying a plan delivery without re-optimization to account for patient offset in tomotherapy," Proceedings of the $22^{nd}$ Annual EMBS International Conference, Jul. 23-28, 2000, Chicago, IL, pp. 441-444.

Papanikolaou, N. et al. (2010). "MU-Tomo: Independent dose validation software for helical tomo therapy," J. Cancer Sci. Ther. 2:145-152.

Prabhaker, R. et al. (2007, e-published Jan. 2008). "An Insight into PET-CT Based Radiotherapy Treatment Planning," Cancer Therapy (5):519-524.

Shalchian, B. et al. (2009). "Assessment of the Wavelet Transform in Reduction of Noise from Simulated PET Images," Journal of Nuclear Medicine Technology 37:223-228.

Shirvani, S.M. et al. (Jan. 2021). "Biology-guided radiotherapy: redefining the role of radiotherapy in metastatic cancer," Br. J. Radiol. 94:20200873, 10 total pages.

Tashima, H. et al. (Jul. 21, 2012). "A Single-Ring OpenPET Enabling PET Imaging During Radiotherapy," Phys. Med. Biol. 57(14):4705-4718.

The Partial Supplementary European Search Report, mailed on Jun. 25, 2015 for European Application No. 12763280.0, filed on Mar. 30, 2012, 6 pages.

Thorwarth, D. et al. (2010). "Physical radiotherapy treatment planning based on functional PET/CT data," Radiotherapy Oncology, pp. 317-324.

Varian Medical Systems (2004). "Dynamic Targeting™ Image-Guided Radiation Therapy-A Revolution in Cancer Care," Business Briefing: US Oncology Review , Abstract only, 2 pages.

Written Opinion of the International Searching Authority mailed on Jan. 17, 2018, for PCT Application No. PCT/US2017/061728, filed on Nov. 15, 2017, 7 pages.

Written Opinion of the International Searching Authority mailed on Jun. 14, 2019, for PCT Application No. PCT/US2019/017855, filed on Feb. 13, 2019, 10 pages.

Written Opinion of the International Searching Authority mailed on Aug. 24, 2022, for PCT Application No. PCT/US2022/017375, filed on Feb. 22, 2022, 11 pages.

Yamaya, T. et al. (Jan. 14, 2008). "A Proposal of an Open PET Geometry," Physics in Medicine and Biology 53:757-773.

Yan, D. et al. (1997). "Adaptive radiation therapy," Physics Med. Biol. 42:123-132.

(56) References Cited

OTHER PUBLICATIONS

U.S. Appl. No. 18/472,034, Corrected Notice of Allowability mailed Jan. 29, 2025, Inventor Voronenko, Yevgen et al., 4 pages.

U.S. Appl. No. 17/855,691, Corrected Notice of Allowability mailed Nov. 4, 2025, Inventor Voronenko, Yevgen et al., 3 pages.

U.S. Appl. No. 17/485,059, Final Office Action mailed Jul. 1, 2024, Inventor Mazin, Samuel et al., 10 pages.

U.S. Appl. No. 17/855,691, Final Office Action mailed May 14, 2025, Inventor Voronenko, Yevgen et al., 14 pages.

Gregoire, V. et al. (Jan. 2007). "PET-based treatment planning in radiotherapy: a new standard?" J. Nucl. Med. 48(Suppl 1):68S-77S.

PCT Application No. PCT/US2012/31704, International Search Report and Written Opinion mailed Jul. 20, 2012, Applicant RefleXion Medical, Inc., 12 pages.

PCT Application No. PCT/US2017/021647, International Search Report and Written Opinion mailed Jun. 27, 2017, Applicant RefleXion Medical, Inc., 8 pages.

PCT Application No. PCT/US2017/061728, International Search Report and Written Opinion mailed Jan. 17, 2018, Applicant RefleXion Medical, Inc., 9 pages.

PCT Application No. PCT/US2019/017855, International Search Report and Written Opinion mailed Jun. 14, 2019, Applicant RefleXion Medical, Inc., 14 pages.

PCT Application No. PCT/US2022/017375, International Search Report and Written Opinion mailed Aug. 24, 2022, Applicant RefleXion Medical, Inc., 18 pages.

U.S. Appl. No. 17/485,059, Non-Final Office Action mailed Dec. 13, 2023, Inventor Mazin, Samuel et al., 10 pages.

U.S. Appl. No. 18/472,034, Non-Final Office Action mailed Apr. 23, 2024, Inventor Voronenko, Yevgen et al., 7 pages.

U.S. Appl. No. 17/855,691, Non-Final Office Action mailed Sep. 23, 2024, Inventor Voronenko, Yevgen et al., 15 pages.

U.S. Appl. No. 16/193,725, Notice of Allowance mailed Jan. 21, 2020, Inventor Mazin, Samuel et al., 7 pages.

U.S. Appl. No. 18/472,034, Notice of Allowance mailed Oct. 23, 2024, Inventor Voronenko, Yevgen et al., 7 pages.

U.S. Appl. No. 17/855,691, Notice of Allowance mailed Oct. 15, 2025, Inventor Voronenko, Yevgen et al., 9 pages.

Staff, N.R.C. (1996). "Mathematics and Physics of Emerging Biomedical imaging," National Academies Press, Washington, D.C., 85 pages.

* cited by examiner

<u>300</u>

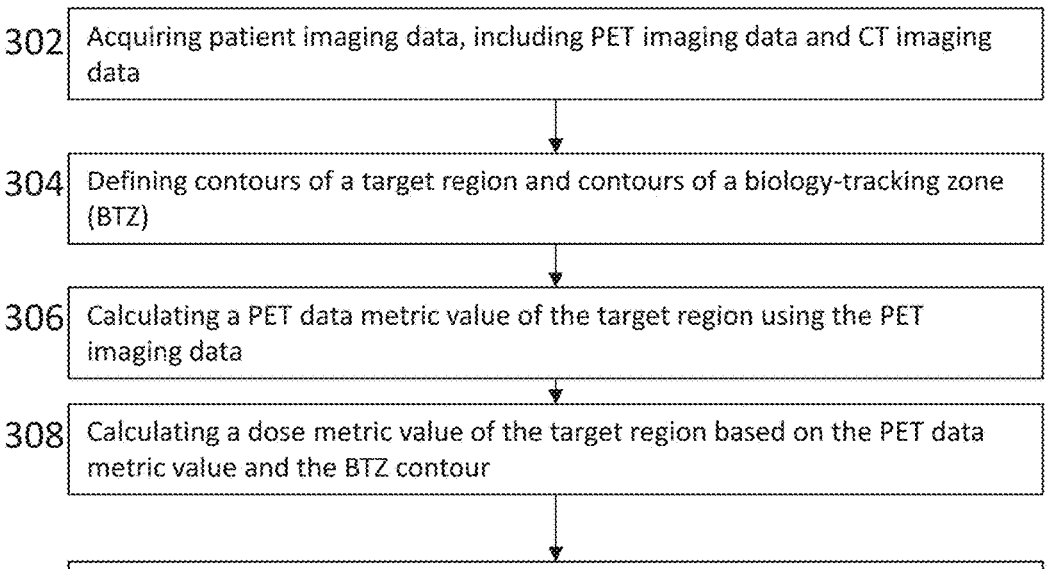

302 | Acquiring patient imaging data, including PET imaging data and CT imaging data 304 | Defining contours of a target region and contours of a biology-tracking zone (BTZ)

306 | Calculating a PET data metric value of the target region using the PET imaging data 308 | Calculating a dose metric value of the target region based on the PET data metric value and the BTZ contour 310 | Generating a tumor identification (ID) profile comprising identification parameters that comprise criteria that are based on the PET data metric value and the dose metric value

FIG. 3A

Tumor 1

NTS = 2
Mean SUV = 3
Tracer concentration = 4 KBq/ml

Local mean dose = 5 Gy
Local min dose = 3.5 Gy
Global mean dose = 1 Gy

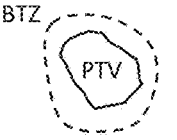

FIG. 3B

Tumor 2

NTS = 2.5
Mean SUV = 3
Tracer concentration = 5.5 KBq/ml

Local mean dose = 4.5 Gy
Local min dose = 3.5 Gy
Global mean dose = 0.5 Gy

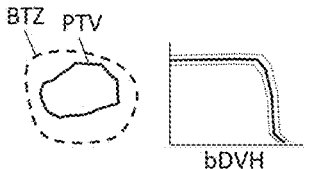

FIG. 3C

Tumor 3

NTS = 2.3
Mean SUV = 3
Tracer concentration = 6.2 KBq/ml

Local mean dose = 5 Gy
Local min dose = 4.5 Gy
Global mean dose = 1.5 Gy
Isodose 120% vol = 1.8 cc

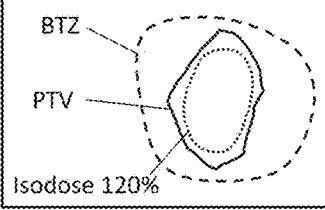

FIG. 3D

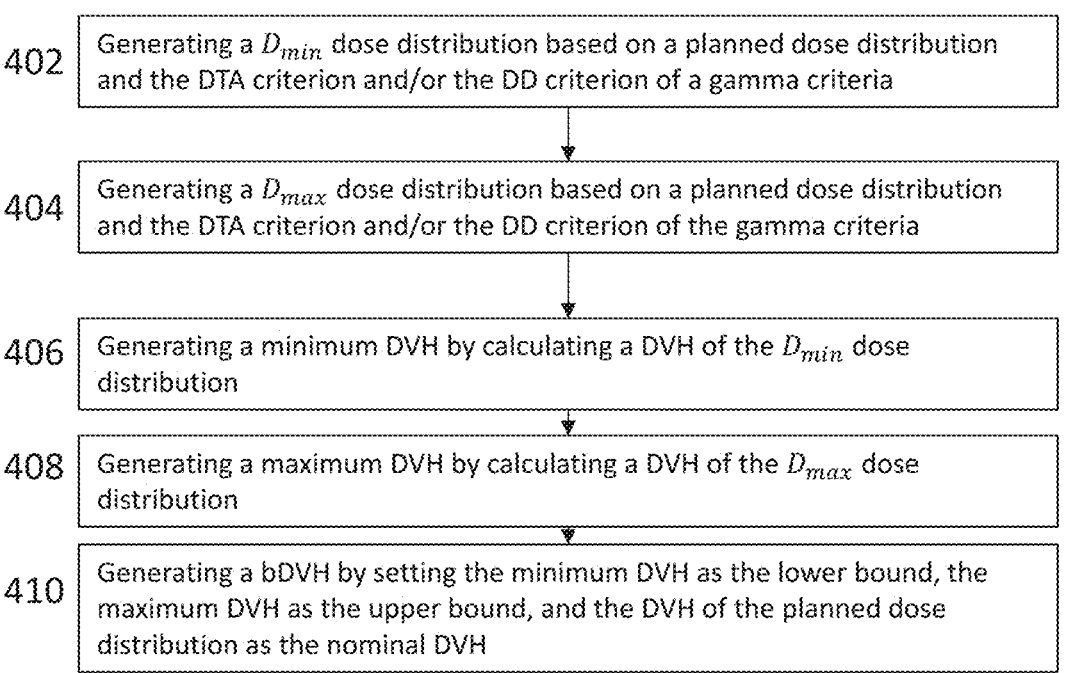

400

402 Generating a $D_{min}$ dose distribution based on a planned dose distribution and the DTA criterion and/or the DD criterion of a gamma criteria 404 Generating a $D_{max}$ dose distribution based on a planned dose distribution and the DTA criterion and/or the DD criterion of the gamma criteria 406 Generating a minimum DVH by calculating a DVH of the $D_{min}$ dose distribution 408 Generating a maximum DVH by calculating a DVH of the $D_{max}$ dose distribution 410 Generating a bDVH by setting the minimum DVH as the lower bound, the maximum DVH as the upper bound, and the DVH of the planned dose distribution as the nominal DVH

FIG. 4A

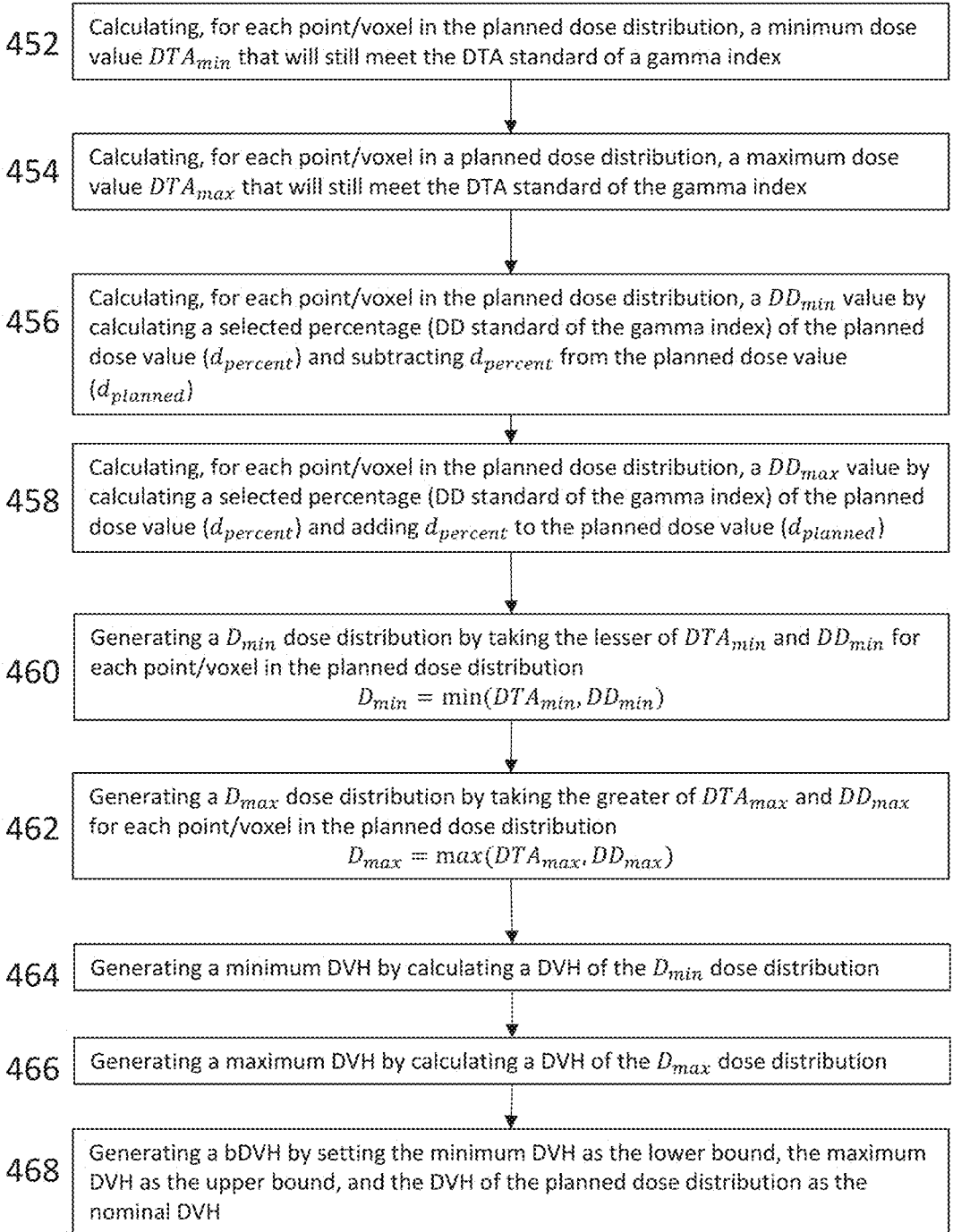

450

452 | Calculating, for each point/voxel in the planned dose distribution, a minimum dose value $DTA_{min}$ that will still meet the DTA standard of a gamma index 454 | Calculating, for each point/voxel in a planned dose distribution, a maximum dose value $DTA_{max}$ that will still meet the DTA standard of the gamma index 456 | Calculating, for each point/voxel in the planned dose distribution, a $DD_{min}$ value by calculating a selected percentage (DD standard of the gamma index) of the planned dose value ($d_{percent}$) and subtracting $d_{percent}$ from the planned dose value ($d_{planned}$)

458 | Calculating, for each point/voxel in the planned dose distribution, a $DD_{max}$ value by calculating a selected percentage (DD standard of the gamma index) of the planned dose value ($d_{percent}$) and adding $d_{percent}$ to the planned dose value ($d_{planned}$)

460 | Generating a $D_{min}$ dose distribution by taking the lesser of $DTA_{min}$ and $DD_{min}$ for each point/voxel in the planned dose distribution
$$D_{min} = min(DTA_{min}, DD_{min})$$

462 | Generating a $D_{max}$ dose distribution by taking the greater of $DTA_{max}$ and $DD_{max}$ for each point/voxel in the planned dose distribution
$$D_{max} = max(DTA_{max}, DD_{max})$$

464 | Generating a minimum DVH by calculating a DVH of the $D_{min}$ dose distribution 466 | Generating a maximum DVH by calculating a DVH of the $D_{max}$ dose distribution 468 | Generating a bDVH by setting the minimum DVH as the lower bound, the maximum DVH as the upper bound, and the DVH of the planned dose distribution as the nominal DVH

FIG. 4C

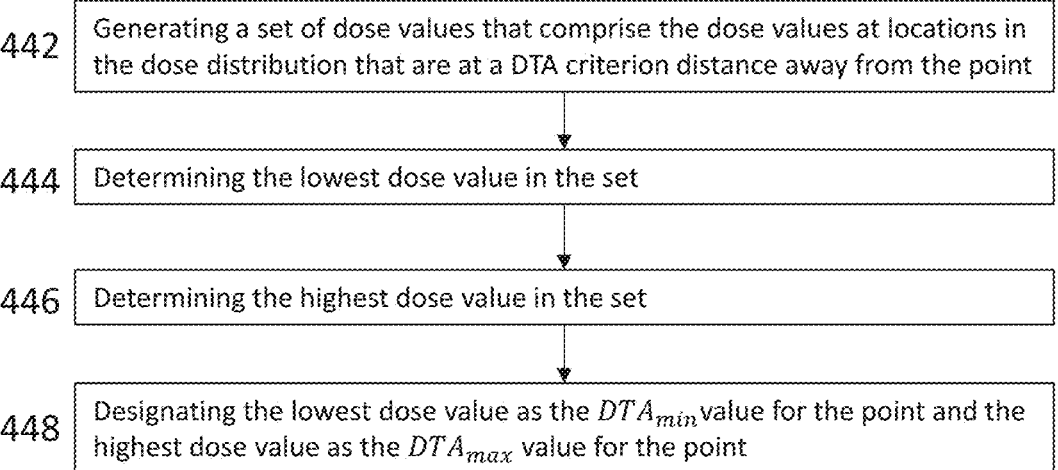

440

442 | Generating a set of dose values that comprise the dose values at locations in the dose distribution that are at a DTA criterion distance away from the point 444 | Determining the lowest dose value in the set 446 | Determining the highest dose value in the set 448 | Designating the lowest dose value as the $DTA_{min}$ value for the point and the highest dose value as the $DTA_{max}$ value for the point

FIG. 4D

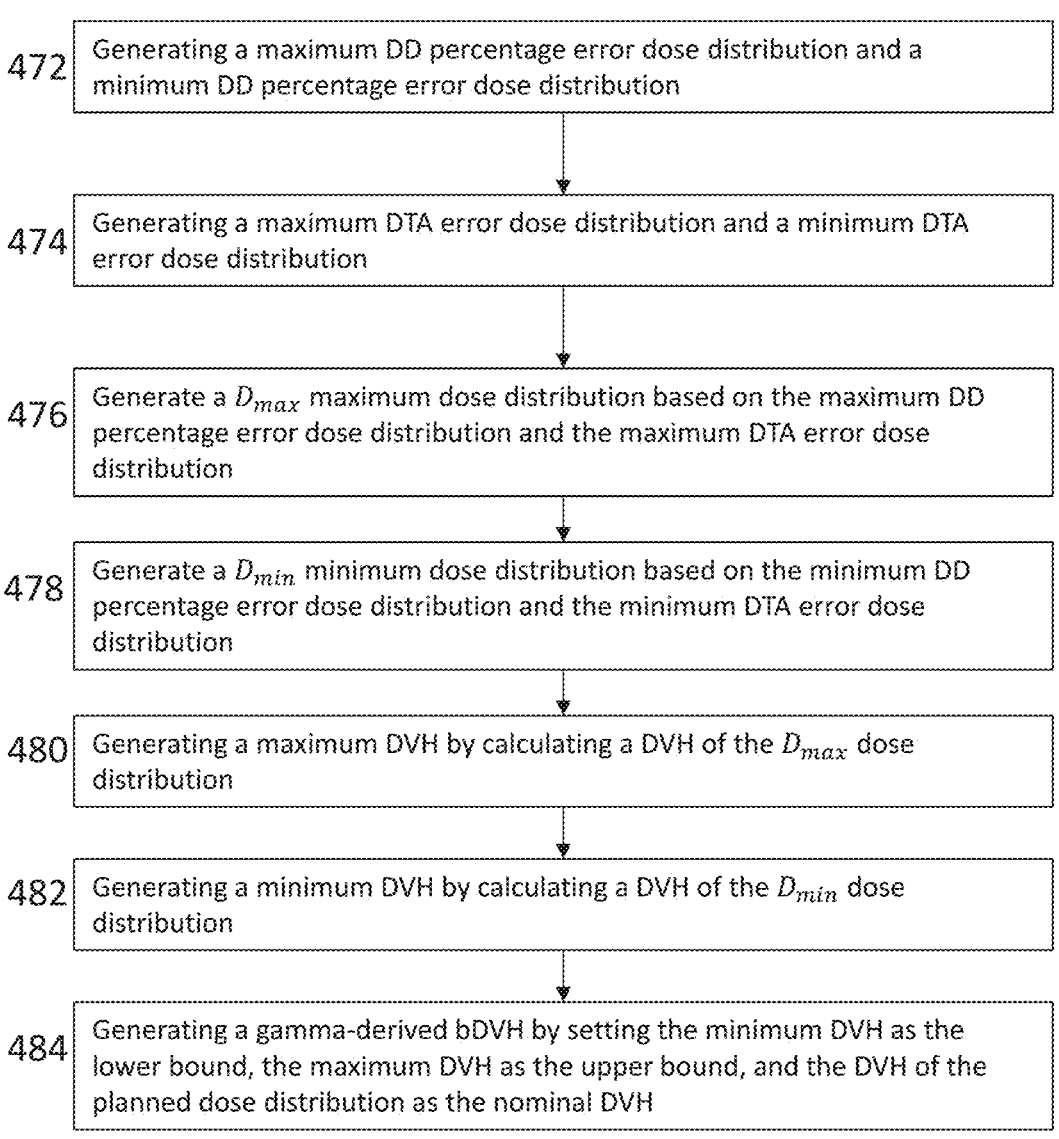

470

472 | Generating a maximum DD percentage error dose distribution and a minimum DD percentage error dose distribution 474 | Generating a maximum DTA error dose distribution and a minimum DTA error dose distribution 476 | Generate a $D_{max}$ maximum dose distribution based on the maximum DD percentage error dose distribution and the maximum DTA error dose distribution 478 | Generate a $D_{min}$ minimum dose distribution based on the minimum DD percentage error dose distribution and the minimum DTA error dose distribution 480 | Generating a maximum DVH by calculating a DVH of the $D_{max}$ dose distribution 482 | Generating a minimum DVH by calculating a DVH of the $D_{min}$ dose distribution 484 | Generating a gamma-derived bDVH by setting the minimum DVH as the lower bound, the maximum DVH as the upper bound, and the DVH of the planned dose distribution as the nominal DVH

Figure 5:
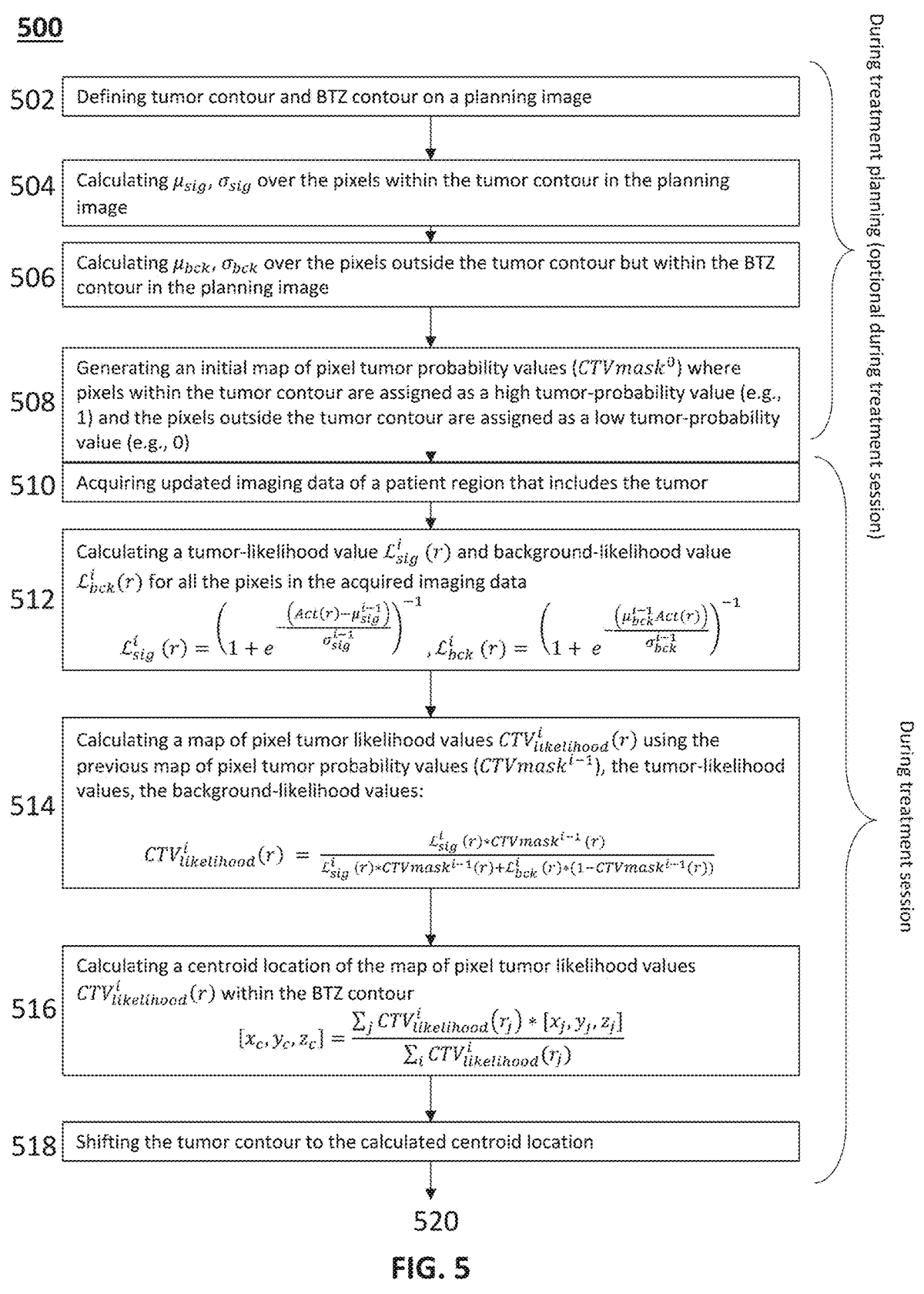

502 | Defining tumor contour and BTZ contour on a planning image

504 | Calculating $\mu_{sig}$, $\sigma_{sig}$ over the pixels within the tumor contour in the planning image 506 | Calculating $\mu_{bck}$, $\sigma_{bck}$ over the pixels outside the tumor contour but within the BTZ contour in the planning image 508 | Generating an initial map of pixel tumor probability values ($CTVmask^0$) where pixels within the tumor contour are assigned as a high tumor-probability value (e.g., 1) and the pixels outside the tumor contour are assigned as a low tumor-probability value (e.g., 0)

510 | Acquiring updated imaging data of a patient region that includes the tumor 512 | Calculating a tumor-likelihood value $\mathcal{L}^i_{sig}(r)$ and background-likelihood value $\mathcal{L}^i_{bck}(r)$ for all the pixels in the acquired imaging data $$\mathcal{L}^i_{sig}(r) = \left(1 + e^{-\left(\frac{Act(r)-\mu^{i-1}_{sig}}{\sigma^{i-1}_{sig}}\right)}\right)^{-1}, \mathcal{L}^i_{bck}(r) = \left(1 + e^{-\left(\frac{\mu^{i-1}_{bck}Act(r)}{\sigma^{i-1}_{bck}}\right)}\right)^{-1}$$

514 | Calculating a map of pixel tumor likelihood values $CTV^i_{likelihood}(r)$ using the previous map of pixel tumor probability values ($CTVmask^{i-1}$), the tumor-likelihood values, the background-likelihood values:

$$CTV^i_{likelihood}(r) = \frac{\mathcal{L}^i_{sig}(r)*CTVmask^{i-1}(r)}{\mathcal{L}^i_{sig}(r)*CTVmask^{i-1}(r)+\mathcal{L}^i_{bck}(r)*(1-CTVmask^{i-1}(r))}$$

516 | Calculating a centroid location of the map of pixel tumor likelihood values $CTV^i_{likelihood}(r)$ within the BTZ contour $$[x_c, y_c, z_c] = \frac{\sum_j CTV^i_{likelihood}(r_j) * [x_j, y_j, z_j]}{\sum_i CTV^i_{likelihood}(r_j)}$$

518 | Shifting the tumor contour to the calculated centroid location

520

*During treatment planning (optional during treatment session)*

*During treatment session*

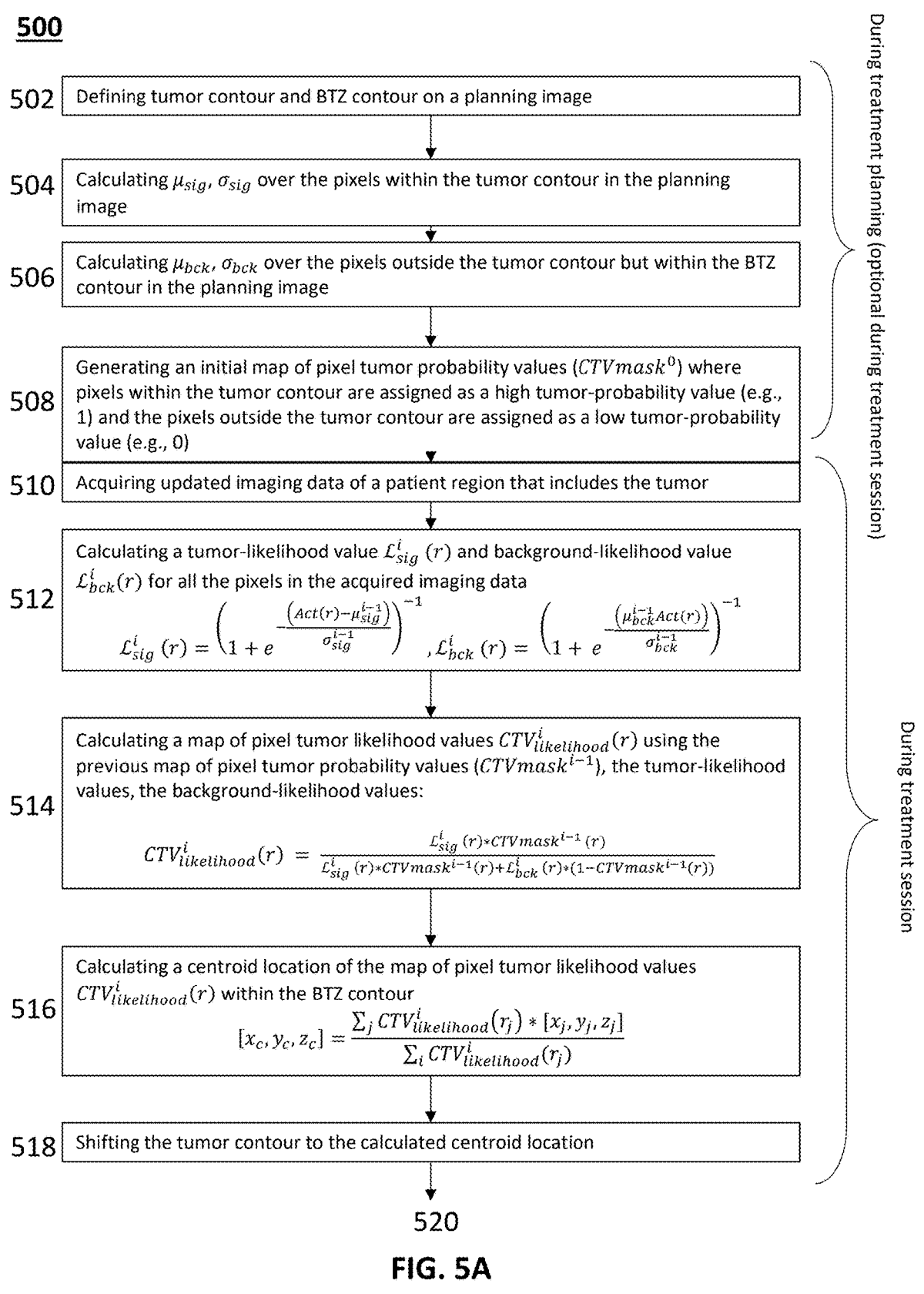

502 | Defining tumor contour and BTZ contour on a planning image

504 | Calculating $\mu_{sig}$, $\sigma_{sig}$ over the pixels within the tumor contour in the planning image 506 | Calculating $\mu_{bck}$, $\sigma_{bck}$ over the pixels outside the tumor contour but within the BTZ contour in the planning image 508 | Generating an initial map of pixel tumor probability values ($CTVmask^0$) where pixels within the tumor contour are assigned as a high tumor-probability value (e.g., 1) and the pixels outside the tumor contour are assigned as a low tumor-probability value (e.g., 0)

510 | Acquiring updated imaging data of a patient region that includes the tumor 512 | Calculating a tumor-likelihood value $\mathcal{L}^i_{sig}(r)$ and background-likelihood value $\mathcal{L}^i_{bck}(r)$ for all the pixels in the acquired imaging data $$\mathcal{L}^i_{sig}(r) = \left(1 + e^{-\frac{\left(Act(r)-\mu^{i-1}_{sig}\right)}{\sigma^{i-1}_{sig}}}\right)^{-1}, \mathcal{L}^i_{bck}(r) = \left(1 + e^{-\frac{\left(\mu^{i-1}_{bck}Act(r)\right)}{\sigma^{i-1}_{bck}}}\right)^{-1}$$

514 | Calculating a map of pixel tumor likelihood values $CTV^i_{likelihood}(r)$ using the previous map of pixel tumor probability values ($CTVmask^{i-1}$), the tumor-likelihood values, the background-likelihood values:

$$CTV^i_{likelihood}(r) = \frac{\mathcal{L}^i_{sig}(r)*CTVmask^{i-1}(r)}{\mathcal{L}^i_{sig}(r)*CTVmask^{i-1}(r)+\mathcal{L}^i_{bck}(r)*(1-CTVmask^{i-1}(r))}$$

516 | Calculating a centroid location of the map of pixel tumor likelihood values $CTV^i_{likelihood}(r)$ within the BTZ contour $$[x_c, y_c, z_c] = \frac{\sum_j CTV^i_{likelihood}(r_j) * [x_j, y_j, z_j]}{\sum_i CTV^i_{likelihood}(r_j)}$$

518 | Shifting the tumor contour to the calculated centroid location

520

During treatment planning (optional during treatment session)

During treatment session

FIG. 5A

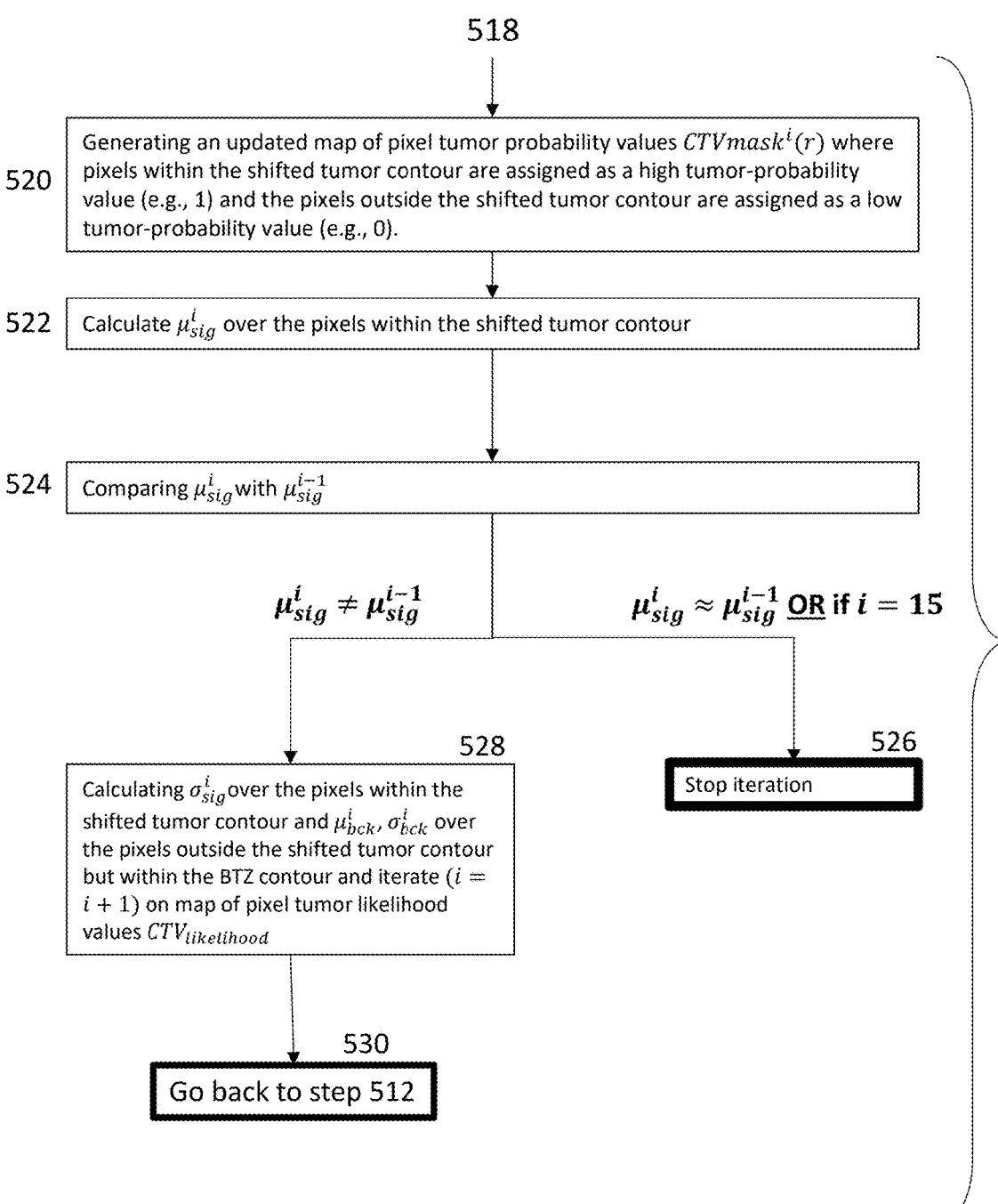

518

520  Generating an updated map of pixel tumor probability values $CTVmask^i(r)$ where pixels within the shifted tumor contour are assigned as a high tumor-probability value (e.g., 1) and the pixels outside the shifted tumor contour are assigned as a low tumor-probability value (e.g., 0).

522  Calculate $\mu_{sig}^i$ over the pixels within the shifted tumor contour

524  Comparing $\mu_{sig}^i$ with $\mu_{sig}^{i-1}$ $\mu_{sig}^i \neq \mu_{sig}^{i-1}$          $\mu_{sig}^i \approx \mu_{sig}^{i-1}$ OR if $i = 15$ 528  Calculating $\sigma_{sig}^i$ over the pixels within the shifted tumor contour and $\mu_{bck}^i, \sigma_{bck}^i$ over the pixels outside the shifted tumor contour but within the BTZ contour and iterate ($i = i + 1$) on map of pixel tumor likelihood values $CTV_{likelihood}$ 526  Stop iteration 530  Go back to step 512

During treatment session

FIG. 5B

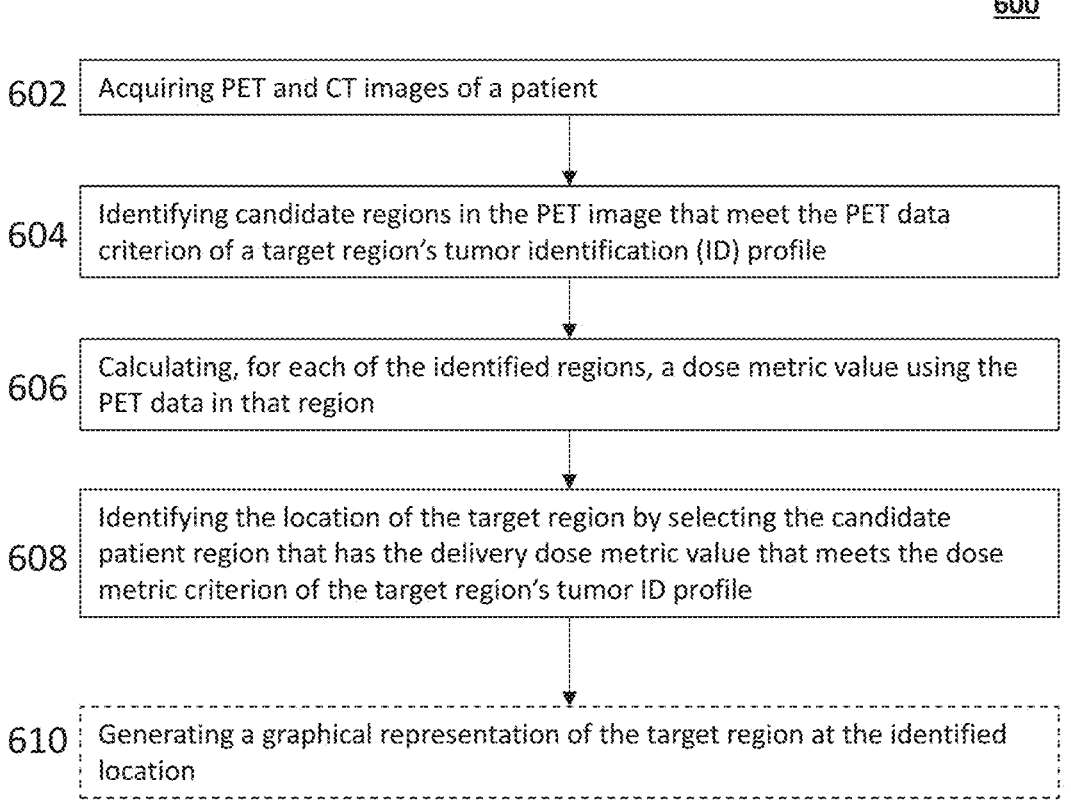

600

602 | Acquiring PET and CT images of a patient

604 | Identifying candidate regions in the PET image that meet the PET data criterion of a target region's tumor identification (ID) profile 606 | Calculating, for each of the identified regions, a dose metric value using the PET data in that region 608 | Identifying the location of the target region by selecting the candidate patient region that has the delivery dose metric value that meets the dose metric criterion of the target region's tumor ID profile 610 | Generating a graphical representation of the target region at the identified location

FIG. 6A

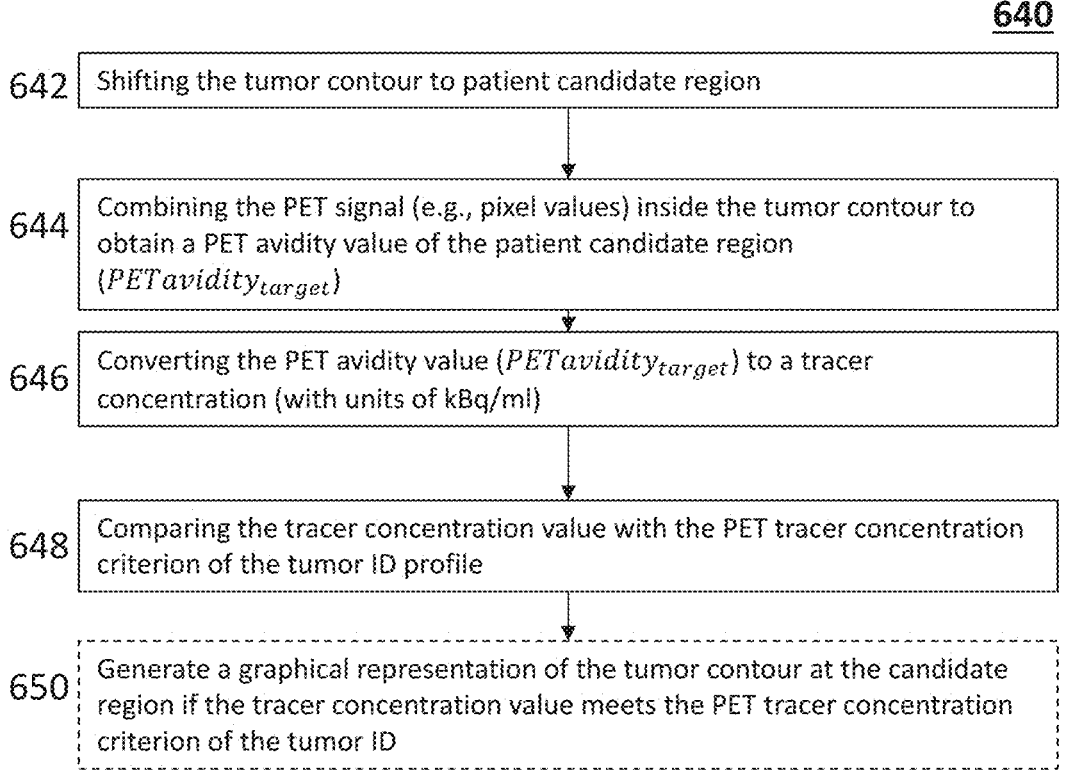

640

642 — Shifting the tumor contour to patient candidate region

644 — Combining the PET signal (e.g., pixel values) inside the tumor contour to obtain a PET avidity value of the patient candidate region ($PETavidity_{target}$)

646 — Converting the PET avidity value ($PETavidity_{target}$) to a tracer concentration (with units of kBq/ml)

648 — Comparing the tracer concentration value with the PET tracer concentration criterion of the tumor ID profile 650 — Generate a graphical representation of the tumor contour at the candidate region if the tracer concentration value meets the PET tracer concentration criterion of the tumor ID

FIG. 6C

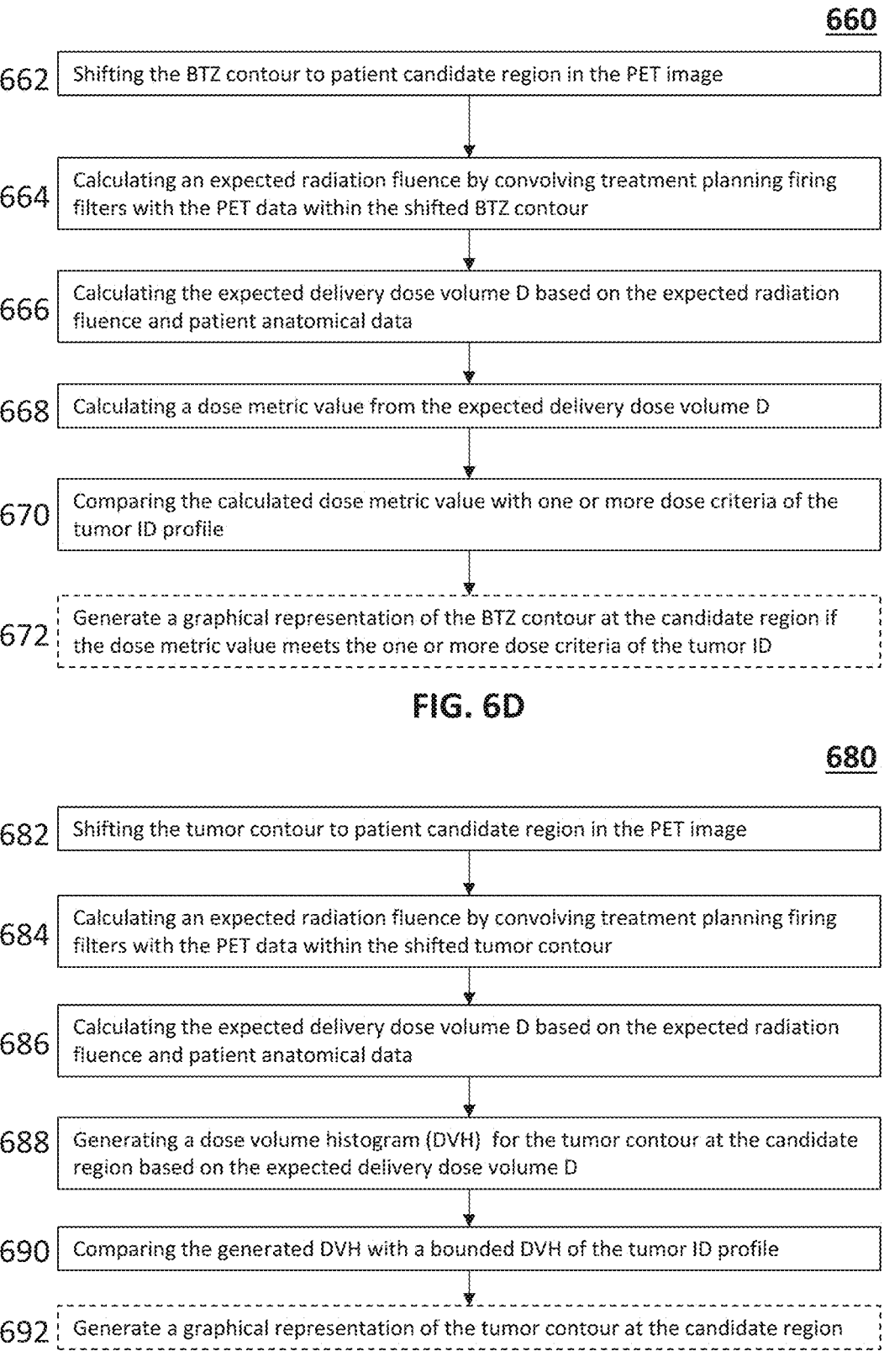

660

662 | Shifting the BTZ contour to patient candidate region in the PET image

664 | Calculating an expected radiation fluence by convolving treatment planning firing filters with the PET data within the shifted BTZ contour 666 | Calculating the expected delivery dose volume D based on the expected radiation fluence and patient anatomical data 668 | Calculating a dose metric value from the expected delivery dose volume D 670 | Comparing the calculated dose metric value with one or more dose criteria of the tumor ID profile 672 | Generate a graphical representation of the BTZ contour at the candidate region if the dose metric value meets the one or more dose criteria of the tumor ID

682 | Shifting the tumor contour to patient candidate region in the PET image

684 | Calculating an expected radiation fluence by convolving treatment planning firing filters with the PET data within the shifted tumor contour 686 | Calculating the expected delivery dose volume D based on the expected radiation fluence and patient anatomical data 688 | Generating a dose volume histogram (DVH) for the tumor contour at the candidate region based on the expected delivery dose volume D 690 | Comparing the generated DVH with a bounded DVH of the tumor ID profile 692 | Generate a graphical representation of the tumor contour at the candidate region

FIG. 6E

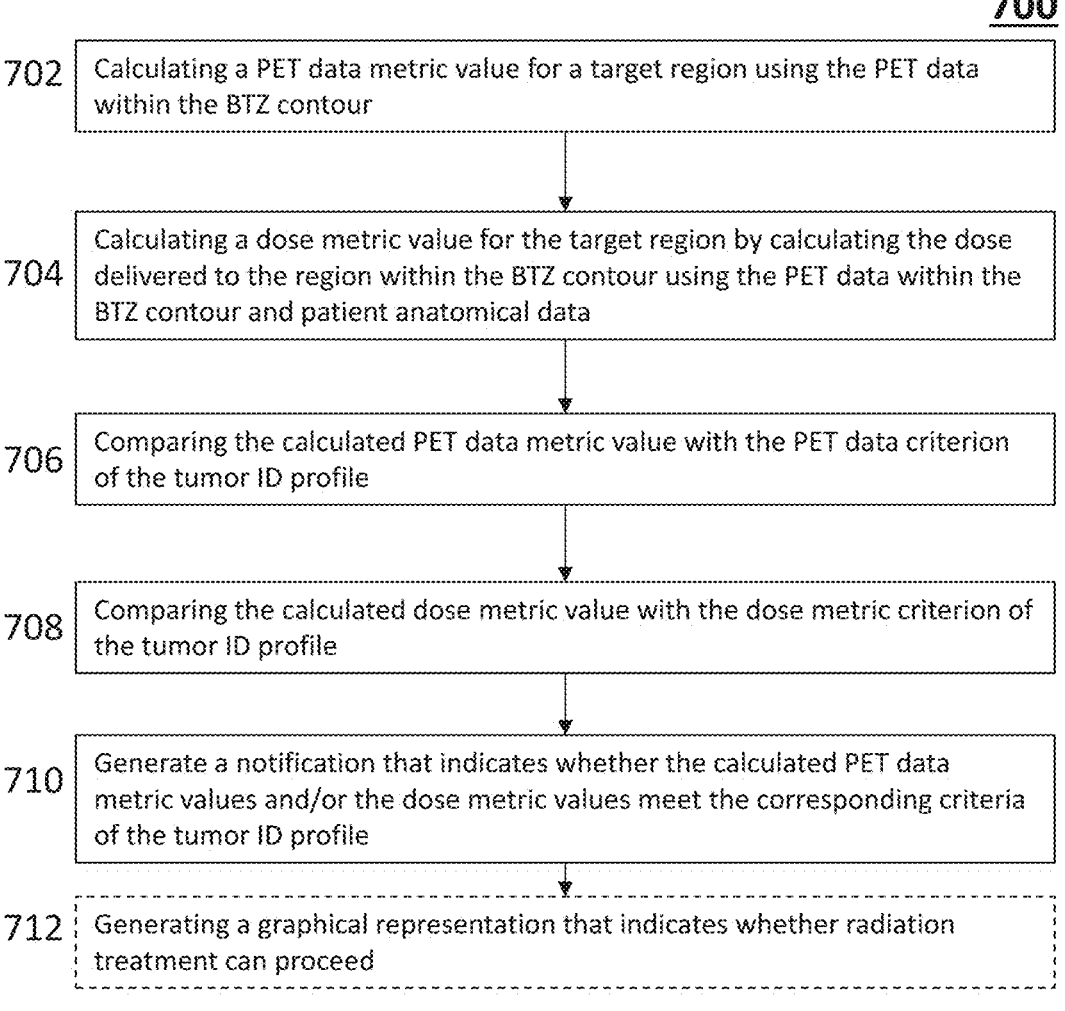

700

702 | Calculating a PET data metric value for a target region using the PET data within the BTZ contour 704 | Calculating a dose metric value for the target region by calculating the dose delivered to the region within the BTZ contour using the PET data within the BTZ contour and patient anatomical data 706 | Comparing the calculated PET data metric value with the PET data criterion of the tumor ID profile 708 | Comparing the calculated dose metric value with the dose metric criterion of the tumor ID profile 710 | Generate a notification that indicates whether the calculated PET data metric values and/or the dose metric values meet the corresponding criteria of the tumor ID profile 712 | Generating a graphical representation that indicates whether radiation treatment can proceed

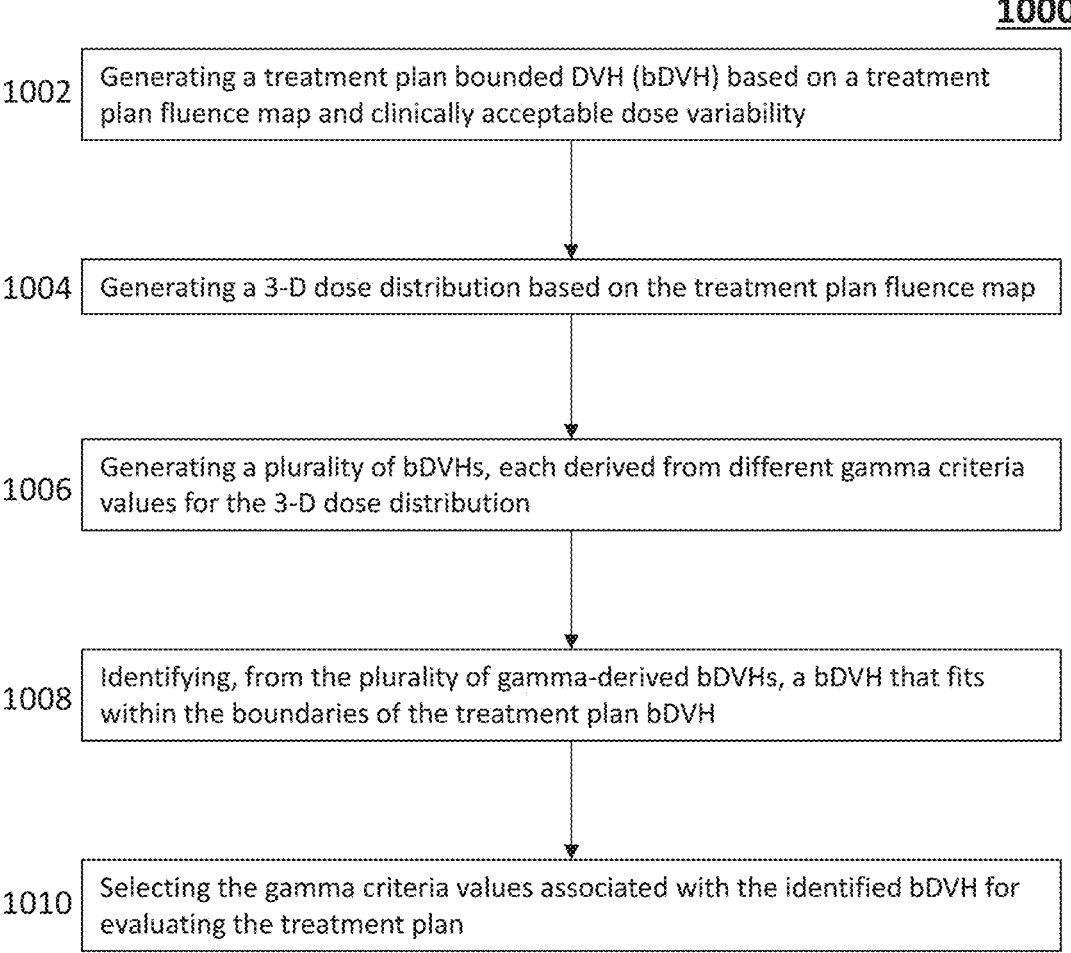

1002 | Generating a treatment plan bounded DVH (bDVH) based on a treatment plan fluence map and clinically acceptable dose variability 1004 | Generating a 3-D dose distribution based on the treatment plan fluence map 1006 | Generating a plurality of bDVHs, each derived from different gamma criteria values for the 3-D dose distribution 1008 | Identifying, from the plurality of gamma-derived bDVHs, a bDVH that fits within the boundaries of the treatment plan bDVH 1010 | Selecting the gamma criteria values associated with the identified bDVH for evaluating the treatment plan

FIG. 10A

METHODS FOR AUTOMATIC TARGET IDENTIFICATION, TRACKING, AND SAFETY EVALUATION FOR RADIOTHERAPY

CROSS-REFERENCE TO RELATED APPLICATIONS

This application is a continuation of International Application No. PCT/US2022/017375, filed Feb. 22, 2022, which claims priority to U.S. Provisional Patent Application No. 63/154,295, filed Feb. 26, 2021, U.S. Provisional Patent Application No. 63/221,859, filed Jul. 14, 2021, and U.S. Provisional Patent Application No. 63/246,212, filed Sep. 20, 2021, the disclosures of which are hereby incorporated by reference in their entireties.

BACKGROUND

The goal of radiotherapy is to deliver a lethal dose of radiation to tumors while limiting the radiation exposure of surrounding healthy tissue. However, because both tumors and the radiation are not readily visible or apparent (since tumors are inside the patient and high-energy X-rays are not in the visible spectrum), it can be difficult to ascertain whether the therapeutic radiation beams are correctly targeted at the tumors. Current radiotherapy methods seek to mitigate this localization issue by planning the radiation delivery based on a planning image and assuming that if the patient is positioned in the same location that they were in when the planning image was acquired, the tumor would be in the same location as well. At the time of treatment, a localization anatomical image (such as a CT scan) of the patient is acquired, and this image is compared with a planning image of the patient. The patient may then be moved based on the comparison so that they are at the planning image location.

Even though the localization image may help position the patient so that the tumor(s) are positioned at their planning location, there is typically some patient motion during a treatment session that may cause the tumor(s) to change location. For example, the tumor may change location during the treatment session due to breathing, internal organ motion, and may sometimes change location relative to the anatomical landmarks used to align the treatment localization image with planning image. Localization images acquired at the beginning of a treatment session do not account for these location changes. Current radiotherapy systems seek to mitigate delivery artifacts arising from intra-fractional tumor motion by incorporating motion models into treatment planning, gating the emission of radiation based on motion models, expanding treatment margins (e.g., planning target volume or PTV), etc. The uncertainties described above compound when there is more than one tumor to be irradiated.

Accordingly, improved methods for identifying the location of a target region, especially in the context of treating metastatic disease, are desirable.

SUMMARY

Disclosed herein are radiotherapy systems and methods for identifying the location of one or more target regions during a treatment session using a tumor identification (ID) profile. These methods may help facilitate the localization of one or more target regions during a treatment session. The systems and methods described herein may also be used for evaluating the safety of continued radiation delivery during a treatment session.

Also disclosed herein are methods for updating the location of a moving target region (e.g., a tumor) by iteratively modifying an image of the target region based on a statistical map (e.g., a map of likelihood values) that is updated with sparse imaging data.

Also disclosed herein are methods for analyzing a dose distribution to a target region by generating a bounded dose volume histogram (bDVH) based on gamma criteria comprising a distance-to-agreement (DTA) criterion and a dose difference (DD) criterion. The bDVH generated based on gamma criteria (also referred to as a gamma-derived bDVH) may be used in a method for selecting gamma criteria for evaluating a radiotherapy treatment plan. In one variation, a method for selecting gamma criteria may comprise generating one or more bDVHs based on a set of gamma criteria, identifying the gamma-derived bDVH that fits within the bounds of an acceptable bDVH, and selecting the gamma criteria associated with the identified gamma-derived bDVH for evaluating the treatment plan.

One variation of a method for identifying a patient target region may comprise acquiring a PET image of a patient having a target region, identifying regions within the PET image having PET data that satisfy a PET data criterion of a tumor identification (ID) profile, where the tumor ID profile further comprises a dose metric criterion, calculating, for each of the identified regions, a dose metric value based on the PET data in the PET image, and selecting the region that has a dose metric value that meets the dose metric criterion as the target region. A dose metric value may be an expected delivered dose calculated from the PET data. A dose metric criterion may be a threshold or standard value for evaluating a dose distribution to a region of an image (e.g., PET image), for example, to determine whether the region is likely to be part of the target region or not. The tumor ID profile may comprise a plurality of identification parameters including the PET data criterion and dose metric criterion and may further comprise a target region contour and a biology-tracking zone (BTZ) contour that have been defined using one or more of PET imaging data, CT imaging data, and MR imaging data during treatment planning. The BTZ is a defined region (e.g., a volume) from which PET imaging data is used to calculate the radiation fluence for delivery. The BTZ contour may encompass the target region contour. In some variations, the BTZ contour may be an image mask such that image pixels outside of the BTZ contour are set to zero. A PET data criterion may be a threshold or standard value for evaluating PET data, for example, to determine whether a region of a PET image is likely to be part of the target region or not. The PET data criterion may comprise one or more of a mean SUV, maximum SUV, normalized target signal (NTS), and mean PET tracer concentration. In some variations, the NTS may be a ratio of a maximum PET signal value within a BTZ contour to a mean PET signal value within the BTZ contour. Alternatively, the NTS may be a ratio of a difference between a mean SUV value within the target region contour and a mean SUV within the BTZ contour, and a mean SUV within the BTZ contour but outside the target region contour. In some variations, the NTS may be a ratio of a mean value $(PET_{mean\text{-}50\%})$ of voxels within the BTZ contour having a voxel value greater than 50% of the maximum voxel value in the BTZ contour and a mean value $(PET_{mean\_bkgnd})$ of pixels/voxels within a BTZ shell contour that encompasses the BTZ contour:

$$NTS = \frac{PET_{mean-50\%}}{PET_{mean-bkgnd}}$$

In some variations, the NTS may be a ratio of a mean value ($PET_{mean-80\%}$) of voxels within the BTZ contour having a voxel value greater than 80% of the maximum voxel value in the BTZ contour and a mean value ($PET_{mean-bkgnd}$) of pixels/voxels within a BTZ shell contour that encompasses the BTZ contour:

$$NTS = \frac{PET_{mean-80\%}}{PET_{mean-bkgnd}}$$

In some variations, calculating the dose metric value for each of the identified regions may comprise calculating an expected delivery dose volume (D). The dose metric value may be an expected delivered dose to the target region that is calculated based on the dose volume D and the target region contour, and the dose metric criterion may be a mean dose amount and/or a maximum dose amount within the target region contour. Alternatively, the dose metric value may be an expected delivered dose to the target region that is calculated based on the dose volume D and the BTZ contour, and the dose metric criterion may be a mean dose amount and/or a maximum dose amount within the BTZ contour. In some variations, the dose metric criterion may be one or more of a mean dose amount, a maximum dose amount, and a minimum dose amount delivered to the patient. The dose metric criterion may comprise a volume quantity contained within an isodose line in the dose volume D. For example, the isodose line may be a X % isodose line, where X is from about 50 to about 100. The plurality of identification parameters may further comprise a dose volume histogram (DVH) criterion over one or more sub-volumes in the dose volume D, and calculating the dose metric value for each of the identified regions may further comprise calculating a DVH for one or more of the target region contour and the BTZ contour, and where selecting the region as the target region may comprise selecting the region that has a DVH that meets the DVH criterion of the tumor ID profile. Alternatively, or additionally, the plurality of identification parameters may comprise an organ-at-risk (OAR) DVH criterion, and calculating the dose metric value for each of the identified regions may comprise calculating a DVH for an OAR contour, and selecting the region as the target region may further comprise selecting the region that has an OAR DVH that meets the OAR DVH criterion of the tumor ID profile.

In some variations, identifying regions within the PET image may comprise identifying portions of the PET image that have image features that are similar to image features of a previously-acquired PET image of the patient target region, shifting the BTZ contour and target region contour to the identified portions of the PET image, calculating SUV metric values for the shifted target region contour at each of the identified portions of the PET image, and identifying regions within the PET image by comparing the calculated SUV metric values with PET data criterion of the tumor ID profile. A PET data criterion may be a threshold or standard value for evaluating PET data, for example, to determine whether a region of a PET image is likely to be part of the target region or not. Identifying portions of the PET image that have image features that are similar to image features of the previously-acquired PET image may comprise template-based matching using cross correlation. The PET data of the PET image may comprise one or more of a normalized target signal (NTS) value and a PET tracer concentration within the BTZ contour. For example, the PET data criterion of the tumor ID profile may comprise one or more of a minimum threshold value for a NSUV, a minimum PET tracer concentration within the BTZ contour. In some variations, identifying regions within the PET image may comprise generating visual indicia that highlights each of the identified regions in the PET image and displaying the visual indicia on a display device (e.g., a monitor). Selecting the region as the target region may comprise generating visual indicia that highlights the target region and displaying the visual indicia on a display device (e.g., a monitor). In some variations, the target region may be a first target region and the tumor ID profile may be a first tumor ID profile, and where the PET image may include a second target region, and the method may further comprise identifying a second set of regions within the PET image having PET data that meet PET data criterion of a second tumor ID profile, where the second tumor ID profile comprises further comprises a dose metric criterion, calculating, for the identified regions in the second set, a dose metric value based on the PET data in the PET image, and selecting the region in the second set of identified regions that has a dose metric value that meets the dose metric criterion of the second tumor ID profile as the second target region.

Also described herein are methods for defining a tumor identification profile. One variation of a method for defining a tumor identification profile may comprise outlining a target region within acquired PET and CT images, outlining a biology-tracking zone (BTZ) that encompasses the target region, calculating a PET data metric value of the target region using the PET image, calculating a dose metric value of the target region based on the PET image, the BTZ outline, and firing filters calculated based on a prescribed dose to the target region, and generating the tumor identification (ID) profile comprising a plurality of identification parameters comprising a PET data criterion calculated from the PET data metric value and a dose metric criterion calculated from the dose metric value. Firing filters may be a mapping or transformation (e.g., a transformation matrix) that designates the conversion of imaging data into a radiation fluence that when delivered, provides the desired dose to the target region. The firing filters represent a transformation from an image (or from the image space) to a fluence (or to fluence space). The plurality of identification parameters may further comprise the target region outline and the BTZ outline. In some variations, the method may further comprise acquiring MR imaging data and outlining the target region and outlining the BTZ may use the MR imaging data. The BTZ may be a spatial mask for an image such that image pixels outside the BTZ are set to zero. The PET data criterion may comprise a standard uptake value (SUV) metric value for the target region. A SUV value may be calculated based on the intensity values of the voxels in a region of a PET image (e.g., target region, selected set of voxels) and the radioactivity of the tracer. The intensity values of the voxels may be calibrated to represent the radioactivity concentration at that voxel. For example, a SUV value may be calculated by taking the ratio of tissue radioactivity concentration (e.g., in kBq/mL) of a region in the PET image to the radioactivity of the injected tracer (e.g., MBq) per patient weight (kg). For example, the SUV metric value may comprise one or more of a normalized target signal (NTS), mean SUV, and maximum SUV. In some variations, the identification parameters may further comprise PET imaging data that has been masked by the BTZ and/or CT imaging data that has been masked by the BTZ. Alternatively, or additionally, the identification parameters may further comprise a metabolic tumor volume derived from the PET and CT images of the patient. In some variations, the target region outline may be delineated in one or more of the PET and CT images. The PET data criterion may comprise a PET tracer concentration within the target region outline. For example, the PET tracer concentration may be a normalized PET tracer concentration, where the PET tracer concentration within the target region outline is normalized to a PET tracer concentration within the BTZ outline. Alternatively, or additionally, the PET data criterion may comprise a PET tracer concentration in the BTZ outline.

In some variations, calculating the dose metric value may comprise calculating an expected delivery dose volume (D) based on the acquired PET and CT images. The dose metric criterion may be a mean dose amount and/or a maximum dose amount within the target region outline calculated using the dose volume D. Alternatively, or additionally, the dose metric criterion may be a mean dose amount and/or a maximum dose amount within the BTZ outline calculated using the dose volume D. The dose metric criterion may be one or more of a mean dose amount, a maximum dose amount, and a minimum dose amount to the target region, and/or may be one or more of a mean dose amount, a maximum dose amount, and a minimum dose amount to a radiation-avoidance region. In some variations, the dose metric criterion may be specified by a dose volume histogram (DVH) for one or more of the target region outline and the BTZ outline.

Also described herein are methods for calculating multiple delivery fluences. Optionally, the calculated delivery fluences may be used to irradiate multiple target regions. One variation of a method for treating multiple target regions may comprise adjusting a patient's position on a patient platform of a radiotherapy system such that a location of an anatomical landmark matches with a planning location of the anatomical landmark, acquiring PET imaging data of the patient that includes a first target region and a second target region, identifying a first location of the first target region using the acquired PET imaging data and a first tumor identification (ID) profile that comprises a plurality of identification parameters that characterize the first target region, identifying a second location of the second target region using the acquired PET imaging data and a second tumor identification (ID) profile that comprises a second plurality of identification parameters that characterize the second target region, calculating a first delivery fluence for delivery to the first location of the first target region using the acquired PET imaging data, and calculating a second delivery fluence to the second location of the second target region using the acquire PET imaging data. Calculating the first delivery fluence may comprise calculating a first localization function based on the first location, and applying the first localization function to a first shift-invariant firing filter to calculate the first delivery fluence. The first location may correspond with a first planned localization reference point for the first target region, and the first shift-invariant firing filter may be derived from the first planned localization reference point. Applying the first localization function to a first shift-invariant firing filter may comprise convolving the first localization function with the first shift-invariant firing filter. In some variations, the first localization function may be one of a delta function, Gaussian function, circular function, and an interpolation. In some variations, calculating the second delivery fluence may comprise calculating a second localization function based on the second location, and applying the second localization function to a second shift-invariant firing filter to calculate the second delivery fluence. The second location may correspond with a second planned localization reference point for the second target region, and the second shift-invariant firing filter is derived based on the second planned localization reference point. Applying the second localization function to a second shift-invariant firing filter may comprise convolving the second localization function with the second shift-invariant firing filter. In some variations, the second localization function may be one of a delta function, Gaussian function, circular function, and an interpolation.

In some variations, identifying the first location of the first target region may further comprise calculating a first predicted delivery dose based on the acquired PET imaging data, and determining whether the first predicted delivery dose is within approved dose thresholds. Identifying the second location of the second target region may further comprise calculating a second predicted delivery dose based on the acquired PET imaging data and determining whether the second predicted delivery dose is within approved dose thresholds. In some variations, the first predicted delivery dose may be within approved dose thresholds and the method further comprises emitting the first delivery fluence to the first location. In other variations, the first predicted delivery dose may be within approved dose thresholds and the second predicted dose may not be within approved dose threshold, and the method may further comprise emitting the first delivery fluence to the first location and not emitting the second delivery fluence to the second location. In variations where the second predicted delivery dose is within approved dose thresholds, the method may further comprise emitting the second delivery fluence to the second location. In some variations, at least a portion of the first delivery fluence and the second delivery fluence are emitted concurrently. Methods may optionally comprise generating a graphical representation that depicts the first predicted delivery dose, a first planned delivery dose for the first target region, the second predicted delivery dose, and a second planned delivery dose for the second target region, and outputting the graphical representation on a display device. The identification parameters of the first tumor ID profile may comprise a PET data criterion, and the method may optionally further comprise calculating a PET data metric value of the first target region and proceeding with emitting the first delivery fluence to the first location if the PET data metric meets the PET data criterion. In some variations, the identification parameters of the second tumor ID profile may comprise a second PET data criterion, and the method may further comprise calculating a second PET data metric value of the second target region and proceeding with emitting the second delivery fluence to the second location if the second PET data metric meets the second PET data criterion. Methods may optionally comprise generating a graphical representation that depicts the first target region at the identified first location superimposed over the first target region at a first planned location and the second target region at the second identified target location superimposed over the second target region at a second planned location, and outputting the graphical representation on a display device.

Also described herein are methods of evaluating safety during a radiotherapy treatment. One variation of a method of evaluating safety during a radiotherapy treatment may comprise acquiring PET imaging data of a target region, identifying a location of the target region using the acquired PET imaging data and a tumor identification (ID) profile that comprises a plurality of identification parameters that characterize the target region, calculating a predicted delivery dose based on the acquired PET imaging data, the location of the target region, and a target region contour, and determining whether the predicted delivery dose is within approved dose thresholds. Optionally, in some variations, methods may comprise delivering radiation to the target region if the predicted delivery dose is within approved dose thresholds. Acquiring PET imaging data, identifying the location, calculating the predicted delivery dose, and determining whether the predicted delivery dose is within approved dose thresholds may occur concurrently with delivering radiation to the target region. Acquiring PET imaging data may comprise acquiring PET imaging data during an interval of time during a treatment session. For example, the interval of time may have a duration of from about 30 seconds to about 15 minutes, or less than about one minute. In some variations, calculating the predicted delivery dose may use PET imaging data acquired during the interval of time. Alternatively, or additionally, calculating the predicted delivery dose may use PET imaging data cumulatively acquired during the treatment session. Optionally, some variations may further comprise generating a graphical representation that depicts the predicted delivery dose, a planned delivery dose for the target region, and outputting the graphical representation on a display device. Alternatively, or additionally, some methods may comprise calculating a delivered dose of radiation that has been emitted to the patient target region, and generating a graphical representation that depicts the delivered dose, the predicted delivery dose, and a planned delivery dose for the target region, and outputting the graphical representation on a display device.

Also disclosed herein are methods for locating a tumor based on an initial image and newly-acquired imaging data. One variation of a method may comprise acquiring imaging data of a patient region that includes a tumor, generating a map of pixel tumor likelihood values by calculating a tumor-likelihood value and background-likelihood value for each pixel of the imaging data, and determining a location of the tumor by shifting a tumor contour within the imaging data to a centroid location of the map of pixel tumor likelihood values within a BTZ contour, where the BTZ contour encompasses the tumor contour. Determining the location of the tumor may further comprise iteratively updating the map of pixel tumor likelihood values to generate a final map of pixel tumor likelihood values such that an average pixel value within the shifted tumor contour is within a previously-defined threshold of an average pixel value within a pre-shifted tumor contour, calculating a centroid location of the final map of pixel tumor likelihood values, and determining the location of the tumor by shifting the tumor contour to the calculated centroid location. Some variations may further comprise generating an initial map of pixel tumor probability values based on an initial image of the tumor, where the pixel tumor probability values are binary values and pixel likelihood values are any values greater than or equal to zero and less than or equal to one. The acquired imaging data of the tumor may comprise one or more of PET imaging data, CT imaging data, MR imaging data, and X-ray imaging data. In some variations, the method may further comprises generating an initial map of pixel tumor probability values based on an initial image of the tumor by assigning pixels within the tumor contour a high tumor-probability value and assigning pixels outside the tumor contour a low tumor-probability value. The high tumor-probability value may be one and the low tumor-probability value may be zero. Acquiring imaging data may comprise acquiring PET imaging data, CT imaging data, MR imaging data, and/or SPECT imaging data. In some variations, generating a map of pixel tumor likelihood values may comprise calculating a tumor-likelihood value and background-likelihood value for each pixel in the acquired imaging data. For example, calculating a tumor-likelihood value may comprise calculating an average pixel value over the pixels within the tumor contour and a standard deviation value of the pixel values within the tumor contour. Calculating a background-likelihood value may comprise calculating an average pixel value over the pixels outside the tumor contour and within the BTZ contour and a standard deviation value of the pixel values outside the tumor contour and within the BTZ contour. Iteratively updating the map of pixel tumor likelihood values may comprise updating the map of pixel tumor probability values by assigning pixels within the shifted tumor contour a high tumor-probability value and assigning pixels outside the shifted tumor contour a low tumor-probability value, updating tumor-likelihood values and background-likelihood values for each pixel in the acquired imaging data, and adjusting the map of pixel tumor likelihood values using the updated map of pixel tumor probability values, updated tumor-likelihood values, and background-likelihood values.

Optionally, the method may further comprise generating a graphical representation that comprises the tumor contour that has been shifted to the location of the tumor and displaying the graphical representation to a display device. Some variations may comprise generating a graphical representation that comprises the tumor contour that has been shifted to the centroid location of the final map of pixel tumor likelihood values, the acquired updated imaging data, and displaying the graphical representation to a display device. The graphical representation(s) may further comprise the BTZ contour, and the shifted tumor contour and BTZ contour may be superimposed on the acquired imaging data. Some methods may further comprise generating a notification if a proximity of the shifted tumor contour to the BTZ contour is within a pre-determined margin.

Described herein is a method for evaluating a PET signal for radiotherapy. One variation of a method may comprise acquiring PET imaging data of a patient region that includes a biology targeting zone (BTZ) region and a target region within the BTZ region, determining a location of the target region within the BTZ region based on the PET imaging data, calculating a target region standard uptake value (SUV) for pixels of the PET imaging data within the target region, calculating a BTZ region SUV for pixels of the PET imaging data outside the target region and within the BTZ region, calculating a normalized PET signal metric value of the target region using the target region SUV and the BTZ region SUV, and evaluating the PET imaging data by comparing the normalized PET signal metric value with a planning PET signal metric value. A SUV value may be calculated based on the intensity values of the voxels in a region of a PET image (e.g., target region) and the radioactivity of the tracer. The intensity values of the PET image voxels may be calibrated to represent the radioactivity concentration at that voxel. For example, a SUV value may be calculated by taking the ratio of tissue radioactivity concentration (e.g., in kBq/mL) of a region in the PET image to the radioactivity of the injected tracer (e.g., MBq) per patient weight (kg). Optionally, in some variations, this method may use a mean SUV of a target region and a mean SUV of a BTZ region. Comparing the normalized PET signal metric value with a planning PET signal metric value may comprise calculating a predicted radiation dose for the target region based on the net PET signal metric value and comparing the predicted radiation dose with a prescribed radiation dose. Determining the location of the target region may comprise generating a map of pixel tumor likelihood values by calculating a tumor-likelihood value and background-likelihood value for each pixel of the PET imaging data, shifting a contour of the target region to a centroid location of the map of pixel tumor likelihood values, iteratively updating the map of pixel tumor likelihood values to generate a final map of pixel tumor likelihood values such that an average pixel value within the shifted target region contour is within a previously-defined threshold of an average pixel value within a pre-shifted tumor contour, calculating a centroid location of the final map of pixel tumor likelihood values, and determining the target region location by shifting the target region contour to the calculated centroid location.

One variation of a method for locating a tumor based on an initial image and newly-acquired imaging data may comprise acquiring updated imaging data of a patient region that includes the tumor, wherein Act (r) represents a signal intensity at each volumetric pixel r=(x, y, z) of the imaging data, calculating, for a first iteration where i=1, a tumor-likelihood value $$\mathcal{L}^i_{sig}(r)$$

and background-likelihood value $$\mathcal{L}^i_{bck}(r)$$

for each pixel of the updated imaging data, generating a map of pixel tumor likelihood values $$CTV^i_{likelihood}(r)$$

by combining the tumor-likelihood value $$\mathcal{L}^i_{sig}(r)$$

and background-likelihood value $$\mathcal{L}^i_{bck}(r)$$

with an initial map of pixel tumor probability values CTV-mask$^{i-1}$ derived from an initial image of a tumor, wherein the initial image comprises a tumor contour and a BTZ contour that encompasses the tumor contour $$CTV^i_{likelihood}(r) = \frac{\mathcal{L}^i_{sig}(r) * CTVmask^{i-1}(r)}{\mathcal{L}^i_{sig}(r) * CTVmask^{i-1}(r) + \mathcal{L}^i_{bck}(r) * \left(1 - CTVmask^{i-1}(r)\right)},$$

calculating a centroid location of the map of pixel tumor likelihood values $$CTV^i_{likelihood}(r)$$

within the BTZ contour, shifting the tumor contour to the centroid location of the map of pixel tumor likelihood values $$CTV^i_{likelihood}(r),$$

iteratively updating, for multiple iterations i=i+1, the map of pixel tumor likelihood values $$CTV^i_{likelihood}(r)$$

to generate a final map of pixel tumor likelihood values $$CTV^i_{likelihood}(r)$$

until a stopping condition is met, calculating a centroid location of the final map of pixel tumor likelihood values, and determining a location of the tumor by shifting the tumor contour to the calculated centroid location.

Calculating the tumor-likelihood value $$\mathcal{L}^i_{sig}(r)$$

may comprise calculating a signal average and a signal standard deviation value $$\mu^{i-1}_{sig}, \sigma^{i-1}_{sig}$$

over the pixels within the tumor contour in the initial image and combining the signal average value, signal standard deviation value, the signal intensity and Act(r) as follows:

$$\mathcal{L}^i_{sig}(r) = \left(1 + e^{\left(\frac{Act(r)-\mu^{i-1}_{sig}}{\sigma^{i-1}_{sig}}\right)}\right)^{-1}$$

and calculating the background-likelihood value $$\mathcal{L}^i_{bck}(r)$$

may comprise calculating a background average signal value and a background standard deviation value $$\mu^{i-1}_{bck}, \sigma^{i-1}_{bck}$$

over the pixels outside the tumor contour in the initial image and combining the background average value, background standard deviation value, the signal intensity and Act(r) as follows:

$$\mathcal{L}^i_{bck}(r) = \left(1 + e^{\frac{\left(\mu^{i-1}_{bck} Act(r)\right)}{\sigma^{i-1}_{bck}}}\right)^{-1}.$$

In some variations, calculating the centroid location of the map of pixel tumor likelihood values $$CTV^i_{likelihood}(r)$$

may comprise calculating the coordinates of the centroid $[x_c, y_c, z_c]$ over the j pixels within the BTZ contour:

$$[x_c, y_c, z_c] = \frac{\sum_j CTV^i_{likelihood}(r_j) * [x_j, y_j, z_j]}{\sum_i CTV^i_{likelihood}(r_j)}.$$

In some variations, the stopping condition may be that an average pixel value $$\mu^i_{sig}$$

within the shifted tumor contour is within a previously-defined threshold of an average pixel value $$\mu^{i-1}_{sig}$$

within the pre-shifted tumor contour. Alternatively, or additionally, the stopping condition may be a maximum number of iterations, e.g., about 15. In some variations, iteratively updating the map of pixel tumor likelihood values $$CTV^i_{likelihood}(r)$$

for the next iteration i=i+1 may comprise adjusting the map of pixel tumor likelihood values $$CTV^i_{likelihood}(r)$$

by generating an updated map of pixel tumor probability values CTVmask$^i$ by assigning pixels within the shifted tumor contour a high tumor-probability value and assigning pixels outside the shifted tumor contour a low tumor-probability value, calculating $$\sigma^{i-1}_{sig}$$

over the pixels within the shifted tumor contour, calculating $$\mu^{i-1}_{bck}, \sigma^{i-1}_{bck}$$

a over the pixels outside the shifted tumor contour but within the BTZ contour, calculating updated tumor-likelihood values $$\mathcal{L}^i_{sig}(r) = \left(1 + e^{-\frac{\left(Act(r)-\mu^{i-1}_{sig}\right)}{\sigma^{i-1}_{sig}}}\right)^{-1};$$

calculating updated background-likelihood values $$\mathcal{L}^i_{bck}(r) = \left(1 + e^{-\frac{\left(\mu^{i-1}_{bck} Act(r)\right)}{\sigma^{i-1}_{bck}}}\right)^{-1}$$

and adjusting the map of pixel tumor likelihood values $$CTV^{i+1}_{likelihood}(r)$$

using the updated map of pixel tumor probability values CTVmask$^i$, updated tumor-likelihood values $$\mathcal{L}^i_{sig}(r),$$

and updated background-likelihood values $$\mathcal{L}^i_{bck}(r).$$

Described herein are methods for tracking a target region. One variation of a method for tracking a target region may comprise acquiring PET imaging data of a target region, identifying, using the acquired PET imaging data, a location of the target region, determining whether the location of the target region is within a target region contour, and generating a notification if the location of the target region is outside a target region contour. The target region contour may be a biology-tracking zone (BTZ) contour and/or a planning target volume (PTV) contour. Identifying the location of the target region may comprise using a tumor identification (ID) profile. A tumor ID profile may comprise a plurality of identification parameters that characterize a target region (e.g., contour data, imaging criteria and/or dose criteria, firing filters, etc.). Alternatively, or additionally, identifying the location of the target region may comprise generating a map of pixel tumor likelihood values by calculating a tumor-likelihood value and background-likelihood value for each pixel of the PET imaging data and identifying the location of the target region by shifting a tumor contour within the PET imaging data to a centroid location of the map of pixel tumor likelihood values. For example, identifying the location of the target region may comprise using an expectation-maximization (EM) method that iteratively shifts the location of the target region in the initial image to an updated location using subsequently-acquired imaging data (as described further below. In some variations, the method may comprise generating an interlock to stop radiation delivery if the location of the target region is outside the target region contour. Determining whether the location of the target region is within a target region contour may comprise determining whether any portion of the target region is outside the target region contour, and the method may further comprise generating an interlock to stop radiation delivery if any portion of the target region is outside the target region contour. The notification may be a graphical representation that comprises the location of the target region and the target region contour, and the method may further comprise outputting the graphical representation to a display device. Alternatively, or additionally, the notification may be an audible alert, and the method may further comprise outputting the audible alert to a speaker device.

Also described herein are methods for analyzing a dose distribution to a target region by generating a bounded dose volume histogram (bDVH) based on gamma criteria comprising a distance-to-agreement (DTA) criterion and a dose difference (DD) criterion. One example of a method for generating a bounded dose volume histogram (bDVH) based on gamma criteria comprising a distance-to-agreement (DTA) criterion and a dose difference (DD) criterion may comprise generating a $D_{min}$ dose distribution from a planned dose distribution based on the DTA criterion and/or the DD criterion of the gamma criteria, generating a $D_{max}$ dose distribution from the planned dose distribution based on the DTA criterion and/or the DD criterion of the GI, and generating a bounded DVH comprising a lower bound and an upper bound, wherein the lower bound comprises a minimum DVH ($DVH_{min}$) calculated from the $D_{min}$ dose distribution and the upper bound comprises a maximum DVH ($DVH_{max}$) calculated from the $D_{max}$ dose distribution. Further examples and variations of methods for analyzing a dose distribution to a target region by generating a bounded dose volume histogram (bDVH) based on gamma criteria comprising a distance-to-agreement (DTA) criterion and a dose difference (DD) criterion are described below.

In one variation, a method for generating a bounded dose volume histogram (bDVH) based on gamma criteria comprising a distance-to-agreement (DTA) criterion and a dose difference (DD) criterion may comprise generating a $D_{min}$ dose distribution from a planned dose distribution based on the DTA criterion and/or the DD criterion of the gamma criteria, generating a $D_{max}$ dose distribution from the planned dose distribution based on the DTA criterion and/or the DD criterion of the GI, and generating a bounded DVH comprising a lower bound and an upper bound, wherein the lower bound comprises a minimum DVH ($DVH_{min}$) calculated from the $D_{min}$ dose distribution and the upper bound comprises a maximum DVH ($DVH_{max}$) calculated from the $D_{max}$ dose distribution. Generating the $D_{min}$ dose distribution may comprise calculating, for each point in the planned dose distribution, a minimum dose value that meets the DTA criterion and DD criterion at that point, and generating the $D_{max}$ dose distribution may comprise calculating, for each point in the planned dose distribution, a maximum dose value that meets the DTA criterion and DD criterion at that point. Calculating the minimum dose value at each point and calculating the maximum dose value at each point may comprise using a gradient descent method. For example, calculating the minimum dose value at each point may comprise calculating a 3-D dose gradient at a point, determining a direction of a maximum negative dose gradient, and calculating the minimum dose value at the point by finding a dose value that is at a DTA criterion distance away from the point along the direction of the maximum negative dose gradient. Calculating the maximum dose value at each point may comprise calculating a 3-D dose gradient at a point, determining a direction of a maximum positive dose gradient, and calculating the maximum dose value at the point by finding a dose value that is at a DTA criterion distance away from the point along the direction of the maximum positive dose gradient. In some variations, generating the $D_{min}$ dose distribution may comprise calculating, for each point in the planned dose distribution, a minimum dose value $DTA_{min}$ such that a gamma index (GI) value at that point meets a passing standard value, calculating, for each point in the planned dose distribution, a minimum dose value $DD_{min}$ such that the GI value at that point meets the passing standard value, and generating the $D_{min}$ dose distribution by taking the minimum of the $DTA_{min}$ and $DD_{min}$ values for each point in the planned dose distribution:

$$D_{min} = \min(DTA_{min}, DD_{min}).$$

Generating the $D_{max}$ dose distribution may comprise calculating, for each point in the planned dose distribution, a maximum dose value $DTA_{max}$ such that the GI value at that point meets the passing standard value, calculating, for each point in the planned dose distribution, a maximum dose value $DD_{max}$ such that the GI value at that point meets the passing standard value, and generating the $D_{max}$ dose distribution by taking the maximum of the $DTA_{max}$ and $DD_{max}$ values for each point in the planned dose distribution:

$$D_{max} = \min(DTA_{max}, DD_{max}).$$

In some variations, the passing standard value may be less than or equal to 1.

Alternatively, or additionally, in some variations, calculating the minimum dose value $DTA_{min}$ for a point in the planned dose distribution may comprise determining a minimum dose value at locations in the planned dose distribution that are at a DTA criterion distance from the point. Calculating the maximum dose value $DTA_{max}$ for a point in the planned dose distribution may comprise determining a maximum dose value at locations in the planned dose distribution that are at a DTA criterion distance from the point.

Gamma-derived bDVHs may be used to select gamma criteria values for treatment plan evaluation and/or dose delivery quality assurance. One variation of a method may comprise generating a treatment plan bounded dose volume histogram (bDVH) based on a treatment plan fluence map and a selected dose variability (e.g., for a region of interest), generating a 3-D dose distribution based on the treatment plan fluence map, generating a plurality of bDVHs that are each derived from different gamma criteria values for the 3-D dose distribution, identifying a bDVH from the plurality of gamma-derived bDVHs that fits within boundaries of the treatment plan bDVH, and selecting the gamma criteria values associated with the identified bDVH for evaluating the treatment plan. Generating a treatment plan bDVH may comprise calculating a lower bound curve based on the lowest acceptable dose for a region of interest and calculating an upper bound curve based on the highest acceptable dose for the region of interest. The lowest acceptable dose and the highest acceptable dose may be calculated from the selected dose variability. Generating a 3-D dose distribution may comprise calculating a dose value for each voxel in a region of interest (e.g., target region, entire patient body, etc.) using the treatment plan fluence map and an image of the region of interest. Generating a bDVH derived from gamma criteria values may comprise calculating a lower bound curve based on a $D_{min}$ dose distribution and an upper bound curve based on a $D_{max}$ dose distribution, where $D_{min}$ and $D_{max}$ are calculated based on the DTA criterion and DD criterion of a gamma criteria. This may be repeated to generate a plurality of bDVHs for a plurality of gamma criteria values. Generating the plurality of gamma-derived bDVHs may comprise generating a family of bDVHs that have at least one gamma criterion value in common. The gamma criteria values may include combinations of a distance-to-agreement (DTA) value of 1 mm, 2 mm, 3 mm with a dose difference (DD) value of 1%, 2%, 3%. In some variations, the method may further comprise generating a graphical representation of the plurality of gamma-derived bDVHs and outputting the graphical representation to a display device.

One variation of a method for selecting gamma criteria values may comprise generating a treatment plan bounded dose volume histogram (bDVH) based on a treatment plan fluence map and a selected dose variability, generating a 3-D dose distribution based on the treatment plan fluence map, generating a bDVH from selected gamma criteria values for the 3-D dose distribution, determining whether the gamma-derived bDVH fits within the boundaries of the treatment plan bDVH, and if the gamma-derived bDVH fits within the boundaries of the treatment plan bDVH, selecting the gamma criteria associated with the bDVH for evaluating the treatment plan. Generating a treatment plan bDVH may comprise calculating a lower bound curve based on the lowest acceptable dose for a region of interest and calculating an upper bound curve based on the highest acceptable dose for the region of interest. The lowest acceptable dose and the highest acceptable dose may be calculated from the selected dose variability. Generating a 3-D dose distribution may comprise calculating a dose value for each voxel in a region of interest (e.g., target region, entire patient body, etc.) using the treatment plan fluence map and an image of the region of interest. Generating a bDVH derived from gamma criteria values may comprise calculating a lower bound curve based on a $D_{min}$ dose distribution and an upper bound curved based on a $D_{max}$ dose distribution, where $D_{min}$ and $D_{max}$ are calculated based on the DTA criterion and DD criterion of a gamma criteria. This may be repeated to generate a plurality of bDVHs for a plurality of gamma criteria values. If the gamma-derived bDVH does not fit within the boundaries of the treatment plan bDVH, the method may further comprise iterating on gamma criteria values until a gamma-derived bDVH fits within the boundaries of the treatment plan bDVH. The selected gamma criteria values may include combinations of a distance-to-agreement (DTA) value of 1 mm, 2 mm, 3 mm with a dose difference (DD) value of 1%, 2%, 3%. In some variations, the method may comprise generating a graphical representation of each of the generated gamma-derived bDVHs and outputting the graphical representation to a display device.

BRIEF DESCRIPTION OF THE DRAWINGS

FIG. 3A depicts a flowchart representation of one variation of a method for generating a tumor ID profile.

FIGS. 3B-3D depict examples of tumor ID profiles.

FIG. 4A depicts a flowchart representation of one variation of a method for generating a bDVH based on gamma criteria.

FIG. 4C depicts a flowchart representation of one variation of a method for generating a bDVH based on gamma criteria.

FIG. 4D depicts a flowchart representation of one variation of a method for calculating $DTA_{min}$ and $DTA_{max}$ for each point in a dose distribution.

FIG. 4E depicts a flowchart representation of one variation of a method for generating a bDVH based on gamma criteria values.

FIGS. 5A and 5B depict a flowchart representation of one variation of a method for locating a tumor based on an initial image and newly-acquired imaging data.

FIG. 6A depicts a flowchart representation of one variation of a method for identifying the location of a target region using a tumor ID profile.

FIG. 6C depicts a flowchart representation of one variation of a method for calculating the PET tracer concentration within a target region contour.

FIG. 6D depicts a flowchart representation of one variation of a method for identifying candidate regions in an image by calculating dose metric values and comparing them to dose metric criteria of a tumor ID profile.

FIG. 6E depicts a flowchart representation of one variation of a method for identifying candidate regions in an image by calculating a DVH for the candidate region and comparing the DVH to a DVH criterion of a tumor ID profile.

FIG. 7A depicts a flowchart representation of one variation of a method for evaluating the safety of continued radiation delivery to a target region using its tumor ID profile.

FIG. 10A depicts a flowchart representation of one variation of a method of using gamma-derived bDVHs for selecting gamma criteria values for treatment plan quality assurance (QA).

DETAILED DESCRIPTION

Figure 1:
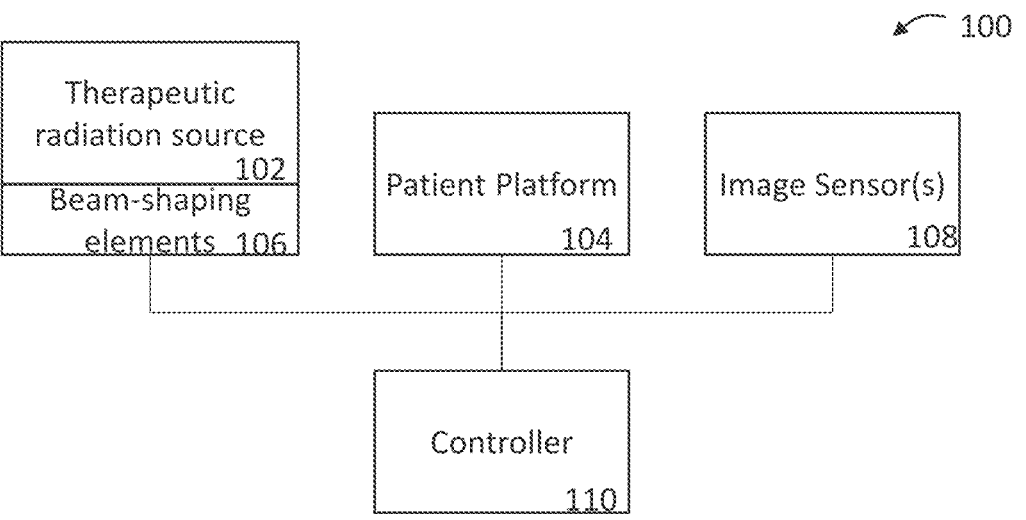
FIG. 1 depicts a block diagram representation of one variation of a radiotherapy system.

Described herein are systems and methods for identifying the location of a target region during a radiotherapy session and evaluating the safety of continued delivery of radiation to the target region.

Also described herein are methods for generating and using bounded dose volume histograms (bDVHs) derived from gamma criteria. One variation of a method of using a gamma-derived bDVH may comprise generating a plurality of bDVHs from different gamma criteria values for a planned dose distribution, identifying the gamma-derived bDVHs that have an acceptable range of dose variability (e.g., within a treatment plan bDVH), and selecting the gamma criteria associated with the identified bDVHs for evaluating the treatment plan. The gamma-derived bDVHs may be generated for target regions and/or organs at risk (OARs). These methods may facilitate the selection of gamma criteria values that represent clinical dose objectives for evaluating (e.g., in a quality assurance procedure) how well a delivered dose matches a treatment plan dose.

The methods described herein may be used with any external beam radiation therapy, such as intensity modulated radiation therapy (IMRT) and stereotactic body radiation therapy (SBRT). These methods may also be used with biology-guided radiation therapy (BgRT), where radiation fluences are calculated based on limited-time sampled (LTS) PET imaging data acquired (by PET detectors integrated with the radiotherapy system) during the treatment session and rapidly delivered to the patient. On the day of treatment, the patient may be injected with a PET tracer that preferentially accumulates at tumor sites. The LTS PET imaging data may be masked by a biology targeting zone (BTZ) and then convolved with shift invariant firing filters generated during treatment planning to calculate the radiation fluence for delivery. The BTZ is a region (e.g., a volume) that may be defined by a clinician as the region from which PET imaging data is used to calculate the radiation fluence for delivery. In some variations, the BTZ may be a spatial mask (e.g., a bitmask that corresponds to a spatial location defined by a clinician) or filter that may be applied to PET imaging data to select the PET imaging data that may be used to calculate the radiation fluence for delivery. For example, a BTZ volume may include the gross tumor volume, planning target volume, and/or a motion envelope of the target region. Firing filters are a mapping or transformation (e.g., a transformation matrix) that designates the conversion of imaging data into a radiation fluence that when delivered, provides the desired dose to the target region. In some variations, the radiation fluence may be a fluence map that includes radiation beamlet pattern(s) and/or beamlet intensities that may be emitted to provide a prescribed dose. The shift invariant firing filters are generated during treatment planning based on planning PET images in conjunction with the clinician prescriptions. The firing filters represent a transformation from an image (or from the image space) to a fluence (or to fluence space). PET imaging data acquired over short time periods (e.g., less than 5 seconds, less than 3 seconds, less than 1 second, less than 0.5 second, etc.) often do not contain enough data for a target region to be identified by visual inspection, but do contain sufficient information for a partial fluence to be calculated rapidly. Convolving the LTS PET imaging data with shift invariant firing filters (which were calculated based on a more complete planning PET image) converts the "partial" PET image into a "partial" fluence that can be delivered to the target region before its location changes. Over the course of an entire treatment session, these partial fluences sum together and result in the delivery of the prescribed dose. Since the shift invariant firing filters represent a mapping between PET imaging data and radiation fluence (and by extension, when combined with anatomical data, radiation dose), a radiotherapy system may be configured to predict the radiation fluence and/or dose that may be delivered to the patient based on PET imaging data acquired during a PET pre-scan (e.g., taken just prior to radiation delivery). This may facilitate in the evaluation of whether a target region, at the start of a treatment session, has the appropriate PET tracer accumulation properties that would result in the safe and complete delivery of the prescribed radiation dose.

Radiotherapy System Overview

The methods described herein may be used with various radiotherapy systems. FIG. 1 depicts a functional block diagram of a variation of a radiotherapy system that may be used with one or more of the methods described herein. Radiotherapy system (100) comprises one or more therapeutic radiation sources (102) and a patient platform (104). The therapeutic radiation source may comprise an X-ray source, electron source, proton source, and/or a neutron source. For example, a therapeutic radiation source (102) may comprise a linear accelerator (linac), Cobalt-60 source, and/or an X-ray machine. The therapeutic radiation source may be movable about the patient platform so that radiation beams may be directed to a patient on the patient platform from multiple firing positions and/or angles. In some variations, a radiotherapy system may comprise one or more beam-shaping elements and/or assemblies (106) that may be located in the beam path of the therapeutic radiation source. For example, a radiotherapy system may comprise a linac (102) and a beam-shaping assembly (106) disposed in a path of the radiation beam. The beam-shaping assembly may comprise one or more movable jaws and one or more collimators. At least one of the collimators may be a multi-leaf collimator (e.g., a binary multi-leaf collimator, a 2-D multi-leaf collimator, etc.). The linac and the beam-shaping assembly may be mounted on a gantry or movable support frame that comprises a motion system configured to adjust the position of the linac and the beam-shaping assembly. In some variations, the linac and beam-shaping assembly may be mounted on a support structure comprising one or more robotic arms, C-arms, gimbals, and the like. The patient platform (104) may also be movable. For example, the patient platform (104) may be configured to translate a patient linearly along a single axis of motion (e.g., along the IEC-Y axis), and/or may be configured to move the patient along multiple axes of motion (e.g., 2 or more degrees of freedom, 3 or more degrees of freedom, 4 or more degrees of freedom, 5 or more degrees of freedom, etc.). In some variations, a radiotherapy system may have a 5-DOF patient platform that is configured to move along the IEC-Y axis, the IEC-X axis, the IEC-Z axis, as well as pitch and yaw.

In the variation shown in FIG. 1, the radiotherapy system (100) also comprises a controller (110) that is in communication with the therapeutic radiation source (102), beam-shaping elements or assemblies (106), patient platform (104), and one or more image sensors (108) (e.g., one or more imaging systems). The controller (110) may comprise one or more processors and one or more machine-readable memories in communication with the one or more processors, which may be configured to execute or perform any of the methods described herein. The one or more machine-readable memories may store instructions to cause the processor to execute modules, processes and/or functions associated with the system, such as one or more treatment plans, tumor identification (ID) profiles for the target regions, the calculation of radiation fluence maps based on treatment plan and/or clinical goals, segmentation of fluence maps into radiotherapy system instructions (e.g., that may direct the operation of the gantry, therapeutic radiation source, beam-shaping assembly, patient platform, and/or any other components of a radiotherapy system), iterative calculations for updating the location(s) of a target region, and image and/or data processing associated with treatment planning and/or radiation delivery. In some variations, the memory may store treatment plan data (e.g., treatment plan firing filters, fluence map, planning images, treatment session PET pre-scan images and/or initial CT, MRI, and/or X-ray images), target ID profile(s), instructions for identifying the location of a target region using newly-acquired imaging data, and instructions for delivering the derived fluence map (e.g., instructions for operating the therapeutic radiation source, beam-shaping assembly and patient platform in concert). The controller of a radiotherapy system may be connected to other systems by wired or wireless communication channels. For example, the radiotherapy system controller may be in wired or wireless communication with a radiotherapy treatment planning system controller such that fluence maps, firing filters, tumor ID profiles, initial and/or planning images (e.g., CT images, MRI images, PET images, 4-D CT images), patient data, and other clinically-relevant information may be transferred from the radiotherapy treatment planning system to the radiotherapy system. The delivered radiation fluence, any dose calculations, and any clinically-relevant information and/or data acquired during the treatment session may be transferred from the radiotherapy system to the radiotherapy treatment planning system. This information may be used by the radiotherapy treatment planning system for adapting the treatment plan and/or adjusting delivery of radiation for a successive treatment session. Additional description of radiotherapy systems will be provided below.

Methods Overview

The methods described herein may comprise identifying the location of a target region using imaging data and a tumor identification profile (which may be referred to as a "tumor ID profile", an "ID profile", or a "tumor profile"). In some variations, the identified location of the target region may be compared with the boundaries of selected volumes or regions (e.g., the planning target volume, the gross tumor volume, the biology-targeting zone, motion envelope, etc.), and if the target region location is outside of the boundaries or any pre-specified safety margins (whether inside or outside of the boundaries), the controller may generate a notification that the target region has moved substantially. The controller of a radiotherapy system may store the tumor ID profiles for all of the target regions to be treated during a treatment session and may be configured to determine the location of the target regions using the acquired imaging data and tumor ID profiles. A tumor ID profile may comprise a plurality of identification parameters that, when taken together, characterize a target region. Examples of identification parameters may include, but are not limited to, contour data that specifies the 2-D or 3-D boundaries of the target region (and any associated regions of interest), imaging and/or dose criterion that have been derived based on imaging data (e.g., anatomical imaging data and/or functional imaging data) and firing filters calculated based on a prescribed dose to target region. In some variations, identification parameters of a tumor profile for a particular target region may comprise a PET data criterion, a dose metric criterion, the target region contour, and a biology-targeting zone (BTZ) contour. The identification parameters of a tumor ID profile may be used to distinguish (e.g., disambiguate) target regions from each other. This may be particularly desirable for the treatment of metastatic disease so that the prescribed dose for a given tumor is precisely delivered to that tumor. A PET data criterion may be a threshold or standard value for evaluating PET data, for example, to determine whether a region of a PET image is likely to be part of the target region or not. A dose metric criterion may be a threshold or standard value for evaluating a dose distribution, for example, to determine whether the dose to a region of an image (e.g., PET image) is likely to be part of the target region or not. A radiotherapy system may use newly-acquired imaging data in conjunction with the tumor ID profile to identify the location of a target region at the start of a treatment session, and optionally, throughout the treatment session. The location of a target region using a tumor ID profile may be identified automatically after the desired quantity of imaging data has been acquired, and may be, in some variations, updated at predetermined intervals or timepoints during a treatment session Imaging data may be acquired on the day of treatment, hours or minutes before a treatment session, and/or during the treatment session. Frequently refreshing the imaging data and confirming (e.g., reconfirming) the location of a target region at the start of (and optionally throughout) a treatment session may help the radiotherapy system deliver therapeutic radiation to the actual location of the target region, and improve the safety of radiotherapy delivery by limiting irradiation of surrounding healthy tissue. In some examples, the location of the target region as identified by the tumor ID profile may be monitored one or more times throughout a treatment session to confirm that the target region remains within a pre-defined region, e.g., within the BTZ, and/or within specified safety margins of the boundaries of the pre-defined region.

In some variations, one or more target regions may be irradiated using BgRT, where shift invariant firing filters calculated during BgRT planning are convolved with newly-acquired imaging data during treatment to calculate the delivery fluence and generate a predicted delivery dose distribution. Characteristics of the predicted delivery dose distribution represented by dose metric values may be compared with dose metric criteria of a target region to identify its location and/or determine whether it is safe to proceed with radiation delivery. A dose metric value may be an expected delivered dose calculated from the PET data. For example, a dose metric value may be calculated from a fluence map generated from convolving the firing filters with imaging data, and an anatomical image. A dose metric criterion may be a threshold or standard value for evaluating a dose distribution to a region of an image (e.g., PET image), for example, to determine whether the region is likely to be part of the target region or not. The dose metric criteria of the tumor ID profile for a target region may be defined based on the planned dose distribution (which is a synthesis of planning imaging data and the shift invariant firing filters for a target region). In some variations, during treatment planning, dose metric criterion or criteria may be calculated for the planned dose distribution. Since the planned dose distribution reflects characteristics of the imaging data of a target region, the dose metric criterion or criteria may be used to help identify the target region during a treatment session. For example, during treatment planning, the planned dose distribution for a target region may have an associated DVH and/or gamma index (GI) value, which may be part of the target region's ID profile. At the time of treatment delivery, imaging data may be acquired of the target region and convolved with the shift invariant firing filters to calculate a fluence map from which the delivery dose distribution is derived. A DVH and/or GI value may be calculated for the delivery dose distribution and compared with the corresponding dose metric criteria of the tumor ID profile. If there is a significant deviation (e.g., outside of tolerance thresholds or safety margins) between the DVH and/or GI value of the delivery dose distribution and the planned dose distribution, the operator may decide not to proceed with radiation delivery to the target region. Alternatively, or additionally, a significant deviation may indicate that the target region has moved (i.e., changed its location) and that its location needs to be updated. In some variations, the updated location may be compared to pre-defined regions or volumes to determine whether the location change is acceptable and safe for continued treatment. For example, some methods may include determining whether the updated location is within the BTZ and if a substantial portion of the target region is not within the BTZ (e.g., a threshold proportion of the target region is outside the BTZ), a notification may be generated and optionally, radiation delivery may be stopped. The radiotherapy system may use any of the methods described herein to update the location of the target region, re-calculate the delivery dose distribution and the corresponding dose metric criteria based on the updated location. The updated DVH and/or GI value may be compared with the tumor ID profile to determine whether the updated target region location is correct and/or whether it would be safe to proceed with radiation delivery.

Figure 2:
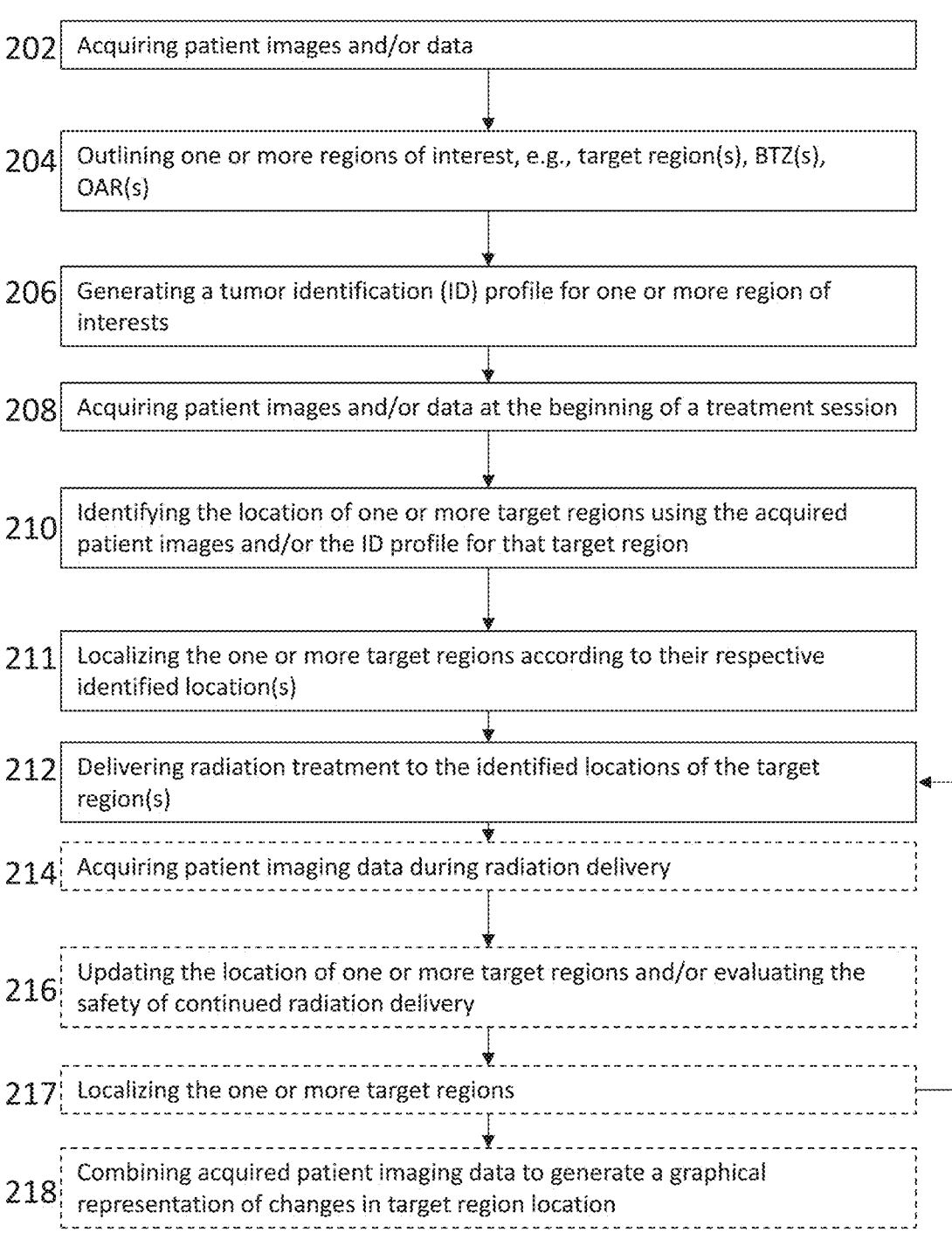
FIG. 2 depicts a flowchart representation of one variation of a method for delivering treatment radiation to a target region using an identification (ID) profile.

FIG. 2 depicts a flowchart representation of one variation of a method for delivering treatment radiation to a target region using an ID profile that characterizes the target region. The method (200) may be used to deliver radiation to one target region (e.g., a single tumor) or multiple target regions (e.g., multiple tumors or metastases). Method (200) may comprise acquiring (202) patient images and/or data, outlining (204) one or more regions of interest, and generating (206) a tumor ID profile for each of the regions of interest. The contours of the region of interest may include one or more of the gross tumor volume (GTV), clinical target volume (CTV), planning target volume (PTV), and the like. In some variations where PET tracer-based biology-guided radiation therapy (BgRT) may be used, outlining (204) regions of interest may also comprise outlining a biology tracking zone (BTZ), which may be a spatial mask or filter that is configured to be applied to imaging data comprising positron annihilation emission data (also referred to as lines-of-response or LOR data). The generated tumor ID profile may comprise identification parameters including the contour information and imaging criterion derived from the acquired patient images and/or data. For example, method (200) may comprise acquiring (202) patient CT images and PET images of a target region. The identification parameter of the target region ID profile may comprise PET data criterion (e.g., standard uptake value or SUV metric values) and/or CT data criterion (e.g., attenuation values). In some variations, an identification parameter may comprise a dose metric criterion that specifies the dose deliverable to the target region based on the acquired imaging data and a clinician's prescription.

Method (200) may comprise acquiring (208) patient images and/or data at the beginning of a treatment session, identifying (210) the location of one or more target regions using the acquired patient images and/or data and the ID profile for that target region, localizing (211) the one or more target regions, and delivering (212) radiation treatment to the identified locations of the target regions. Examples of patient images may include, but are not limited to, MR images, CT images, PET images, ultrasound images, and the like. The acquired images may be limited-time sample images, which may be a reconstruction of imaging data acquired over a short time period and may have higher levels of noise than a diagnostic-quality image. Acquiring (208) patient images may comprise acquiring a set of imaging data such as positron annihilation emission or LOR data using a PET detectors, X-ray projection data using X-ray detectors, sub-samples in k-space from an MR imaging pulse sequence using MRI sensors.

In some variations, identifying (210) the location of a target region may comprise iterating on an initial image of the target region using the newly-acquired imaging data to generate an image that depicts the target region at its updated location. One example of an iterative method is based on Bayesian statistics. This method may comprise an expectation-maximization (EM) method which iteratively shifts the location of the target region in the initial image (e.g., an image that was used during treatment planning) to an updated location using subsequently-acquired imaging data. Variations of this method will be described further below.

In some variations, identifying (210) a target region using its ID profile may comprise determining whether the delivering radiation to the target region is "safe", i.e., the anticipated delivered dose is within clinically-acceptable or prescribed bounds and will not expose surrounding tissue to dose levels that exceed safety thresholds. Alternatively, or additionally, delivering radiation to the target region may be deemed as safe for continued radiation delivery if the target region is located within the PTV, GTV, CTV, and/or BTZ (for BgRT). In some variations, identifying (210) a target region may comprise calculating dose metric values based on the acquired imaging data, and may include dose metrics such as a mean dose amount, a maximum dose amount, and/or a minimum dose amount within any of the defined contours, gamma metrics, a dose-volume histogram (DVH) for the target region, and/or an expected delivery dose volume, etc. A dose metric value may be an expected delivered dose calculated from the PET data. A dose metric criterion may be a threshold or standard value for evaluating a dose distribution to a region of an image (e.g., PET image), for example, to determine whether the region is likely to be part of the target region or not. The expected delivery dose volume represents the 3-D radiation dose to the entire patient volume that results from irradiating the one or more target regions. In some variations, the expected delivery dose volume may be a 3-D matrix (e.g., over the volume of the patient) where each entry represents the dose to that voxel. The dose metric value(s) calculated from the acquired imaging data and planned firing filters (e.g., by convolving the acquired imaging data with the firing filters) may be compared with the corresponding dose metric criterion (or criteria) of the ID profile, and if the dose metric value(s) meet the dose metric criterion/criteria, then the target region may be determined to be safe to treat. The controller may be configured to indicate that the location of a target region has been identified only if it is safe to deliver radiation to the target region at that location.

Optionally, after identifying the location of the one or more target regions, method (200) may comprise updating the criteria of the identification parameters to account for the actual value of the metric values as calculated from the acquired imaging data. For example, the dose metric criterion/criteria of the ID profile may be adjusted based on the calculated dose metric value(s). In some variations, the PET data criterion/criteria of the ID profile may be adjusted based on the acquired patient images (e.g., a PET pre-scan at the beginning of the treatment session). The updated metric criterion/criteria of the ID profile may be used for safety monitoring during the treatment session.

Localizing (211) the target region(s) may comprise adjusting the patient's position and/or the delivery fluence so that the planned radiation is directed to the current location of the target region(s). In some variations, localizing (211) a target region may comprise moving the patient and/or the patient platform to align the target region location with its location during treatment planning. This may be referred to as a "physical localization" because it involves adjusting the patient on the patient platform and/or moving the patient platform itself. Alternatively, or additionally, localizing (211) a target region may comprise adjusting the radiation fluence for delivery so that radiation is delivered to the current, actual location of the target region. This may not require the physical adjustment of the patient and/or patient platform and may be referred to as a "virtual localization". Conceptually, virtual localization shifts the planned radiation (e.g., planned fluence map) to align with the current location of the target region. In some variations, shifting a planned fluence map may comprise calculating a localization function based on the identified location, and applying the localization function to firing filters that were calculated during treatment planning. The resulting delivery fluence map reflects the current location of the target region. For treatment sessions that irradiate target regions using BgRT, localizing (211) a BgRT target region may comprise shifting the BTZ of the target region according to the location difference between the identified target region location and its location during treatment planning Virtual localization does not require physical manipulation of the patient or patient platform adjustments, but instead generates the delivery fluence map using the radiotherapy system controller processor. As such, virtual localization may help facilitate the treatment session workflow by reducing the number of times a technician enters the treatment bunker to physically move the patient on the platform. In some variations, localizing target regions at the beginning of a treatment session may comprise a physically localizing a first target region and a virtually localizing a second target region. This may facilitate and expedite the irradiation of multiple target regions, since a physical localization would not be required for each target region.

Method (200) may optionally comprise acquiring (214) additional patient imaging data during radiation delivery and updating (216) the location of the target region(s). Optionally, after updating (216) the location of the target region(s), the target region(s) may be re-localized (217). The re-localization may be a physical localization or a virtual localization. In some variations, a treatment session may include a physical re-localization for one or more target regions and a virtual re-localization for the other one or more target regions. The additional patient imaging data may be used to evaluate whether it is safe to continue delivering radiation to the target region(s). In some variations, metric values (e.g., tracer uptake values, dose values) derived from the acquired imaging data may be compared with the corresponding identification parameters of a target region to determine whether the location of the target region has changed and/or whether it is safe to continue delivering radiation to the target region. In some variations, the metric values from the acquired imaging data may be compared with the identification parameters that were updated at the start of the treatment session. For example, PET data criteria of a tumor ID profile may be updated based on a PET pre-scan taken at the start of the treatment session, and the updated PET data criteria may be used for safety monitoring and/or to determine whether the target region has changed its location. Alternatively, or additionally, method (200) may comprise generating an image of the updated location of the target region by iteratively updating the image of the previous location of the target region using the additional patient imaging data. The radiotherapy system may update (216) the location of the target region(s) and/or evaluate the safety of continued radiation delivery and/or re-localize the target region(s) repeatedly throughout the treatment session. For example, the location update and/or safety evaluation may occur based on operator commands (e.g., asynchronously or "on-demand"), and/or at predetermined time intervals during radiation delivery. Some treatment sessions may involve moving the patient through the radiation treatment plane (e.g., as defined by the collimation assembly) multiple times, where each sweep of the patient through the treatment plane is a shuttle pass. The target region location update (and optional comparison with the boundaries of a BTZ or other pre-defined volume) and/or safety evaluation may occur between shuttle passes, where the imaging data acquired during a shuttle pass may be used to determine whether to continue radiation delivery in the next shuttle pass, and/or whether to modify radiation delivery in the next shuttle pass so that the delivered dose remains within approved thresholds. In some variations, the updated location of a target region may be compared with the contours of safety margins (e.g., margins around OARs, a BTZ boundary or a shell around a BTZ) and if the target region has moved too close to a safety margin, the radiotherapy system may generate a notification to the operator and/or pause radiation delivery. After the safety evaluation and re-localization, method (200) may comprise continuing to deliver (212) radiation treatment to the target region(s) and optionally, acquiring (214) imaging data during radiation delivery.

Optionally, method (200) may comprise combining (218) the acquired imaging data to generate a graphical representation of the location changes of the target region. The graphical representation may comprise a contour representing the target region that is overlaid on an anatomical image and/or may comprise a collection of arrows or vectors that represent the direction and direction of the location change. In some variations, the graphical representation may include the contours of one or more of the GTV, CTV, PTV, and/or BTZ that corresponds to each target region. The graphical representation may be generated multiple times throughout the treatment session, for example, at the start of the treatment session (e.g., before radiation delivery), at multiple time points during the treatment session (e.g., during radiation delivery), and/or after the treatment session (e.g., after radiation delivery).

Some steps of the method (200) may be performed during treatment planning (e.g., by the treatment planning system) and other steps may be performed during a treatment session (e.g., by the radiotherapy system). For example, acquiring (202) patient images, defining or outlining (204) contours of one or more regions of interest, and generating (206) a tumor ID profile may be performed during treatment planning, while acquiring (208) patient images, identifying (210) the location of a target region, and delivering (212) radiation treatment to the target region at its identified location may be performed during a treatment session. The optional steps of acquiring (214) imaging data during delivery, updating (216) the location of the target region and/or evaluating safety, and combining (218) imaging data to generate a graphical representation of location change(s) during the treatment session may be performed during and/or after a treatment session. The graphical representation may comprise visual indicia that highlights each of the identified regions in the image. In some variations, steps (202)-(212) of method (200) (along with optional stapes (214)-(216)) may be performed during a single session that combines planning and treatment.

Tumor Identification (ID) Profile

Some variations of the methods described herein use a tumor identification (ID) profile to facilitate the detection of a previously-identified target region during a treatment session. A tumor ID profile comprises a plurality of identification parameters that characterize a target region. Identification parameters may include patient anatomical imaging data, functional imaging data, contour data, and/or dose data. In some variations, identification parameters may comprise a set of criteria that may be used to determine the location of a target region in an image. That is, the identification parameters of a tumor profile may be used to evaluate a portion of an image and determine whether the target region is located in that portion of the image. For example, a tumor ID profile may have identification parameters that include PET-based criterion or criteria (e.g., SUV metrics, PET tracer concentration metrics (e.g., PET tracer activity concentration), normalized target signal or NTS, metabolic tumor volume, etc.), dose-based criterion or criteria (e.g., mean dose values, maximum dose values, bounded DVH curves of certain volumes of interest (VOIs), etc.), one or more target region contours (e.g., PTV, CTV, and/or GTV), and a BTZ contour. These criteria may be used to determine the portions of an image (e.g., an image acquired at the time of treatment) that are likely to be the location of the target region. A tumor ID profile may be generated using a variety of patient data and clinician-defined parameters during treatment planning. For example, the identification parameters of a tumor ID profile may be generated from a patient's CT images, PET images (which may be registered to the CT image and/or be in the same frame-of-reference), an outline or contour of the tumor volume (which may be one or more of PTV, GTV, or CTV), and/or an outline or contour of the BTZ. Identification parameters may include patient imaging data (e.g., CT imaging data, MR imaging data, PET imaging data, and/or ultrasound imaging data, etc.) and clinician-defined contours (e.g., PTV, CTV, GTV, and/or BTZ). A tumor ID profile may be defined during a treatment planning session and used to identify the location of a target region using imaging data acquired during a treatment session. Alternatively, or additionally, a tumor ID profile may be defined during an early portion of a single combination session (e.g., a single "scan-plan-treat" session) and used to identify (e.g., update) the location of a target region at a later portion of the session using imaging data acquired in the intervening period. Imaging data acquired at the time of treatment may be used to calculate imaging-based metric values and/or dose metric values, and those metric values may be compared to the corresponding identification parameters of a target region's tumor profile to help identify the location of the target region. The calculated imaging-based metric values and/or dose metric values may be used to determine whether it is safe to deliver radiation to a target region. If it is determined that it is not safe to deliver radiation to the target region at a particular location (i.e., because the target region has moved from that location or is outside of safety margins or pre-defined contours), its tumor ID profile may be used to identify an updated location to which it is safe to continue radiation delivery. Once the updated location is identified, the target region may be re-localized to that updated location and the delivery fluence map may be calculated using the updated location information. Optionally, in some variations, the safety margins and/or pre-defined contours (e.g., the PTV, GTV, CTV, BTZ) may be re-localized to reflect the location change of the target region.

One variation of a method for generating a tumor ID profile is depicted in FIG. 3A. Method (300) may comprise acquiring (302) PET imaging data and CT imaging data, defining (304) contours of a target region and contours of a BTZ, calculating (306) a PET data metric value of the target region, calculating (308) a dose metric value of the target region, and generating (310) a tumor identification profile comprising a plurality of identification parameters that comprise criteria defined based on the PET data metric value and the dose metric value. A PET data metric is a characteristic or parameter that is derived (e.g., directly calculated) from PET data. The value of a PET data metric may be calculated from the PET data acquired by PET detectors. When defining a tumor ID profile, the PET data metric value of the target region may be used to define the PET data criterion/criteria (e.g., the PET data metric value itself may be a PET data criterion). A dose metric value may be an expected delivered dose calculated from the PET data. A dose metric criterion may be a threshold or standard value for evaluating a dose distribution to a region of an image (e.g., PET image), for example, to determine whether the region is likely to be part of the target region or not. When defining a tumor ID profile, the dose metric value of the target region may be used to define the dose metric criterion/criteria (e.g., the dose metric value of the target region may itself be a dose metric criterion). In some variations, the acquired PET and CT imaging data may be "diagnostic quality" images, which are images that contain sufficient information (e.g., reasonable signal-to-noise ratio) and resolution to discern a target region from surrounding tissue. For example, the PET and CT imaging data may be acquired during a diagnostic imaging session or an imaging session as part of the treatment planning workflow. Alternatively, or additionally, imaging data may be acquired at the beginning of a treatment session, for example, the CT imaging data may be acquired for positioning the patient and/or localizing the target region before treatment, and the PET imaging data may be acquired to evaluate whether BgRT is appropriate for the patient. The contours of the target region (e.g., PTV, GTV, CTV) may be delineated based on CT and/or PET images. In some variations, the PET image may be a filtered PET image where the background PET signal may be subtracted or suppressed. The BTZ contour may be larger than the contours of the target region and encompasses the target region. In some variations, the BTZ contour may be sized and shaped to account for positional uncertainties of the patient on the patient platform and/or tumor position within the patient, as well as patient and/or tumor motion, and variabilities in PET tracer uptake by the tumor and surrounding tissue. In some variations, the BTZ contour may be defined manually (e.g., by a clinician), semi-automatically (e.g., a controller may analyze an image and propose candidate contours), and/or automatically (e.g., a controller may define contours with little or no clinician input, referred to as autocontouring). In some variations, a CT image masked by the BTZ may be one of the identification parameters of the ID profile.

PET-based identification parameters may include, for example, a PET image that has been masked by the BTZ (e.g., with the pixels outside of the BTZ set to zero), a metabolic tumor volume (or any PET-based tumor volumes), tumor imaging contrast values, various SUV metrics (e.g., mean SUV, max SUV, min SUV for the target region, normalized SUV for the target region as compared to the BTZ background signal or normalized SUV for the BTZ region as compared to the overall patient background signal, normalized target signal NTS), PET tracer activity concentration AC (having units of kBq/ml), raw or normalized tracer concentration, and the like. The values of the PET data criteria may be calculated from the acquired PET images. For example, the PET data criteria may be calculated from the PET signal or pixel values of the portion of the image that is within the target region contour and/or the PET signal or pixel values of the portion of the image that is outside of the target region contour but within the BTZ contour. In some variations, the SUV metric value may be the ratio of the PET signal (e.g., image pixel values) within the target contour to the PET signal within the BTZ contour but outside the target contour. Alternatively, or additionally, the SUV metric value may be the ratio of the PET signal (e.g., image pixel values) within the BTZ contour to the PET signal outside the BTZ contour. In some variations, a normalized target signal or NTS may be calculated by taking the ratio of the maximum SUV value within the BTZ contour (including the target region) and the mean SUV value within the BTZ contour. In some variations, the NTS may be calculated by calculating the difference between the mean SUV within the target region contour and the mean SUV within the BTZ contour (but outside the target region contour), and taking the ratio of the calculated SUV difference and the SUV outside the BTZ contour. Alternatively, or additionally, the NTS may be calculated by calculating the mean value ($PET_{mean-50\%}$) of all pixels/voxels within the BTZ contour having a pixel/voxel value greater than 50% of the maximum pixel value in the BTZ contour, calculating the mean value ($PET_{mean-bkgnd}$) of the pixels/voxels within a BTZ shell contour that encompasses the BTZ contour, and taking the ratio of the mean values:

$$NTS = \frac{PET_{mean-50\%}}{PET_{mean-bkgnd}}$$

In some variations, the NTS may be a ratio of a mean value ($PET_{mean-80\%}$) of voxels within the BTZ contour having a voxel value greater than 80% of the maximum voxel value in the BTZ contour and a mean value ($PET_{mean-bkgnd}$) of pixels/voxels within a BTZ shell contour that encompasses the BTZ contour:

$$NTS = \frac{PET_{mean-80\%}}{PET_{mean-bkgnd}}$$

In some variations, the NTS may be calculated from the PET tracer activity concentration AC. The PET tracer AC value may represent the net signal value from a target within a BTZ. For example, $$AC = AC^{target} - AC^{Background}$$

Where $AC^{Target}$ may be calculated as the mean-value of the voxels within the BTZ that have a value above 80% (or any X %) of the maximum voxel value within the BTZ (i.e., find the maximum voxel value within the BTZ, calculate the 80% value of that voxel value as the threshold, and calculate the mean of all of the voxels within the BTZ that meet or exceed the threshold), and $AC^{Background}$ is the mean voxel value within the BTZ. The normalized target signal NTS may be a measure of the "signal over the background", and in some variations, may be calculated by normalizing AC by the noise in the background of the BTZ, $$NTS = \frac{AC}{\sigma_{Background}} = \frac{AC^{Target} - AC^{Background}}{\sigma_{Background}}$$

Where $\sigma_{Background}$ may be the standard deviation of the activity concentration values in the shell around the BTZ (i.e., BTZ shell contour).

These identification parameters may be PET-based criteria that a candidate target region should satisfy if it is to be identified as the target region at a different location. For example, an identification parameter may be a minimum threshold value of a NTS, a minimum threshold value of an AC, a minimum tracer concentration value within the target region contour or the BTZ contour, a range of SUV values (maximum and minimum) within the target region contour or the BTZ contour, etc. At the beginning of a treatment session, the identification parameters that comprise PET-based criteria may be updated with the PET imaging data from the PET pre-scan that is conducted before the delivery of therapeutic radiation. The updated criteria may be used during the treatment session for safety and/or location monitoring. For example, an NTS value and AC value may be calculated for a candidate target region just before a treatment session (i.e., at the beginning of a session) and those calculated values may be compared against their respective threshold values, e.g., a threshold NTS value may be about 2 and a threshold AC value may be about 5 kBq/mL. One or both of these threshold values need to be met or exceeded in order for the candidate target region to qualify as the target region. In some variations, the threshold value for the PET-based criteria may differ for treatment plan and treatment delivery, which may account for an expected or acceptable amount of PET signal variation. For example, the threshold NTS value for treatment planning (i.e., must be met prior to treatment planning) may be about 2.7 while the threshold NTS value for treatment delivery (i.e., must be met prior to radiation delivery) may be about 2.

For target regions that may be treated with BgRT, their tumor ID profiles may comprise dose-related identification parameters that may be derived from the PET imaging data, anatomical imaging data (e.g., CT imaging data, MR imaging data), and a prescribed dose. These may be used to calculate shift invariant firing filters, a planned fluence map and to generate a planned dose volume. The planned dose volume represents the radiation dose delivered to the entire patient as a result of irradiating the one or more target regions according to the planned fluence map calculated using the planned firing filters. One or more of the dose-related identification parameters of a tumor ID profile may be derived from the planned dose volume. Examples of dose-related identification parameters may include the volume of the planned dose volume that would be contained within an X % isodose line (where X=100, 80, 50, etc.), DVH plots for the various contours defined in the ID profile, and the mean dose in the planned dose volume, and/or the maximum dose in the planned dose volume. In some variations, an identification parameter may comprise a DVH derived from gamma criteria (referred herein as a gamma-derived bDVH). Methods for generating a bounded DVH based on gamma criteria (which may include a DTA criterion and DD criterion) is described further below. At the beginning of a treatment session, the identification parameters that comprise dose metric criteria may be updated with the imaging data from the imaging data (e.g., CT scan, PET pre-scan) that is acquired before the delivery of therapeutic radiation. The updated dose metric criteria may be used during the treatment session for safety and/or location monitoring.

FIGS. 3B-3D depict examples of tumor ID profiles. FIG. 3B depicts one example of a tumor ID profile for Tumor 1. The tumor ID profile comprises identification parameters that include a target region contour (e.g., PTV contour), a BTZ contour, PET data criteria (i.e., normalized SUV or NTS value, mean SUV value, tracer concentration value (e.g., AC value) for the target region enclosed by the PTV contour), and dose metric criteria (i.e., mean dose value to the target region, minimum dose value to the target region, and mean cumulative or global dose to the patient).

FIG. 3C depicts the tumor ID profile for Tumor 2. The tumor ID profile for Tumor 2 has the same identification parameters the tumor ID profile for Tumor 1 (though with different criteria values and contours) but additionally includes a bounded DVH over the target region. In some variations, the identification parameters of an ID profile may include a bDVH for any VOIs, including OARs and/or the BTZ volume, in addition to or instead of, a bDVH of the target region. A bounded DVH may comprise an upper bound curve and a lower bound curve that define acceptable dose variabilities due to variations in tracer uptake by the target region, target region and/or OAR motion, and/or changes in the target region shape. FIG. 3D depicts the tumor ID profile for Tumor 3. The tumor ID profile has the same identification parameters as the ID profile for Tumor 1, but additionally includes an isodose contour for 120% of the prescribed dose. For a patient with multiple tumors, a tumor ID profile may be generated for each of those tumors, and the tumor ID profiles may have the same types of identification parameters or may have different types of identification parameters. For example, the ID profiles in FIGS. 3B-3D may be for three tumors in one patient. In some variations, all of the criteria represented in the identification parameters of a tumor ID profile need to be met before a tumor location may be identified and/or deemed safe for irradiation. In other variations, only a subset of the criteria needs to be met for a tumor location to be identified and/or deemed safe for irradiation. For example, certain identification parameters may be classified as "high-priority" while other identification parameters may be classified as "low priority", and for a definitive tumor location identification and/or safe-to-treat determination, the criteria of the high-priority identification parameters must be met, but the criteria of the low-priority identification may not be met. Failing any one of the high-priority identification parameter criterion may result in an automatic disqualification of that location as a safe-to-treat location of the target region.

As described above, the identification parameters of the tumor ID profiles depicted in FIGS. 3B-3D may be updated based on the imaging data acquired at the beginning of a treatment session (i.e., before the delivery of therapeutic radiation). For example, after the identification parameters of the tumor ID profile have been used to determine the location of the target region, the PET data metric values calculated from the acquired imaging data may be used to update the PET data criterion/criteria of the tumor ID profile.

Similarly, the dose metric values calculated from the acquired imaging data and the planned firing filters may be used to update the dose metric criterion/criteria of the tumor ID profile. The updated ID parameters (i.e., criterion/criterion) of the tumor ID profile may be used during the treatment session for continued safety and/or location monitoring.

In some variations, method (300) may optionally comprise determining the identification parameters that highlight the differences between two target regions. This may be pertinent to the treatment of metastatic disease, where the radiotherapy system may use tumor ID profiles to distinguish (e.g., disambiguate) one target region from another so that the prescribed dose may be delivered to each region. For example, a method for generating a tumor ID profile may comprise identifying the characteristic(s) of two target regions that differ the most, designate the characteristic(s) as identification parameter(s), and calculate the metric value or criterion for that identification parameter(s). For example, suppose tumor 1 and tumor 2 have similar sizes and shapes (i.e., similar target contours), but differ greatly in their PET uptake characteristics. The ID profile for tumor 1 and tumor 2 may include PET-based identification parameters, and may, for example, have more PET-based identification parameters than anatomical and/or dose-based identification parameters. Selecting identification parameters that emphasize the differences between multiple tumors within a patient may help facilitate disambiguating these tumors during treatment delivery.

Gamma-Derived Bounded Dose Volume Histograms (bDVH)

In some variations, one of the identification parameters may be a dose metric criterion such as a DVH that is generated from gamma criteria of a gamma index (GI). A gamma index is a metric that represents the variability of a dose distribution and is a composite of the distance-to-agreement (DTA) and a percent dose difference (DD) between a reference dose (e.g., desired dose, planned dose) and an actual dose (e.g., optimized dose, dose derived from imaging data, delivery dose). DTA is the nearest distance from a point (e.g., pixel or voxel) on a reference dose distribution to a point (e.g., pixel or voxel) on a test dose distribution having a specific dose level (i.e., specified by percent DD). In some variations, DTA may be the nearest distance from a point on a reference dose distribution to a point of the same dose level on a test dose distribution. Gamma criteria may comprise a DTA criterion (e.g., in a linear dimension with units of mm) and a DD criterion (e.g., a percentage value), for example, 3 mm/3%, 2 mm/2%, 1 mm/1%, etc. A GI value for a particular point (e.g., pixel, voxel) on a reference dose distribution as compared to a test or actual dose distribution (e.g., optimized dose, dose derived from imaging data, delivery dose) may be represented as the minimum value of:

$$\gamma = \sqrt{\left(\frac{DTA}{C_{DTA}}\right)^2 + \left(\frac{DD}{C_{DD}}\right)^2}$$

Where $C_{DTA}$ is the DTA criterion and $C_{DD}$ is the DD criterion. In some variations, the DTA and DD criteria may be selected by a clinician. An acceptable value of the GI (e.g., a passing standard value) may be used to as a threshold to determine whether any point on a dose distribution meets the DTA and DD criteria. In some variations, a passing or acceptable GI value may be less than or equal to 1 (e.g., ≤1, ≤0.5, etc.). The number or proportion (e.g., percentage) of points in a planned dose distribution that have GI values that "pass" (i.e., meet the passing standard value) may be used to determine whether a dose distribution is clinically appropriate and/or safe for delivery.

The gamma criteria (e.g., DD criterion, DTA, criterion) may be the basis of a DVH curve such as a bounded DVH curve that has a lower bound DVH and an upper bound DVH. The lower and upper bounds represent the variability that corresponds with the gamma criteria that would result in a passing or acceptable GI value. That is, a gamma-derived bDVH represents the dose variability that would still result in a dose distribution that meets the passing GI value. The lower bound DVH of a gamma-derived bDVH represents the minimum dose distribution $D_{min}$ that would still meet the gamma criteria and the upper bound DVH of a gamma-derived bDVH represents the maximum dose distribution $D_{max}$ that would still meet the gamma criteria. Since the dose variability may be characteristic of a target region (e.g., in variations where the radiation delivered to a target region is calculated from images of the target region), in some variations, the dose variability may be used in combination with other identification parameters of a tumor profile to identify the location of a target region. The dose variability may be encapsulated in the bDVH. In some variations, the bDVH may be calculated from desired (e.g., clinician-approved) gamma criteria. One variation of a method for generating a bDVH based on gamma criteria is depicted in the flowchart of FIG. 4A. Method (400) may comprise generating (402) a $D_{min}$ dose distribution based on a planned dose distribution and the DTA criterion and/or the DD criterion of a gamma criteria, generating (404) a $D_{max}$ dose distribution based on a planned dose distribution and the DTA criterion and/or the DD criterion of the gamma criteria, generating (406) a minimum DVH by calculating a DVH of the $D_{min}$ dose distribution, generating (408) a maximum DVH by calculating a DVH of the $D_{max}$ dose distribution, and generating (410) a bDVH by setting the minimum DVH as the lower bound, and the maximum DVH as the upper bound. Optionally, the bDVH may comprise a nominal DVH that is the DVH of the planned dose distribution. In some variations, generating (402) the $D_{min}$ dose distribution may comprise calculating, for each point in the planned dose distribution, a minimum dose value that meets the DTA criterion and DD criterion at that point, and generating the $D_{max}$ dose distribution may comprise calculating, for each point in the planned dose distribution, a maximum dose value that meets the DTA criterion and DD criterion at that point. The minimum dose value at a point in a dose distribution may be the lowest dose value that results in a GI index value that meets the passing standard value and the maximum dose value at a point in a dose distribution may be the highest dose value that results in a GI index value that meets the passing standard value.

Another variation of a method for generating a bDVH based on gamma criteria is depicted in the flowchart of FIG. 4E. A bDVH comprises a lower bound DVH and an upper bound DVH, and for a gamma-derived bDVH, the lower and upper bound DVHs represent the range of variability that a dose distribution may have and still meet the gamma criteria from which the bDVH was generated. A method for generating a bDVH derived from gamma criteria may comprise selecting the values of the gamma criteria (e.g., DTA, DD as a percentage), solving for minimum and maximum dose distributions based on each of the gamma criteria and a 3-D dose distribution, generating a maximum dose distribution $D_{max}$ that satisfies the gamma criteria with a 100% passing rate, and generating a minimum dose distribution $D_{min}$ that satisfies the gamma criteria with a 100% passing rate. The DVH for the maximum dose distribution may be calculated (i.e., the maximum DVH) and the DVH for the minimum dose distribution may be calculated (i.e., the minimum DVH). Finally, the gamma-derived bDVH is generated by setting the lower bound to the minimum DVH and setting the upper bound to the maximum DVH. FIG. 4E depicts a flowchart of method (470), which may comprise generating (472) a maximum DD percentage error dose distribution and a minimum DD percentage error dose distribution for a selected DD criterion value, generating (474) a maximum DTA error dose distribution and a minimum DTA error dose distribution for a selected DTA criterion value, generating (476) a $D_{max}$ maximum dose distribution based on the maximum DD percentage error dose distribution and the maximum DTA error dose distribution, generating (478) a $D_{min}$ minimum dose distribution based on the minimum DD percentage error dose distribution and the minimum DTA error dose distribution, generating (480) a maximum DVH by calculating a DVH of the $D_{max}$ dose distribution, generating (482) a minimum DVH by calculating a DVH of the $D_{min}$ dose distribution, and generating (484) a bDVH by setting the minimum DVH as the lower bound, the maximum DVH as the upper bound, and the DVH of the planned dose distribution as the nominal DVH. This bDVH reflects the dose variability permitted while still satisfying the selected DD and DTA criteria.

Figure 4B:
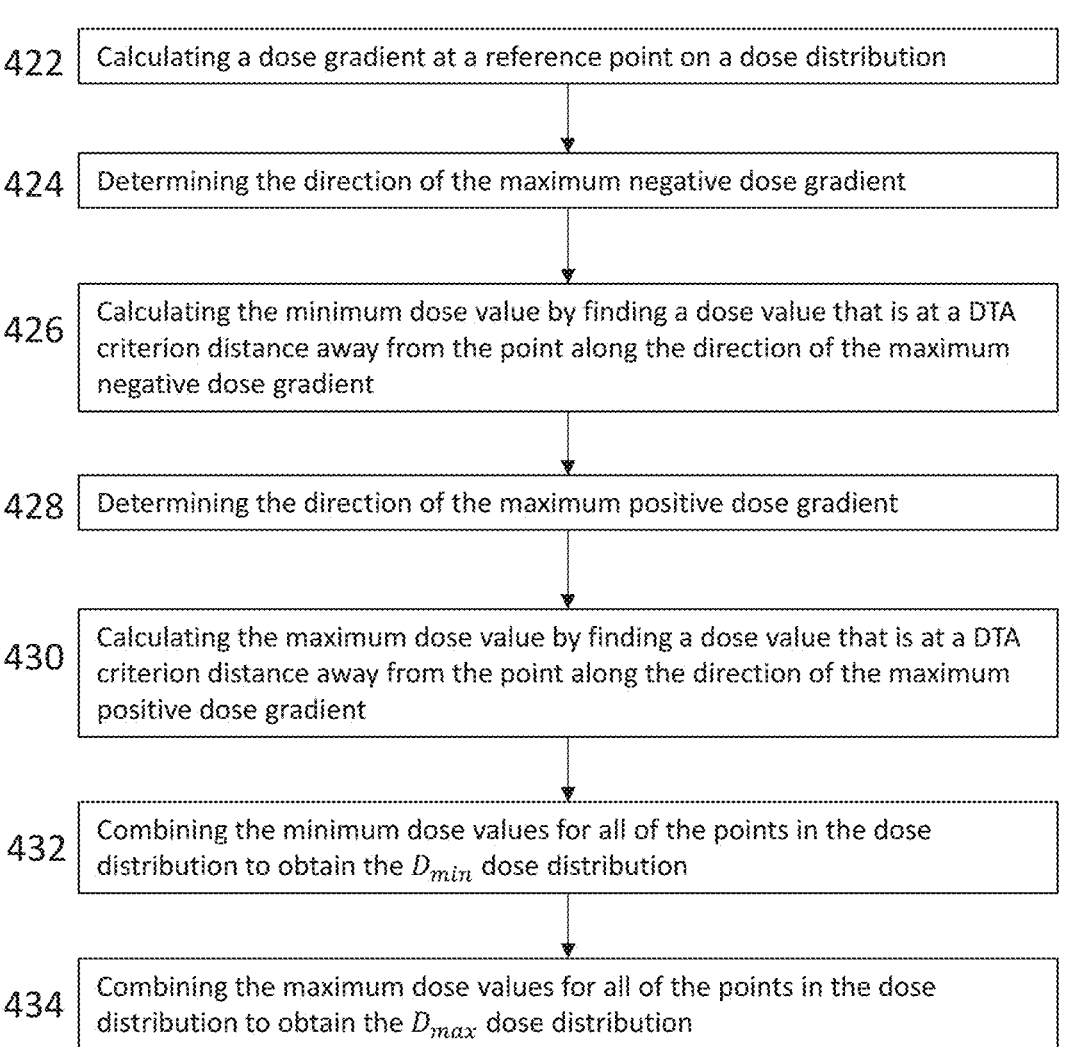
FIG. 4B depicts a flowchart representation of one variation of a method for calculating the minimum dose value at every point (in the dose distribution) to derive the $D_{min}$ dose distribution and for calculating the maximum dose value at every point (in the dose distribution) to derive the $D_{max}$ dose distribution.

One variation of a method for generating a $D_{min}$ dose distribution and $D_{max}$ dose distribution based on a planned dose distribution (for example) and gamma criteria may use a gradient descent method. The method may comprise calculating the dose gradient (e.g., slope or derivative) at a series of points in the dose distribution, calculating a minimum dose value and a maximum dose value using the calculated gradient. The minimum dose value may be calculated by "moving down" the dose gradient (e.g., along a negative slope of the gradient) to a DTA criterion distance away from the initial point. The maximum dose value may be calculated by "moving up" the dose gradient (e.g., along a positive slope of the gradient) to a DTA criterion distance away from the initial point. One example of a method for calculating the minimum dose value at every point to derive the $D_{min}$ dose distribution and for calculating the maximum dose value at every point to derive the $D_{max}$ dose distribution is depicted in the flowchart of FIG. 4B. Method (420) may be applied to each point on a planned dose distribution. Method (420) may comprise calculating (422) a dose gradient at the point (e.g., a reference point), determining (424) the direction of the maximum negative dose gradient, and calculating (426) the minimum dose value for that point by finding a dose value that is at a DTA criterion distance away from the point along the direction of the maximum negative dose gradient. Finding the minimum dose value may comprise moving a selected fractional step along the negative dose gradient to another point on the dose distribution, sampling the dose value at that point, and repeatedly moving to and sampling dose values along the negative dose gradient until reaching a point that is at a predetermined Euclidean distance away from the initial point. The fractional step may be selected to optimize stability of gradient descent while providing a computationally efficient movement to the minimum or maximum. In some variations, the fractional steps may be predetermined, while in other variations, a line-search method may be used to optimize the fractional step. In some variations, calculating (426) the minimum dose value may comprise assigning the dose value that is at a DTA criterion distance away from the point to a different reference point that corresponds to the calculated minimum dose value and the DTA distance away from the original reference point along the vector sum of the measured gradient. The use of the gradient method to follow the dose to a DTA Euclidean distance from the initial reference point may comprise assigning the minimum dose value to a reference point (e.g., a new reference point) on the dose distribution corresponding to the calculated dose and the DTA Euclidian distance (along the vector sum of the gradients) away from the initial point. Without wishing to be bound by theory, assigning the minimum dose value to a new reference point may help ensure that the calculated dose continues to meet the Gamma condition (DD=0 at DTA away from the Gamma calculation point). The predetermined distance may be the specified DTA criterion. Method (420) may comprise determining (428) the direction of the maximum positive dose gradient, and calculating (430) a maximum dose value by finding a dose value that is at a DTA criterion distance away from the point along the direction of the maximum positive dose gradient. In some variations, calculating (430) the maximum dose may comprise assigning the dose value that is at a DTA criterion distance away as the maximum dose to a reference point (e.g., a new reference point) on the dose distribution corresponding to the calculated dose and a DTA distance away from the initial point in the direction of the vector sum of the gradients. Finding the maximum dose value may comprise moving a selected fractional step (e.g., as described above) along the positive dose gradient to another point on the dose distribution, sampling the dose value at that point, and repeatedly moving to and sampling dose values along the positive dose gradient until reaching a point that is at the predetermined Euclidean distance away from the initial point (i.e., the DTA criterion distance). The calculated dose gradient at each point (402) may be a 1-D dose gradient, a 2-D dose gradient, or a 3-D dose gradient. Method (420) may then comprise combining (432) the minimum dose values for a series of the points in the dose distribution to obtain the $D_{min}$ dose distribution and combining (434) the maximum dose values for all of the points in the dose distribution to obtain the $D_{max}$ dose distribution.

Another variation of a method for generating a bDVH based on gamma criteria is depicted in the flowchart of FIG. 4C. Method (450) may comprise calculating (452), for each point/voxel in a planned dose distribution (e.g., the planned dose distribution over the entire patient volume, the planned total dose to the patient), a minimum dose value $DTA_{min}$ that will still meet the DTA criterion (e.g., standard) of the gamma criteria, calculating (454) for each point/voxel in a planned dose distribution, a maximum dose value $DTA_{max}$ that will still meet the DTA criterion of a gamma index, calculating (456) for each point/voxel in the planned dose distribution, a $DD_{min}$ value by calculating a selected percentage of the planned dose value ($d_{percent}$) and subtracting $d_{percent}$ from the planned dose value ($d_{planned}$), calculating (458) for each point/voxel in the planned dose distribution, a $DD_{max}$ value by calculating a selected percentage of the planned dose value ($d_{percent}$) and adding $d_{percent}$ to the planned dose value ($d_{planned}$). In some variations, calculating (452) the minimum dose value $DTA_{min}$ at each point/voxel may comprise finding the minimum dose value at that point/voxel that would pass with a GI of 1, and calculating (454) the maximum dose value $DTA_{max}$ at each point/voxel may comprise finding the maximum dose value at that point/voxel that would pass with a GI of 1. The selected percentage that is used to calculate the $DD_{min}$ value (456)

and the $DD_{max}$ value (458) may be the DD criterion or standard of a GI as set (i.e., determined) by a clinician.

In some variations, the $DD_{min}$ and/or $DD_{max}$ values may be absolute (i.e., fixed) percentage values of a planned dose. These absolute percentage values may be positive or negative values. For example, $DD_{min}$ may be calculated by subtracting 3% of a planned dose prescription and $DD_{max}$ may be calculated by adding 3% of the planned dose prescription for a dose criterion of 3%. In other variations, the $DD_{min}$ and/or $DD_{max}$ values may be relative percentage value, for example, the proportion of a reference dose (such as the planned dose) that is deliverable (or has been delivered).

Method (450) may comprise generating (460) a $D_{min}$ dose distribution by taking the lesser of $DTA_{min}$ and $DD_{min}$ for each point/voxel in the planned dose distribution:

$$D_{min} = \min(DTA_{min}, DD_{min})$$

Method (450) may also comprise generating (462) a $D_{max}$ dose distribution by taking the greater of $DTA_{max}$ and $DD_{max}$ for each point/voxel in the planned dose distribution $$D_{max} = \min(DTA_{max}, DD_{max})$$

After generating a minimum dose distribution ($D_{min}$) and a maximum dose distribution ($D_{max}$), method (450) may comprise generating (464) a minimum DVH by calculating a DVH of the $D_{min}$ dose distribution, generating (466) a maximum DVH by calculating a DVH of the $D_{max}$ dose distribution, and generating (468) a bDVH by setting the minimum DVH as the lower bound, the maximum DVH as the upper bound, and the DVH of the planned dose distribution as the nominal DVH.

One variation of a method for calculating $DTA_{min}$ and $DTA_{max}$ for each point in a dose distribution is depicted in the flowchart of FIG. 4D. Method (440) may comprise generating (442) a set of dose values that comprise the dose values at locations in the dose distribution that are at a DTA criterion distance away from the point, determining (444) the lowest dose value in the set, determining (446) the highest dose value in the set, and designating (448) the lowest dose value as the $DTA_{min}$ value for the point and the highest dose value as the $DTA_{max}$ value for the point.

Methods for Locating a Target Region Using Sparse Imaging Data

At the time of treatment, imaging data may be acquired, and the radiotherapy system controller may be configured to analyze the acquired imaging data to identify the location of a target region and/or determine whether it is safe to deliver radiation to the target region at the identified location. Analyzing the imaging data may comprise calculating imaging-based metric values and/or dose metric values and comparing the calculated metric values to the identification parameters of a target region's ID profile. If the calculated metric values meet the criteria of the identification parameters, the radiotherapy system may generate a notification to the operator that indicates the location of the target region and/or that it is safe to deliver radiation to the target region at the identified location. One or more of the calculated metric values may be calculated based on the imaging signal data within the contour(s) of the target region, and some methods may comprise identifying the location of the target region before calculating the metric values.

The updated location of a target region may also be used to generate a graphical representation comprising the target region contour(s) at the updated location in combination with anatomical landmarks and/or other contour(s). For example, a graphical representation or visualization may comprise a tumor contour (e.g., GTV, CTV) and a BTZ contour, optionally composited with a CT or MR anatomical image. In some variations, a graphical representation may comprise visual indicia that highlights the target region contour at the update location in a PET image. Some radiotherapy system controllers may be configured to compare the boundaries of the target region contour with boundaries of an outer contour that encapsulates the target region contour. The outer contour may be a BTZ contour and/or a safety contour. If the target region contour is too close to the boundaries of the outer contour (e.g., target region contour boundary is within a safety margin or tolerance of the outer contour boundary), the controller may generate a notification to the operator to indicate that the target region has moved toward the outer contour. In some variations, if the target region contour is outside of the outer contour boundary, the controller may generate a notification to the operator and radiation delivery may be paused. For example, if a target region drifts outside of the BTZ during a BgRT treatment session, the controller may generate an interlock to immediately cease radiation delivery until the operator has conducted an evaluation on whether it is appropriate to resume treatment.

In some variations, methods for locating a tumor (e.g., a tumor or target region within a BTZ contour) may comprise using sparse imaging data to iterate on an initial image of the target region and generate an image that represents the updated location of the target region. "Sparse" imaging data may be imaging data that is acquired over limited-time windows (e.g., less than about 10 seconds, about 1 second or less) and/or may be imaging data that results from stochastic processes (e.g., positron emissions in PET imaging, photon emissions in SPECT imaging) For example, imaging data may be "sparse" if the location of the tumor centroid cannot be determined from the imaging data. One variation of an iterative method based on Bayesian statistics may comprise an expectation-maximization method, which may iteratively shift the location of the target region in the initial image to an updated location using newly-acquired (e.g., limited-time sampled) imaging data. This method may help facilitate more frequent, and/or continuous, localization of the target region when there is sparse imaging and/or position data of the target region. While the sparse imaging data acquired over a limited-time interval may be insufficient to directly determine the centroid of a moving target region, the methods described herein utilize the sparse imaging data to iteratively update and/or refine the location of the target region from an initial image. These methods may be used to track the location of a target region during a treatment session using limited-time sampled imaging data, without calculating the location of the center of mass of the target region. Because the data acquisition window is short (e.g., a few seconds or less, about 1 second or less), the location of the target region may be determined in real-time. The expectation-maximization method described herein may be used to generate an estimated location of target region and the estimated location may be compared with the boundary of the BTZ (or any pre-defined region and/or safety margin). If the estimated target region is outside of the acceptable boundary (or estimated to be likely outside of the acceptable boundary), the controller may generate a notification to the operator to help them decide whether radiation delivery should be paused. For example, if the estimated target location drifts outside of the BTZ (and/or any portion of the target region is, or likely to be, outside of the BTZ), the controller may generate a notification to the operator. Optionally an interlock may be generated to immediately cease radiation delivery until the operator has conducted an evaluation on whether it is appropriate to resume treatment.

One variation of a method for locating a target region may comprise using an initial image of a tumor to generate an initial map of pixel tumor likelihood values. The initial map of pixel tumor likelihood values may be a probability map that indicates whether a particular image pixel belongs to the tumor or belongs to the background. In some variations, the initial map of pixel tumor likelihood values may be a map where the pixels attributed to the tumor have a value of "1" and the pixels attributed to the background (i.e., are not part of the tumor) have a value of "0". A map of pixel tumor likelihood values that has binary values may also be referred to as a map of pixel tumor probability values. In some variations, a map of pixel tumor likelihood values may have pixel values that are any value greater than or equal to zero and less than or equal to one. The initial map of pixel tumor likelihood values may then be updated and iterated upon using newly-acquired imaging data and an expectation-maximization method. During each iteration, tumor-likelihood values and background-likelihood values may be calculated for each pixel in the image and combined to update the map of pixel tumor likelihood values. When stopping criteria are reached, the location of the target region is determined based on the final map of pixel tumor likelihood values. Stopping criteria may include, for example, reaching the maximum number of iterations, and/or meeting a threshold average pixel value within the tumor contour that has been shifted according to the updated map of pixel tumor likelihood values. The initial image and/or the newly-acquired imaging data may comprise PET imaging data, CT imaging data, X-ray imaging data, SPECT imaging data, MR imaging data, etc.

FIGS. 5A and 5B depict one variation of a method (500) for locating a tumor based on an initial image and newly-acquired imaging data. Method (500) may comprise defining (502) a tumor contour and a BTZ contour on a planning image. The tumor contour and BTZ contour may be defined by a clinician and/or by a controller (e.g., treatment planning controller and/or radiotherapy system controller). For example, the controller may be configured to execute an algorithm that identifies contours of potential regions-of-interest, and a clinician may review the proposed contours and approve or modify as desired. The planning image may be a PET image, a PET/CT image, an MR image, ultrasound image, and/or any combination thereof. In some variations, the planning image may be a composite of multiple images of the same or different imaging modality. The image signal for each pixel is denoted as Act(r). In a PET image, the image signal may represent PET activity and/or activity intensity of each pixel.

Method (500) may then comprise calculating (504) the average and standard deviation ($\mu_{sig}$, $\sigma_{sig}$) of the image signal values over the pixels within the tumor contour in the planning image, calculating (506) the average and standard deviation ($\mu_{bck}$, $\sigma_{bck}$) of the image signal values over the pixels outside the tumor contour but within the BTZ contour, and generating (508) an initial map of pixel tumor probability values (CTVmask$^0$) where pixels within the tumor contour are assigned as a high tumor-probability value (e.g., 1)

and the pixels outside the tumor contour are assigned as a low tumor-probability value (e.g., 0). Steps (502-508) may be performed during treatment planning and may optionally be performed at least once during a treatment session.

During a treatment session, the location of the tumor may be updated using newly-acquired imaging data to iterate on an initial image and/or probability map. Method (500) may comprise acquiring (510) updated imaging data of the patient region that includes the tumor and calculating (512) a tumor-likelihood value $$\mathcal{L}_{sig}^{i}\ (r)$$

and background-likelihood value $$\mathcal{L}_{bck}^{i}(r)$$

for all the pixels in the acquired imaging data, where i denotes the iteration index and may start at i=1. In some variations, the updated imaging data may be PET imaging data and the tumor-likelihood value and background likelihood value for each pixel may be as calculated as follows:

$$\mathcal{L}_{sig}^{i}(r) = \left(1 + e^{-\left(\frac{Act(r) - \mu_{sig}^{i-1}}{\sigma_{sig}^{i-1}}\right)}\right)^{-1},$$

$$\mathcal{L}_{bck}^{i}(r) = \left(1 + e^{-\left(\frac{\mu_{bck}^{i-1} Act(r)}{\sigma_{bck}^{i-1}}\right)}\right)^{-1}$$

Where Act(r) is the PET activity/signal intensity for that pixel from the acquired imaging data. For the first iteration $$i = 1, \mu_{sig}^{0}, \sigma_{sig}^{0} \text{ and } \mu_{bck}^{0}, \sigma_{bck}^{0}$$

are $\mu_{sig}$, $\sigma_{sig}$ and $\mu_{bck}$, $\sigma_{bck}$, respectively, are the values that were calculated for the planning image.

Method (500) may then comprise calculating (514) a map of pixel tumor likelihood values $$CTV_{likelihood}^{i}(r)$$

using the previous map of pixel tumor probability values (CTVmask$^{i-1}$), the tumor-likelihood values, the background-likelihood values. In some variations, the map of pixel tumor likelihood values may be calculated as follows:

$$CTV_{likelihood}^{i}(r) = \frac{\mathcal{L}_{sig}^{i}(r) * CTVmask^{i-1}(r)}{\mathcal{L}_{sig}^{i}(r) * CTVmask^{i-1}(r) + \mathcal{L}_{bck}^{i}(r) * \left(1 - CTVmask^{i-1}(r)\right)}$$

For the first iteration i=1, the previous map of pixel tumor probability values CTVmask$^{0}$ is the initial map of pixel tumor probability values calculated from the planning image (e.g., generated in step (508)).

Method (500) may further comprise calculating (516) a centroid location of the map of pixel tumor likelihood values $$CTV_{likelihood}^{i}(r)$$

within the BTZ contour, and shifting (518) the tumor contour to the calculated centroid location. In some variations, the centroid location may be calculated as follows:

$$[x_c, y_c, z_c] = \frac{\sum_j CTV_{likelihood}^{i}(r_j) * [x_j, y_j, z_j]}{\sum_i CTV_{likelihood}^{i}(r_j)}$$

Method (500) may further comprise generating (520) an updated map of pixel tumor probability values CTVmask$^{i}$(r) where pixels within the shifted tumor contour are assigned as a high tumor-probability value (e.g., 1) and the pixels outside the shifted tumor contour are assigned as a low tumor-probability value (e.g., 0), calculating (522)

$$\mu_{sig}^{i}$$

over the pixels within the shifted tumor contour, and comparing (524)

$$\mu_{sig}^{i}$$

with $$\mu_{sig}^{i-1}.$$

For the first iteration $$i = 1, \mu_{sig}^{i-1}$$

is $$\mu_{sig}^{0},$$

which was calculated for the planning image. If $$\mu_{sig}^{i}$$

differs from $$\mu_{sig}^{i-1},$$

the shifted tumor contour may not reflect the actual location of the tumor and method (500) may then comprise additional iterations on the map of pixel tumor likelihood values. In this case, method (500) may comprise calculating (528)

$$\sigma^i_{sig}$$

over the pixels within the shifted tumor contour and $$\mu^i_{bck}, \sigma^i_{bck}$$

over the pixels outside the shifted tumor contour but within the BTZ contour, and iterating (i=i+1) on map of pixel tumor likelihood values $CTV_{likelihood}$. For example, method (500) may comprise iterating (530) back to step (512) and repeating steps (512-524).

However, if the comparison (524) determines that $$\mu^i_{sig}$$

approximates $$\mu^{i-1}_{sig}$$

(e.g., within a prescribed or acceptable tolerance or margin), the shifted tumor contour may reflect the actual location of the tumor and no further iterations on the map of tumor likelihood values are needed. Method (500) may then stop (526) iterating and optionally generates a graphical representation of the shifted tumor contour to the operator and output the graphical representation to a display. In some variations, the graphical representation may comprise the shifted tumor contour (i.e., at the updated tumor location) and the initial tumor contour (i.e., at the initial tumor location). For BgRT delivery, the graphical representation may optionally include the BTZ contour and the shifted tumor contour relative to the BTZ contour. In some variations, method (500) may limit the number of iterations on the map of tumor likelihood values, and once that iteration limit has been reached, method (500) stops and optionally generates a graphical representation of the shifted tumor contour to the operator and output the graphical representation to a display. For example, the number of iterations may be from about 5 iterations to about 100 iterations, e.g., about 10 iterations, about 15 iterations, about 25 iterations, about 30 iterations, about 50 iterations, about 60 iterations, about 75 iterations, etc., as may be desirable.

The updated tumor location as determined by the method (500) may optionally be used as part of positioning the patient and/or the target region(s) at the beginning of a treatment session. Identifying the updated location of the target region may facilitate the calculation of PET data metric values and/or dose metric values, including, but not limited to, SUV metric values of the target region (e.g., mean SUV, NTS, AC), PET tracer concentration, metabolic tumor volume, expected delivery fluence, expected delivery dose volume, DVHs across the expected delivery dose volume, GI values, and the like. In some variations, the dose metric values calculated based on the updated location of a target region as determined by method (500) may help an operator to determine whether the dose to be delivered (i.e., delivery dose) is within acceptable bounds and therefore, safe to deliver to the patient.

The method (500) may optionally be used during a treatment session to determine whether the location of the tumor has changed during radiation delivery, and to generate a graphical representation of any location changes. One or more steps of the method (500) (e.g., steps 512-524) may be performed by the radiotherapy system controller throughout a treatment session. This may allow the operator to track (via the graphical representation) the actual location of a target region throughout the session. For example, the location of a target region may be updated between shuttle passes, at preset intervals during radiation delivery, and/or at the operator's request (e.g., the operator may issue a command at any time during a treatment session to the radiotherapy system to update the target region location and to refresh the graphical representation of its location. During BgRT delivery to a target region, the updated location of the target region may be compared with the boundaries of the BTZ and if the contours of the target region fall outside of the BTZ boundaries, or are not located within a pre-determined (e.g., safety) margin from the BTZ boundaries, then a notification may be generated by the radiotherapy system to alert the operator. The notification may be a visual and/or audible indicator and may optionally include a graphical representation of the relative positions of the target region contour and the BTZ contour.

While the method (500) is described in the context of tracking the location of a target region, in some variations, the method (500) may be used to track the location of radiation-sensitive structures (e.g., OARs) so that the radiotherapy system can limit the radiation delivery to these OARs. In some variations, an OAR contour may be defined for an OAR that is PET-avid (e.g., bladder, kidneys, etc.). The pixel values inside the OAR contour may be determined to be a part of the OAR. The method (500) may be used to determine the location of the OAR by iteratively updating an initial of map of pixel OAR likelihood values (e.g., pixel OAR likelihood values) using newly-acquired imaging data (e.g., PET imaging data) and an expectation-maximization method. During each iteration, OAR-likelihood values and background-likelihood values may be calculated for each pixel in the PET image and combined to update the map of pixel OAR likelihood values. When stopping criteria are reached, the location of the OAR may be determined based on the final map of pixel OAR likelihood values. Using this method, the OAR contour may be rigidly shifted based on the PET imaging data. In some variations, the updated location of the OAR may be used to determine whether it has shifted beyond a predetermined, acceptable distance. If the OAR has moved beyond an acceptable margin, it may be at risk for higher-than-acceptable radiation exposure, and the radiotherapy system controller may adjust delivery parameters and/or delivery fluence in order to avoid further irradiation of the OAR. For example, some methods may comprise re-optimizing the delivery fluence with a cost function that has a stricter penalty function on the OAR before continuing with radiation delivery.

Target Localization Using a Tumor Identification Profile

While the location of a target region may be identified using an iterative method based on Bayesian statistics and an initial image (e.g., the expectation-maximum method (500) depicted in FIGS. 5A and 5B), in some variations, the location of a target region may be identified using a tumor ID profile. For example, for patients with a single target region, the location of the target region at the time of treatment may be identified with newly-acquired imaging data using either the iterative EM method or a tumor ID profile. However, for patients with multiple target regions, it may be desirable to identify the locations of the multiple target regions during radiation delivery using their respective target ID profiles. In some variations, the EM method may be used at the start of a treatment session to locate the target region, and the tumor ID profile may be used to locate the target region during the treatment session (e.g., during radiation delivery). In some variations, the EM method may be used in combination with the tumor ID profile to identify the location of a target region. For example, the tumor ID profile may comprise an identification parameter that includes an initial image of the target region and its corresponding initial map of pixel tumor likelihood values. In some variations, a method for identifying the location of a target region may comprise identifying the location of the BTZ based on the BTZ contour identification parameter of the tumor ID profile, and then using the EM method to determine the location of the target region within the BTZ contour that has been shifted to its identified location. The EM method may optionally be used to continuously update the location of one or more target regions during a treatment session. For example, the location of target regions may be updated at set time intervals or time points using their respective tumor ID profiles (e.g., between shuttle passes), while the EM method may be used to update the location of target regions whenever new imaging data is acquired. For example, during a BgRT session, PET imaging data may be continuously acquired during treatment delivery, and this continuously acquired PET imaging data may be used to continuously update the location of one or more target regions by iterating on previous images using the EM method. In some variations, the updated location of the target region may be compared with the boundaries of the BTZ and if the contours of the target region fall outside of the BTZ boundaries, or are not located within a pre-determined (e.g., safety) margin from the BTZ boundaries, then a notification may be generated by the radiotherapy system to alert the operator. The notification may be a visual and/or audible indicator and may optionally include a graphical representation of the relative positions of the target region contour and the BTZ contour.

Some variations of a method for identifying a target region using a tumor ID profile may comprise acquiring a PET image, identifying regions of the image that have PET data that satisfy a PET data criterion of a tumor ID profile, calculating, for each of the identified regions, a dose metric value based on the PET data, and selecting the region that has a dose metric value that meets the dose metric criterion of the tumor ID profile. A selected region that meets one or more of the identification parameters (e.g., criterion) of an ID profile may be identified as the target region, and its location may be used to facilitate physical and/or virtual localization. Optionally, a method may comprise generating a graphical representation of the identified target region at its location within an image (e.g., a composite PET/CT image, PET image, CT image, etc., optionally in conjunction with one or more contours of pre-defined regions such as the CTV, PTV, GTV, BTZ, etc.) and the graphical representation may be output to a display device.

One variation of a method for identifying the location of a target region is represented in FIG. 6A. Method (600) may comprise acquiring (602) PET and CT images of a patient, identifying (604) candidate regions in the PET image that meet the PET data criterion of a target region's tumor identification (ID) profile, calculating (606), for each of the identified regions, a dose metric value using the PET data in that region, and identifying (608) the location of the target region by selecting the candidate patient region that has the delivery dose metric value that meets the dose metric criterion of the target region's tumor ID profile. The identification (604) of candidate regions in the PET image may utilize a pattern search algorithm, for example, template-based matching using cross correlation, template matching using a deformable template model, feature-based template matching using deep convolutional neural networks, and/or the EM method described above. In some variations, identifying (604) candidate regions that meet PET data criterion may comprise shifting the BTZ contour and/or target region contour(s) to the candidate regions, and then calculating PET-based metric values for the shifted BTZ and/or target region contour(s). The candidate regions that meet the PET data criteria of the ID profile may be moved forward to the next step, where the dose metric values are calculated (606) and compared to the corresponding dose metric criteria of the ID profile. In some variations, calculating the dose metric values for the candidate regions may comprise generating an expected delivery dose volume using the acquired PET and CT images, and calculating one or more dose metric values based on the generated expected delivery dose volume. Alternatively, or additionally, the EM method may be used on one or more of the candidate regions to find the location of the target region, and shift the target region contour to the updated location. The one or more dose metric values may be calculated based on the shifted target region contour. The candidate region that meets the PET data criteria and the dose metric criteria of the ID profile may be identified as the location of the target region. In some variations, each candidate region may be assigned a pattern match score that indicates the degree to which the PET-based metric and dose metric values are consonant with (e.g., match) the corresponding ID profile identification criteria. In the event multiple candidate regions meet the PET data and dose metric criteria of the ID profile, the candidate region with the highest pattern match score is deemed to be the location of the target region. Optionally, method (600) may comprise generating (610) a graphical representation of the target region at the identified location. In some variations, the graphical representation may also include the contours of one or more of the CTV, GTV, PTV, and/or BTZ. Method (600) may be used to identify the locations of one target region or multiple target regions. In some variations, the identified location(s) may be used to facilitate patient and/or couch positioning at the beginning of a treatment session and/or monitor or confirm the patient's position during the delivery of radiation treatment.

Figure 6B:
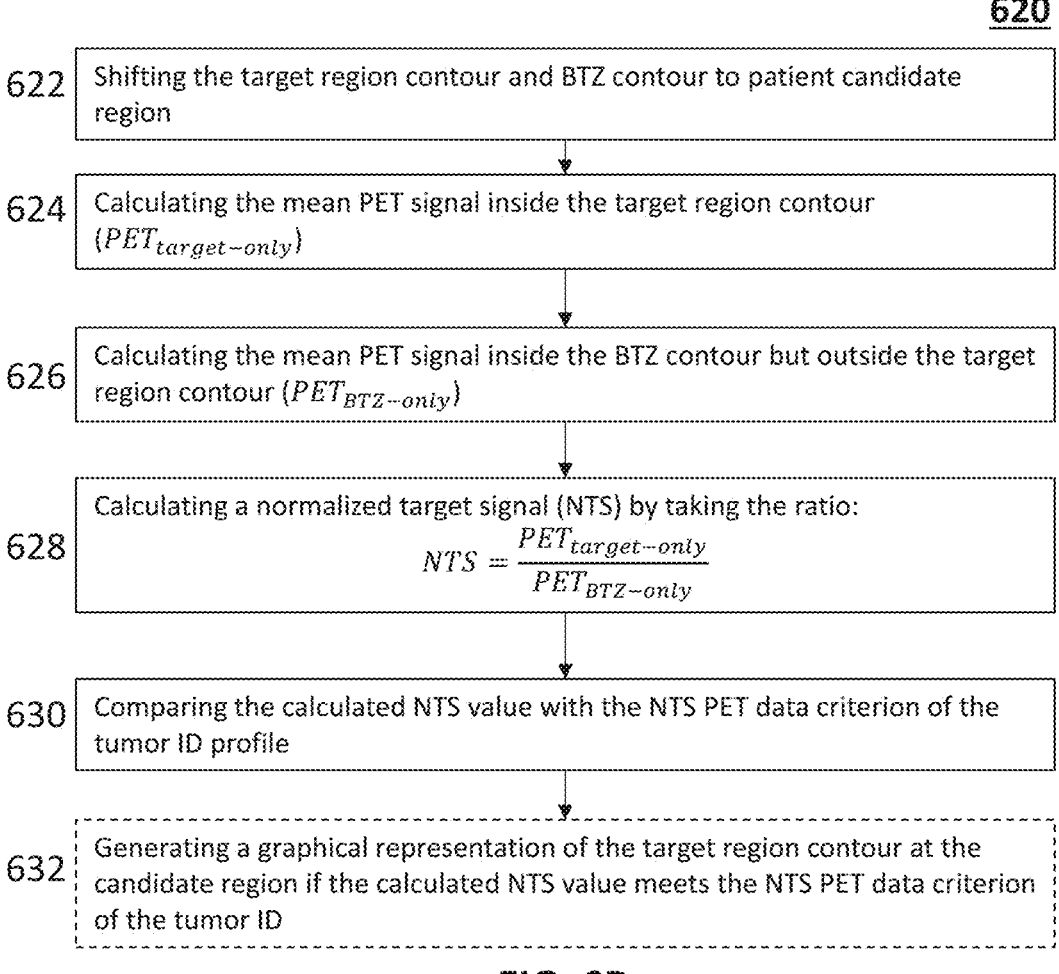
FIG. 6B depicts a flowchart representation of one variation of a method for calculating a normalized target signal (NTS) value.

In some variations, identifying (604) candidate regions in the PET image that meet the PET data criterion of a target region's tumor identification (ID) profile may comprise calculating one or more PET-based data metric values, for example, SUV metric values and/or PET tracer concentration. FIG. 6B depicts a flowchart representation of one method of calculating a NTS value, which is a PET-based data metric value. Method (620) may comprise shifting (622) the target region contour and BTZ contour to the patient candidate region, calculating (624) the mean PET signal inside the target region contour ($PET_{target-only}$) calculating (626) the mean PET signal inside the BTZ contour but outside the target region contour ($PET_{BTZ-only}$), and calculating (628) a normalized target signal (NTS) by taking the ratio:

$$NTS = \frac{PET_{target-only}}{PET_{BTZ-only}}$$

Another variation of a method for calculating a NTS value may comprise shifting the BTZ contour to the patient candidate region, calculating a peak (e.g., $99^{th}$ percentile) PET signal inside BTZ contour ($PET_{BTZ-peak}$), calculating a mean PET signal inside the BTZ contour ($PET_{BTZ-mean}$), and calculating the NTS by taking the ratio:

$$NTS = \frac{PET_{BTZ-peak}}{PET_{BTZ-mean}}$$

Alternatively, or additionally, the NTS may be calculated by determining the maximum pixel value within the BTZ ($BTZ_{max}$), calculating the mean value ($PET_{mean-50\%}$) of all pixels/voxels within the BTZ contour having a pixel value greater than 50% of $BTZ_{max}$, calculating the mean value ($PET_{mean-bkgnd}$) of the all pixels/voxels within a BTZ shell contour that encompasses the BTZ contour, and taking the ratio of the mean values:

$$NTS = \frac{PET_{mean-50\%}}{PET_{mean-bkgnd}}$$

In some variations, the NTS may be a ratio of a mean value ($PET_{mean-80\%}$) of voxels within the BTZ contour having a voxel value greater than 80% of the maximum voxel value in the BTZ contour and a mean value ($PET_{mean-bkgnd}$) of pixels/voxels within a BTZ shell contour that encompasses the BTZ contour:

$$NTS = \frac{PET_{mean-80\%}}{PET_{mean-bkgnd}}$$

In still other variations, the NTS may be calculated based on AC values of the target and the background:

$$NTS = \frac{AC}{\sigma_{Background}} = \frac{AC^{Target} - AC^{Background}}{\sigma_{Background}}$$

Where $AC^{Target}$ may be calculated as the mean-value of the voxels within the BTZ that have a value above 80% of the maximum voxel value within the BTZ (i.e., find the maximum voxel value within the BTZ, calculate the 80% value of that voxel value as the threshold, and calculate the mean of all of the voxels within the BTZ that meet or exceed the threshold), $AC^{Background}$ is the mean voxel value within the BTZ, and where $\sigma_{Background}$ may be the standard deviation of the activity concentration values in the shell around the BTZ (i.e., BTZ shell contour).

Method (620) may further comprise comparing (630) the calculated NTS value with the NTS PET data criterion of the tumor ID profile. If the calculated NTS value matches the NTS PET data criterion (e.g., within a selected margin), the candidate region may remain a candidate for further evaluation (i.e., comparison with other identification parameters of the ID profile). In some variations, the NTS PET data criterion may be 2.0 or higher (e.g., 2.0, 2.1, 2.5, 2.7, 2.9, 3.0 or more). The NTS PET data criterion may have a first value for evaluating whether a target region would be suitable for BgRT and/or treatment planning for BgRT, and may have a second value for evaluating the safety of BgRT delivery on the day of treatment. For example, the first value may be greater than the second value (e.g., the first value may be 2.7 while the second value may be 2.0). Method (620) may comprise generating (632) a graphical representation of the target region contour at the candidate region if the calculated NTS value meets the NTS PET data criterion of the tumor ID.

Alternatively, or additionally, in some variations, identifying (604) candidate regions in the PET image that meet the PET data criterion of a target region's tumor identification (ID) profile may comprise calculating a PET tracer concentration (e.g., activity concentration AC) within a candidate target region contour located within the candidate region. In some variations, the PET data criterion may comprise a PET tracer AC threshold value. In some variations, the AC threshold value may be 2.5 kBq/mL or more, e.g., 3 kBq/mL or more, 3.5 kBq/mL or more, 4 kBq/mL or more, 4.75 kBq/mL or more, 5 kBq/mL or more, etc. FIG. 6C depicts a flowchart representation of one method of calculating the PET tracer concentration within a target region contour. Method (640) may comprise shifting (642) the tumor contour to patient candidate region, combining (644) the PET signal (e.g., pixel values) inside the tumor contour to obtain a PET avidity value of the patient candidate region ($PETavidity_{target}$), converting (646) the PET avidity value ($PETavidity_{target}$) to a tracer concentration (with units of kBq/ml), and comparing (648) the tracer concentration value with the PET tracer concentration criterion of the tumor ID profile. If the calculated PET tracer concentration value matches the PET tracer concentration criterion (e.g., within a selected margin, meets or exceeds a threshold value), the candidate region may remain a candidate for further evaluation (i.e., comparison with other identification parameters of the ID profile). Method (640) may comprise generating (650) a graphical representation of the target region contour at the candidate region if the PET tracer concentration value meets the PET tracer concentration criterion of the tumor ID.

In some variations, calculating (608) a dose metric value for a candidate region and selecting (608) the candidate regions that has the delivery dose metric value that meets the dose metric criterion of the target region's tumor ID profile may comprise calculating an expected delivery dose volume D, and calculating one or more dose metric values based on the expected delivery dose volume D. For radiotherapy using BgRT, the radiation fluence to be delivered to a target region may be calculated from PET imaging data by masking the PET data with the BTZ, projecting the PET data to the firing position of the therapeutic radiation source, and convolving with shift invariant firing filters. This may be used to be predict, after a PET pre-scan at the start of a treatment session, the radiation fluence that would be emitted to the target region. The calculated radiation fluence may be combined with anatomical data (e.g., from a CT image) to predict the dose to the target region. To identify a target region, the dose metric values calculated from the PET imaging data acquired at the time of treatment may be compared with the dose-related identification parameters of the target region's tumor ID profile. In some variations, the expected delivery dose volume D may be generated using the BTZ contour and location, the shift-invariant firing filters, and the acquired PET imaging data. The BTZ contour and firing filters may be applied to the PET imaging data to calculate the expected radiation fluence. The expected delivery dose volume D may then be calculated from the expected radiation fluence using a dose calculation algorithm, such as collapsed-cone convolution superposition, a pencil beam algorithm, and/or Monte Carlo particle transport.

FIG. 6D depicts a flowchart representation of a method for identifying candidate regions in an image by calculating dose metric values and comparing them to dose metric criteria of a tumor ID profile. Method (660) may comprise shifting (662) the BTZ contour (and/or optionally, the tumor contour) to patient candidate region in the PET image, calculating (664) an expected radiation fluence by convolving treatment planning firing filters with the PET data within the shifted BTZ contour, calculating (666) the expected delivery dose volume D based on the expected radiation fluence and patient anatomical data, calculating (668) a dose metric value from the expected delivery dose volume D, and comparing (670) the calculated dose metric value with one or more dose criteria of the tumor ID profile. If the calculated dose metric value matches the one or more dose criteria (e.g., within a selected margin), the candidate region may remain a candidate for further evaluation (i.e., comparison with other identification parameters of the ID profile). Method (660) may comprise generating (672) a graphical representation of the BTZ contour at the candidate region if the calculated dose metric value meets the one or more dose criteria of the tumor ID.

In some variations, the calculated dose metric may be a DVH, which may be compared to a tumor ID profile DVH to evaluate whether the candidate region is the location of the target region. FIG. 6E depicts a flowchart representation of one variation of a method for identifying candidate regions in an image by calculating a DVH for the candidate region and comparing the DVH to a DVH criterion of a tumor ID profile. Method (680) may comprise shifting (682) the tumor contour to patient candidate region in the PET image, calculating (684) an expected radiation fluence by convolving treatment planning firing filters with the PET data within the shifted tumor contour, calculating (686) the expected delivery dose volume D based on the expected radiation fluence and patient anatomical data, generating (688) a dose volume histogram (DVH) for the tumor contour at the candidate region based on the expected delivery dose volume D, and comparing (690) the generated DVH with a bounded DVH of the tumor ID profile. If the generated DVH for the candidate region falls within the upper and lower bounds of the bDVH, the candidate region may remain a candidate for further evaluation (i.e., comparison with other identification parameters of the ID profile). In some variations, the method may comprise determining whether the generated DVH for the candidate region is within a percent tolerance of the bDVH. For example, if X % (e.g., 95%) of the points of the generated DVH is within the bounds of the bDVH, then the candidate region may remain a candidate for further evaluation. The bDVH of the ID profile may be a GI-derived bDVH, as described previously. Method (680) may comprise generating (692) a graphical representation of the target region contour at the candidate region if the generated DVH is within the bDVH of the tumor ID.

Any of the identification parameters of the tumor ID profiles (e.g., the parameters described above in FIGS. 6A-6E) may be updated based on the imaging data acquired at the beginning of a treatment session (i.e., after the locations of the target regions have been determined, but before the delivery of therapeutic radiation). In some variations, the identification parameters are defined during a treatment planning phase that may occur days or even weeks before the treatment session. A patient's physiology and/or disease state may change in the intervening period between planning and treatment. PET tracer uptake may vary as much as ±25% between the time of treatment planning and the time of treatment delivery. While many patient and/or disease characteristics may remain the same between planning and treatment, updating the criteria of the identification parameters may help account for variabilities so that the criteria are "normalized" and/or "level-set" to the actual state of the patient at the time they are treated. For example, PET image data acquired on the day of treatment may reflect the biological state and/or physiological activities of the patient and/or target region. The NTS value calculated from this image data may be used to update the NTS PET data criterion of the tumor ID profile, and/or the tracer activity concentration (AC) calculated from the image data may be used to update the tracer concentration criterion of the tumor ID profile. Updating the PET data criterion of a tumor ID profile that was defined during treatment planning may help to account for the variabilities in tracer injection and/or tracer uptake during the treatment session as compared to prior imaging and/or treatment sessions. Alternatively, or additionally, dose metric values calculated from imaging data acquired on the day of treatment may be used to update the dose metric criterion, DVHs (e.g., bDVHs) of the tumor ID profile. The updated ID parameters (i.e., criterion/criterion) of the tumor ID profile may be used during the treatment session for continued safety and/or location monitoring. In some variations, after updating the criteria of the identification parameters at the beginning of a treatments, they may not be updated again. For example, PET data metric values and/or dose metric values may be calculated from acquired imaging data (e.g., localization CT scan, PET pre-scan) and compared to the identification parameters of the ID profile as defined during treatment planning to determine the location of a target region. The calculated PET data metric values and/or dose metric values may then be used to adjust, for example, the threshold values of identification parameter criteria (e.g., "pass" values, "fail" values, "warning" values), and/or the values of the identification parameter criteria themselves (e.g., boundaries of a bDVH). These updated ID parameters (i.e., criterion/criterion) of the tumor ID profile may be used during the treatment session for continued safety and/or location monitoring. In some variations, the tumor ID profile may not be further adjusted during the treatment session.

For example, a tumor ID profile for a target region may comprise an identification parameter that includes an NTS value of 4.0 and an acceptance threshold criterion of ±10%, as defined during treatment planning using planning images. During the treatment session, PET pre-scan data may be acquired and the NTS value may be calculated (from the PET pre-scan data) to be 3.6, which passes/meets the acceptance threshold criterion (i.e., 4.0±10%), and the location of the target region is positively identified. The tumor ID profile may be updated according to the actual NTS value. In some variations, the acceptance threshold criterion may also be updated. For example, the identification parameter NTS value may be adjusted to 3.6 and acceptance threshold criterion may be adjusted to ±5%. In this example, at a later location and/or safety check (e.g., after a first shuttle pass) using the tumor ID profile, a NTS value of 3.55 would pass/meet the adjusted acceptance threshold criterion (i.e., 3.6±5%, which has a minimum passing value of 3.42), but notably, would fail the original acceptance threshold criterion (i.e., 4.0±10%, which has a minimum passing value of 3.6). In a further location and/or safety check (e.g., after a second shuttle pass) using the tumor ID profile, a calculated NTS value of 4.3 would fail the adjusted acceptance threshold criterion (i.e., 3.6±5%, which has a maximum passing value of 3.78), but notably, would pass/meet the original acceptance threshold criterion (i.e., 4.0±10%, which has a maximum passing value of 4.4). The acceptance threshold criterion may be adjusted to have a tighter tolerance during a treatment session, since the NTS value has been updated using current imaging data. In some variations, if a metric value calculated from the acquired imaging data is within a margin of error (e.g., a measurement error) of the boundaries of the ID profile thresholds or criteria, the radiotherapy system controller may generate a notification to the operator that includes the threshold value (along with any acceptable error margins and/or threshold criterion) of the identification parameter and the calculated metric value. The notification may be a graphical representation that includes the threshold value of the identification parameter, calculated metric value, and a selection graphic element. The selection graphic element may present an option to the operator to "PROCEED" to treat the patient or to "PAUSE" treatment. In cases where the metric value is outside of the acceptable margin (e.g., threshold criterion) of the metric value, the operator may still select "PROCEED" to continue treatment. By the same token, in cases where the metric value is within of the acceptable margin (e.g., threshold criterion) of the metric value, the operator may still select "PAUSE" to halt treatment. More generally, at each location and/or safety check, the operator may choose to override the recommendation of the radiotherapy system (which may be based on the tumor ID profile) whether to proceed or pause treatment to one or more target regions.

Safety Monitoring Using a Tumor Identification Profile

The methods described herein may be used to identify the updated location of one or more target regions to facilitate patient setup (e.g., positioning the patient on the couch and/or adjusting the position of the couch) to localize the one or more target regions at the start of a treatment session, but these methods may also be used to evaluate the safety of continued radiation delivery. The location of the one or more target regions may change during a treatment session and in some circumstances, a target region may be at a location that is unsafe for radiation delivery. For example, the initial location of a target region at the start of a treatment session may be a safe distance away from an OAR, but during treatment delivery, the target region may move to a location that is too close to the OAR. In BgRT, where LTS imaging data are continuously collected during radiation delivery, the emitted fluence and/or dose delivered to the patient may be calculated and compared to the planned fluence and/or dose to confirm that the radiation delivery is proceeding as intended. The acquired LTS imaging in one shuttle pass may also be used to evaluate whether it is safe to continue with treatment. For example, LTS PET imaging data acquired during a first shuttle pass of a target region may be used to calculate PET-based metrics (such as SUV, PET tracer concentration, etc.), and compared to the PET data criteria of the tumor ID profile to determine whether BgRT delivery to that target region in a second shuttle pass would be safe. Alternatively, or additionally, the LTS imaging data may be convolved with the planned firing filters to obtain a radiation fluence, and a dose distribution (e.g., expected delivery dose volume) may be generated from the radiation fluence. Various dose metric values (e.g., DVH, GI, etc.) may be calculated from the generated dose distribution to evaluate whether that dose distribution is safe to deliver in a successive pass. LTS imaging data may also be used to estimate or identify the location of the target region relative to the BTZ to verify whether the target region is within the boundary of the BTZ. If any portion of the target region is outside the BTZ, a notification may be generated for the operator to evaluate the safety of continued treatment. This safety evaluation may be conducted at regular intervals during a treatment session, between shuttle passes, and/or as desired by the operator.

FIG. 7A depicts a flowchart representation of one variation of a method for evaluating the safety of continued radiation delivery to a target region using its tumor ID profile. This example is provided in the context of BgRT using PET imaging data, but it should be understood that this method may be used with any external beam radiation delivery method that continuously acquires imaging data of any modality to guide the emission of radiation, including but not limited to MR imaging data, CT imaging data, X-ray imaging data, ultrasound imaging data, etc. The method may also be used for evaluating the safety of continued radiation delivery to a plurality of target regions (e.g., in the context of irradiating multiple tumors for the treatment of metastatic cancer). Method (700) may comprise calculating (702) a PET data metric value for a target region using the PET data (e.g., LTS PET imaging data) within the BTZ contour, calculating (704) a dose metric value for the target region by calculating the dose delivered to the region within the BTZ contour using the PET data within the BTZ contour and patient anatomical data, comparing (706) the calculated PET data metric value with the PET data criterion of the tumor ID profile, comparing (708) the calculated dose metric value with the dose metric criterion of the tumor ID profile, and generating (710) a notification that indicates whether the calculated PET data metric values and/or the dose metric values meet the corresponding criteria of the tumor ID profile. As described above, the criteria of the tumor ID profile may be updated at the beginning of the treatment session, and the comparisons (706, 708) of calculated metric values may be to the original, planned identification parameter criteria, or to the updated identification parameter criteria. While the method (700) evaluates safety based on a PET data metric value and a dose metric value, in some variations, the safety of continued treatment may be based solely on whether the PET data metric value satisfies the PET data criterion of the ID profile. Alternatively, or additionally, in other variations, the safety of continued treatment may be based solely on whether the dose metric value satisfies the dose metric criterion of the ID profile. Method (700) may optionally comprise generating (712) a graphical representation that indicates (e.g., recommends) whether radiation treatment can proceed. For example, the graphical representation may comprise a visual indicator that lists the various tumor ID profile identification parameters (e.g., PET data, dose metric, and/or contour criteria) and whether the imaging data from the target region meets those identification parameters. In some variations, the graphical representation may comprise a graphical indicator (e.g., a plot, chart, diagram) that represents the difference between the calculated metric value(s) and the corresponding criteria/criterion of the tumor ID profile.

If it is determined that the calculated PET data metric values and/or the dose metric values do not meet the corresponding criteria of the tumor ID profile, method (700) may optionally comprise identifying an alternate location of the target region. Identifying an alternate location of the target region may comprise using any of the methods described herein, for example, the EM method (500) of FIGS. 5A and 5B, method (600) of FIG. 6A, and/or method (660) of FIG. 6D. For example, method (700) may comprise identifying one or more candidate locations for an updated location of the BTZ, generating a graphical representation of the BTZ contour at each of the candidate locations (optionally, relative to the previous BTZ contour), and transmitting the graphical representation to a display device. Optionally, the graphical representation may include a selector graphic that allows the user to select one of the candidate BTZ locations for continued treatment. The alternate BTZ location may reflect changes in the patient's position and/or target region and updating the BTZ contour in turn updates the delivery fluence, so that the delivered dose tracks the actual location of the target region.

Some variations may comprise evaluating a PET signal for BgRT delivery, where the evaluation may provide an indication of the safety of proceeding with BgRT delivery. Methods of evaluating a PET signal may comprise locating the target region contour using the EM method described above. For example, a method may comprise acquiring PET imaging data of a patient region that includes a BTZ region and a target region within the BTZ region, determining a location of the target region within the BTZ region based on the PET imaging data (e.g., using an EM method), calculating a target region standard uptake value (SUV) (optionally, an average target region SUV) for pixels of the PET imaging data within the target region, calculating a BTZ region SUV for pixels of the PET imaging data outside the target region and within the BTZ region (optionally, an average BTZ SUV), calculating a normalized PET signal metric value of the target region using the target region SUV and the BTZ region SUV, and evaluating the PET imaging data by comparing the normalized PET signal metric value with a planning PET signal metric value. Comparing the normalized PET signal metric value with a planning PET signal metric value may comprise calculating a predicted radiation dose for the target region based on the net PET signal metric value and comparing the predicted radiation dose with a prescribed radiation dose. In some variations, determining the location of the target region may comprise generating a map of pixel tumor likelihood values by calculating a tumor-likelihood value and background-likelihood value for each pixel of the PET imaging data, shifting a contour of the target region to a centroid location of the map of pixel tumor likelihood values, iteratively updating the map of pixel tumor likelihood values to generate a final map of pixel tumor likelihood values such that an average pixel value within the shifted target region contour is within a previously-defined threshold of an average pixel value within a pre-shifted tumor contour, calculating a centroid location of the final map of pixel tumor likelihood values, and determining the target region location by shifting the target region contour to the calculated centroid location. In some variations, a method may comprise acquiring PET imaging data of a patient region that includes a BTZ region and a target region within the BTZ region, determining a location of the target region within the BTZ region based on the PET imaging data (e.g., using an EM method), evaluating whether the target region is within the BTZ region, and generating a notification if any portion of the target region is outside the BTZ region.

In some variations, the calculated dose metric value for a target region may be a DVH, and the DVH may be compared to a bounded DVH to determine whether it is safe to continue radiation delivery. In some variations, the bDVH may be an identification parameter (e.g., dose metric criterion) of the target region's tumor ID profile. For example, the bDVH may be a gamma-derived bDVH generated using the methods described above. The DVH calculated during a treatment session may be compared to a gamma-derived bDVH to determine whether the delivered dose and/or the calculated delivery dose (i.e., dose to-be-delivered in the future) would meet the gamma criteria. The comparison may also indicate the proportion (e.g., percentage) of points in the delivered dose and/or calculated delivery dose that meet the passing standard GI value.

Figure 7B:
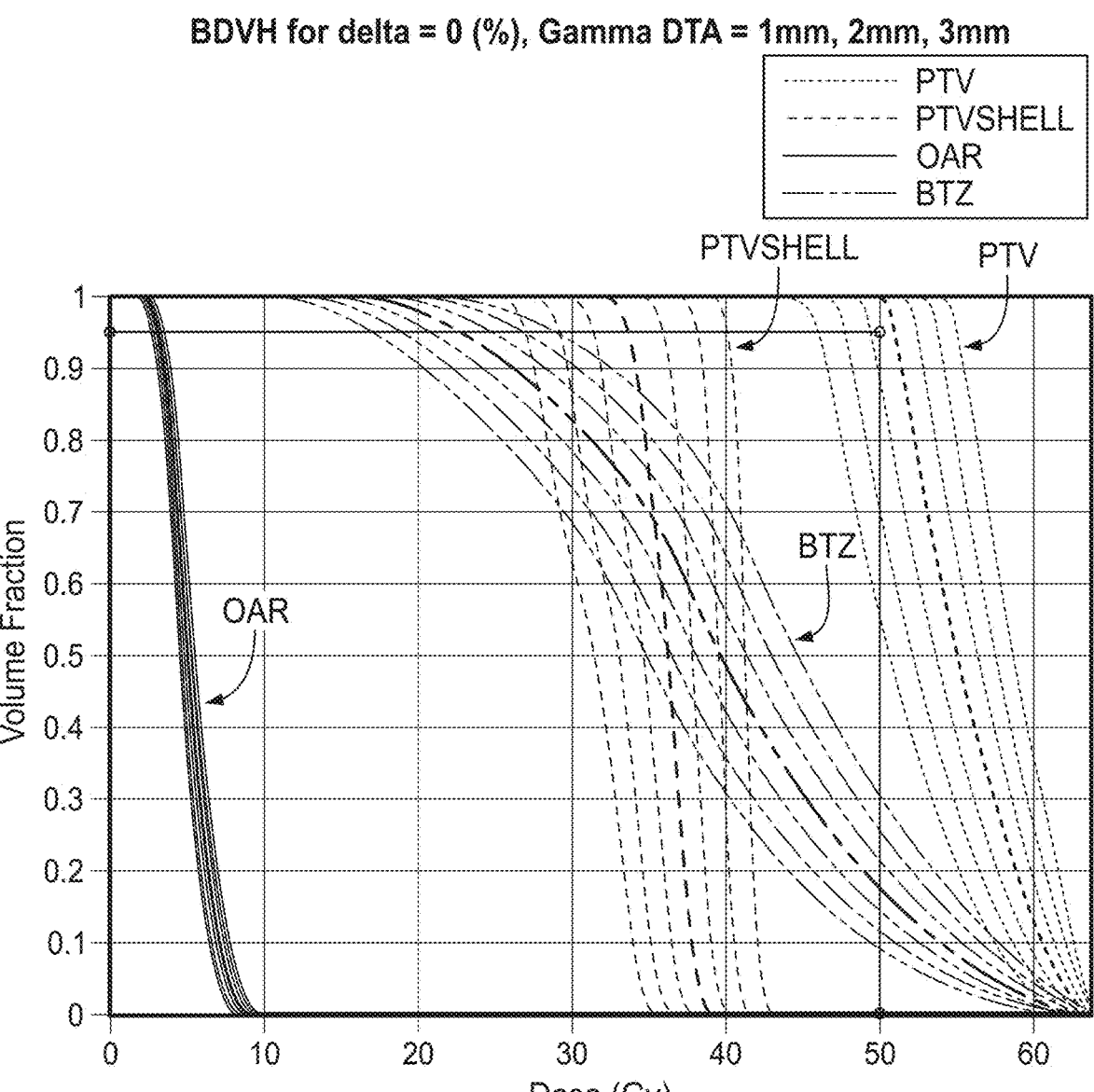
FIGS. 7B-7D depict examples of gamma-derived bDVH plots for different selected gamma criteria.
Figure 7C:
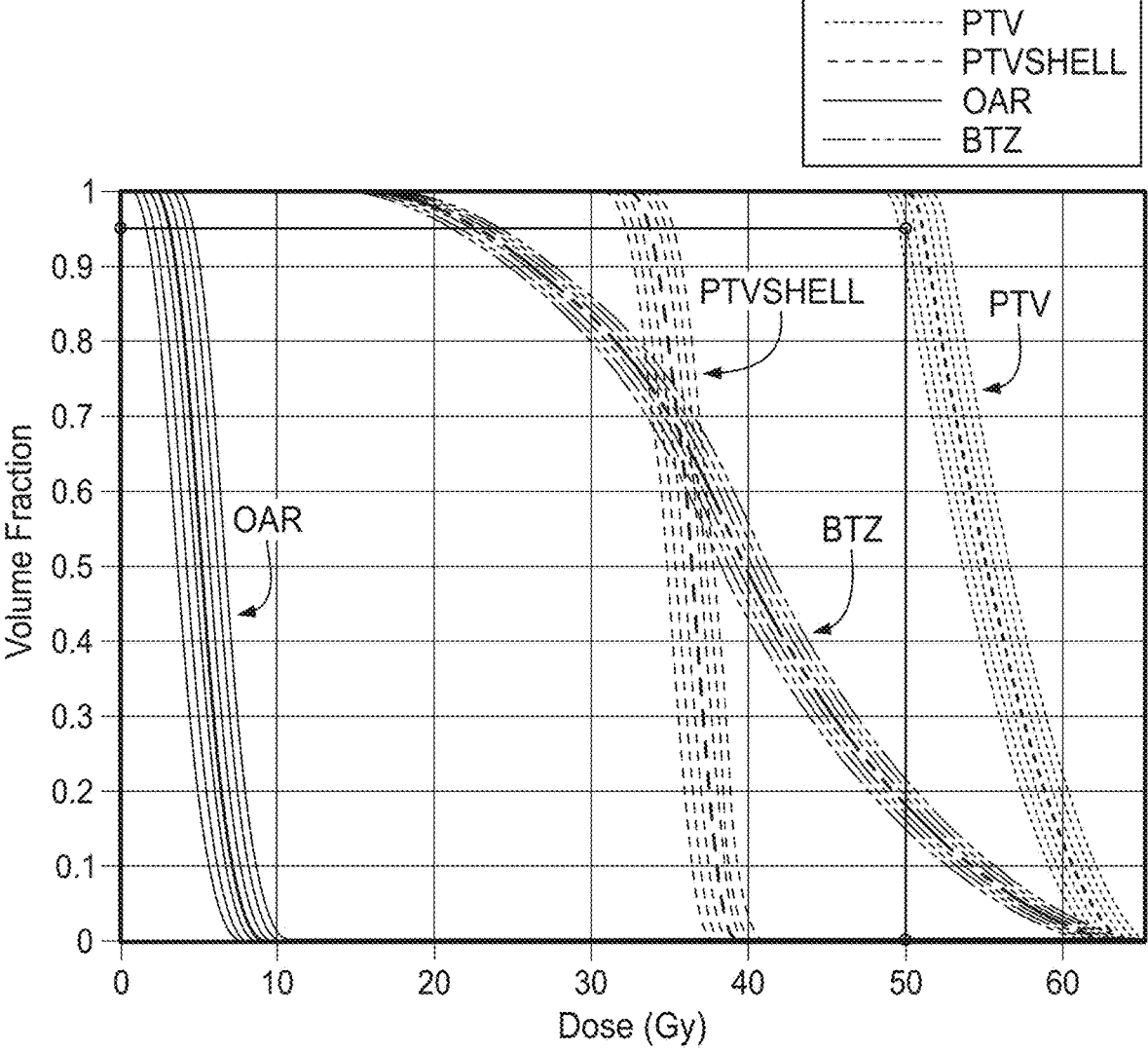
Figure 7D:
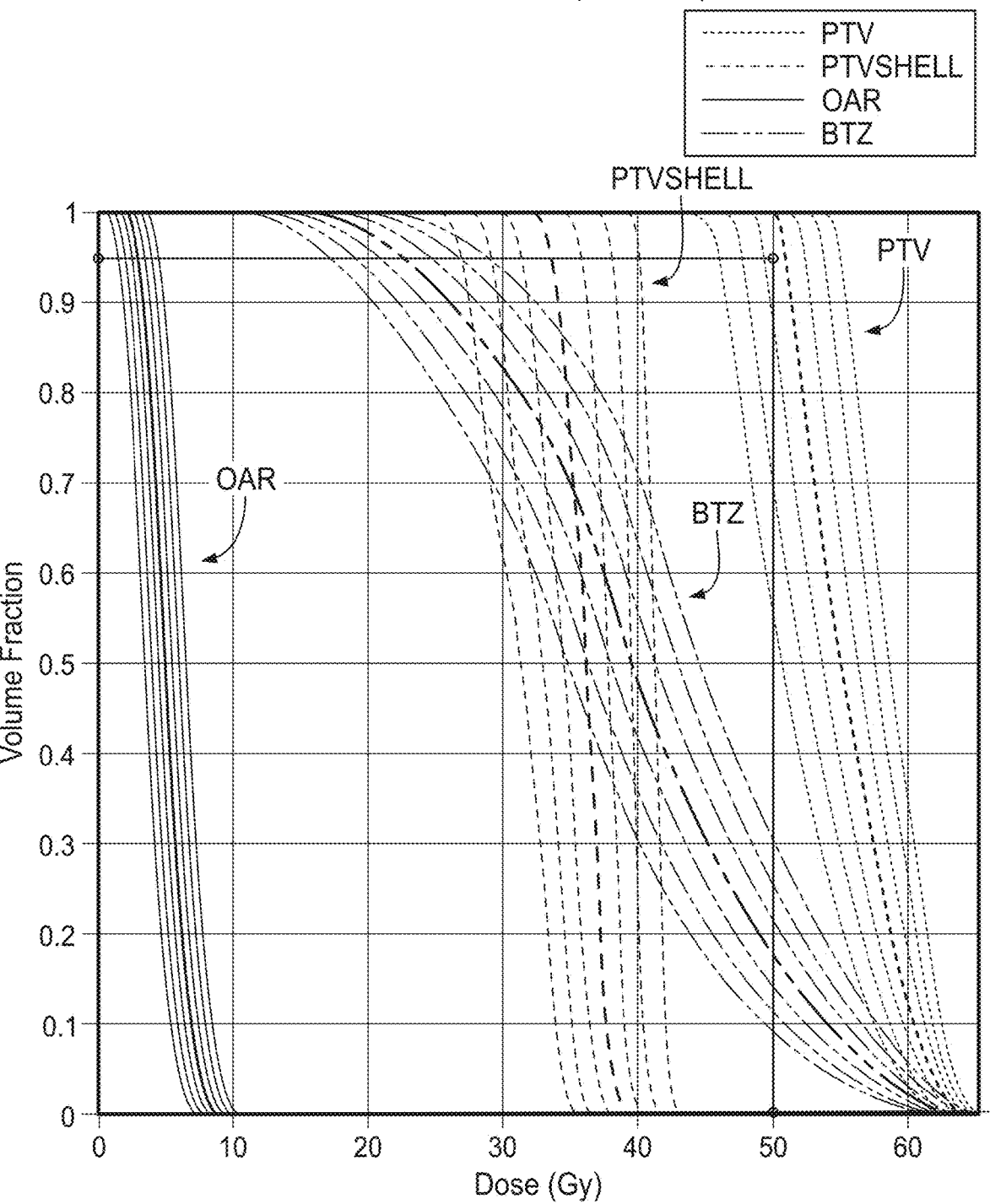

FIGS. 7B-7D depict examples of gamma-derived bDVH plots for different selected gamma criteria. The delivered dose and/or delivery dose may be compared to these bDVHs to evaluate the progress of treatment and confirm that the delivery is conforming/converging to the planned dose distribution. In some variations, these gamma-derived bDVH curves may be used to evaluate whether the dose to-be-delivered in the next shuttle pass conforms to the planned dose distribution and is thus safe to deliver.

FIG. 7B depicts bDVH curves for different volumes of interest (PTV, OAR, BTZ) for gamma criteria where $C_{DD}$=0% and $C_{DTA}$=1 mm, 2 mm, and 3 mm Notably, the greatest difference between an upper bound ($DVH_{max}$, the rightmost curve) and a lower bound ($DVH_{min}$, the leftmost curve) are in the regions with a high dose gradient (e.g., PTV, BTZ). The upper and lower bounds do not differ as much in regions with a low dose gradient (e.g., OAR). FIG. 7C depicts bDVH curves for different volumes of interest (PTV, OAR, BTZ) for gamma criteria where $C_{DD}$=1%, 2%, 3% and $C_{DTA}$=0 mm. The greatest difference between the upper bound $DVH_{max}$ and the lower bound $DVH_{min}$ are in the regions with a low dose (e.g., OAR). The upper and lower bounds do not differ as much in regions with a high dose (e.g., BTZ). FIG. 7D depicts bDVH curves for different volumes of interest (PTV, OAR, BTZ) for gamma criteria where $C_{DD}$=1% and $C_{DTA}$=1 mm, $C_{DD}$=2% and $C_{DTA}$=2 mm, and $C_{DD}$=3% and $C_{DTA}$=3 mm. In some variations, comparing a calculated DVH to any of these gamma-derived bDVH curves may facilitate the evaluation whether continued radiation delivery is safe. For example, in cases where the calculated DVH for a target region falls outside of the boundary of a bDVH, the clinician may determine and evaluate the effect of the "failed" dose on various volumes of interest. If those effects are acceptable, the clinician may instruct the radiotherapy system to continue treatment. Alternatively, or additionally, comparing a calculated DVH of a dose delivered during a treatment plan QA session may help determine whether the treatment plan needs to be modified to attain a desired dose distribution.

Methods of Using Gamma-Derived bDVHs for Treatment Plan Evaluation and Dose Delivery QA Alternatively, or additionally, the gamma-derived bDVH curves depicted in FIGS. 7B-7D may be used before a treatment session to select gamma criteria values that may be used in a treatment plan QA session so that a clinician may characterize how well a treatment plan delivers a desired dose and/or meets clinical goals. For example, the gamma-derived bDVH curves depicted in FIGS. 7B-7D may facilitate the selection of gamma criteria for evaluating the treatment plan by showing a clinician how certain gamma criteria values (i.e., values of DD, DTA) affect the dose distribution to target regions and/or OARs. A clinician may then select gamma criteria values that correspond to the bDVHs that meet clinical goals. For example, if a clinician wishes to ensure that the dose delivered to an OAR is tightly constrained, they may select the gamma-derived bDVH that has the tightest difference between the lower and upper bounds, and then use the gamma criteria associated with the selected bDVH to evaluate the treatment plan in a QA session before a treatment session. The radiation emitted during a QA session may be evaluated using the gamma criteria values associated with the selected gamma-derived bDVH. Optionally, the gamma criteria values for the selected bDVH may be used to evaluate the dose delivered to a patient after a treatment session. Any of the methods described herein may be used to select gamma criteria values that may be used in a QA session after a treatment session to evaluate how well the delivered dose approximates the planned dose.

One variation of a method of using gamma-derived bDVHs for selecting gamma criteria for treatment plan evaluation and/or quality assurance (QA) is depicted in the flowchart of FIG. 10A. Method (1000) may comprise generating (1002) a treatment plan bounded DVH (bDVH) based on a treatment plan fluence map and clinically acceptable dose variability, generating (1004) a 3-D dose distribution based on the treatment plan fluence map, generating (1006) a plurality of bDVHs, each derived from different gamma criteria values for the 3-D dose distribution, identifying (1008) a bDVH from the plurality of gamma-derived bDVHs that fits within the boundaries of the treatment plan bDVH, and selecting (1010) the gamma criteria values associated with the identified bDVH for evaluating the treatment plan. The treatment plan bDVH may comprise an upper bound DVH that represents the maximum dose that is clinically acceptable, a lower bound DVH that represents the minimum dose that is clinically acceptable, and optionally, a nominal DVH that represents the planned dose. Generating a treatment plan bDVH may comprise calculating a lower bound curve (i.e., a lower bound DVH) based on the lowest acceptable dose for a region of interest and calculating an upper bound curve (i.e., an upper bound DVH) based on the highest acceptable dose for the region of interest, as described above. Additional methods of generating bDVHs are further described in U.S. patent application Ser. No. 16/016,272 filed Jun. 22, 2018, which is hereby incorporated by reference in its entirety. The lowest acceptable dose and the highest acceptable dose may be calculated from the selected dose variability. Generating (1006) one or more bDVHs derived from different gamma criteria values may be performed using any of the methods described above with respect to FIGS. 4A-4D. Generating a 3-D dose distribution may comprise calculating a dose value for each voxel in a region of interest (e.g., target region, entire patient body, etc.) using the treatment plan fluence map and an image of the region of interest. Generating a bDVH derived from gamma criteria values may comprise calculating a lower bound curve based on a $D_{min}$ dose distribution and an upper bound curve based on a $D_{max}$ dose distribution, where $D_{min}$ and $D_{max}$ are calculated based on the DTA criterion and DD criterion of a gamma criteria. The different gamma criteria values may be a pre-defined set of criteria values (e.g., a pre-defined set of values of DD and a pre-defined set of values for DTA). Gamma-derived bDVHs may be calculated for various combinations of DTA and DD criteria values, for example, (DTA/DD) where DTA=1 mm, 2 mm, 3 mm and DD=0%, DTA=0 mm and DD=1%, 2%, 3%, (1 mm/1%), (2 mm/2%), (3 mm/3%), etc. As described above, each of the gamma-derived bDVHs comprises a lower bound DVH that is generated from a $D_{min}$ minimum dose distribution and an upper bound DVH that is generated from a $D_{max}$ maximum dose distribution. If none of the gamma-derived bDVHs are within the bounds of the treatment plan bDVH, then a notification may be generated by the treatment planning system controller to consider modifying the treatment plan.

In some variations, a method may comprise generating a family of gamma-derived bDVHs, for example, such as those depicted in FIGS. 7B-7D. A family of gamma-derived bDVHs may comprise the bDVHs where one gamma criterion value is the same (e.g., DD=0) while the other gamma criterion value varies (e.g., DTA=1 mm, 2 mm, 3 mm, etc.). From one or more families of gamma-derived bDVHs, the method may comprise identifying the bDVH(s) that best conforms with the treatment plan bDVH (e.g., falls within TP bDVH bounds), and selecting the gamma criteria values associated with the identified bDVH for evaluation and/or QA of the treatment plan. In some variations, the one or more families of gamma-derived bDVHs may be included in a graphical representation that is output to a display device. A clinician may view the different gamma-derived bDVHs and identify the bDVH(s) that are consonant with clinical goals, which may help facilitate the selection of gamma criteria. For example, a clinician may consider it a priority to limit radiation delivery to an OAR, so they may wish to select the gamma-derived bDVH that has the tightest or smallest dose spread, and use the gamma criteria values associated with that bDVH for treatment plan QA. Alternatively, or additionally, a treatment planning controller may compare the generated gamma-derived bDVHs with the treatment plan bDVH, with little or no clinician input, to identify the gamma criteria values for treatment plan evaluation and/or QA.

Figure 10B:
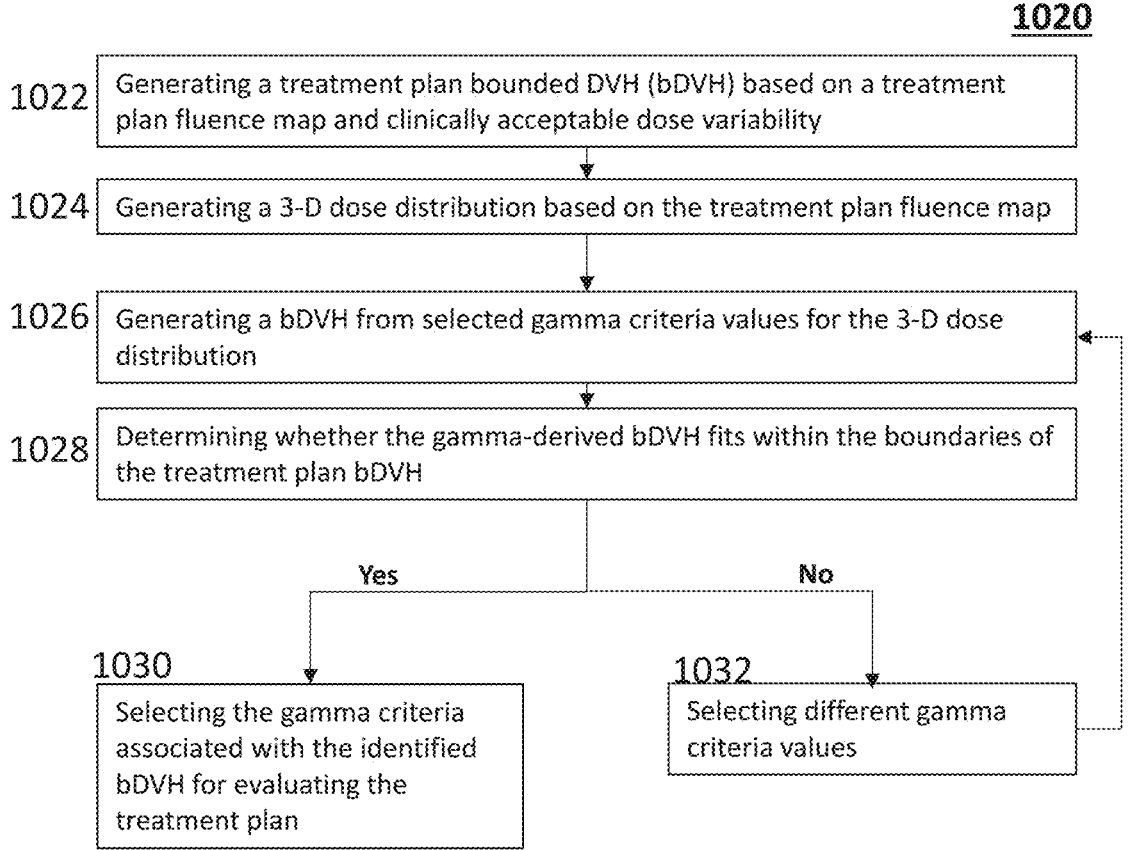
FIG. 10B depicts a flowchart representation of one variation of a method of using gamma-derived bDVHs for selecting gamma criteria values for treatment plan quality assurance (QA).

FIG. 10B depicts a variation of a method of using gamma-derived bDVHs for selecting gamma criteria values for treatment plan evaluation and/or QA. Method (1020) may comprise generating (1022) a treatment plan bDVH based on a treatment plan fluence map and clinically acceptable dose variability, generating (1024) a 3-D dose distribution based on the treatment plan fluence map, generating (1026) a bDVH from selected gamma criteria values for the 3-D dose distribution, and determining (1028) whether the gamma-derived bDVH fits within the boundaries of the treatment plan bDVH. Generating a treatment plan bDVH may comprise calculating a lower bound curve based on the lowest acceptable dose for a region of interest and calculating an upper bound curve based on the highest acceptable dose for the region of interest. The lowest acceptable dose and the highest acceptable dose may be calculated from the clinically acceptable dose variability. Generating a 3-D dose distribution may comprise calculating a dose value for each voxel in a region of interest (e.g., target region, entire patient body, etc.) using the treatment plan fluence map and an image of the region of interest. Generating a bDVH derived from gamma criteria values may comprise calculating a lower bound curve based on a $D_{min}$ dose distribution and an upper bound curve based on a $D_{max}$ dose distribution, where $D_{min}$ and $D_{max}$ are calculated based on the DTA criterion and DD criterion of a gamma criteria. This may be repeated to generate a plurality of bDVHs for a plurality of different gamma criteria values. If the gamma-derived bDVH fits within the boundaries of the treatment plan bDVH, the method (1020) may comprise selecting (1030) the gamma criteria values associated with the identified bDVH for evaluating the treatment plan. If the gamma-derived bDVH does not fit within the boundaries of the treatment plan bDVH, the method (1020) may comprise iterating on different gamma criteria values by selecting (1032) different gamma criteria values, and repeating steps (1026) and (1028). Method (1020) may comprise iterating on gamma criteria values until a gamma-derived bDVH fits within the boundaries of the treatment plan bDVH. If no gamma-derived bDVHs are found to fit within the boundaries of the treatment plan bDVH (e.g., after a maximum number of iterations), then a notification may be generated by the treatment planning system controller to consider modifying the treatment plan. Generating (1026) a bDVH derived from selected gamma criteria values may be performed using any of the methods described above, for example, as described and/or depicted in FIGS. 4A-4D. The different gamma criteria values for the iteration(s) in method (1020) may be a pre-defined set of criteria values (e.g., a pre-defined set of values of DD and a pre-defined set of values for DTA). Gamma-derived bDVHs may be calculated for various combinations of DTA *and* DD values, for example, (DTA/DD) where DD=1 mm, 2 mm, 3 mm and DD=0%, DTA=0 mm and DD=1%, 2%, 3%, (1 mm/1%), (2 mm/2%), (3 mm/3%), etc.

Example Workflow for Treating Multiple Target Regions

Figure 8A:
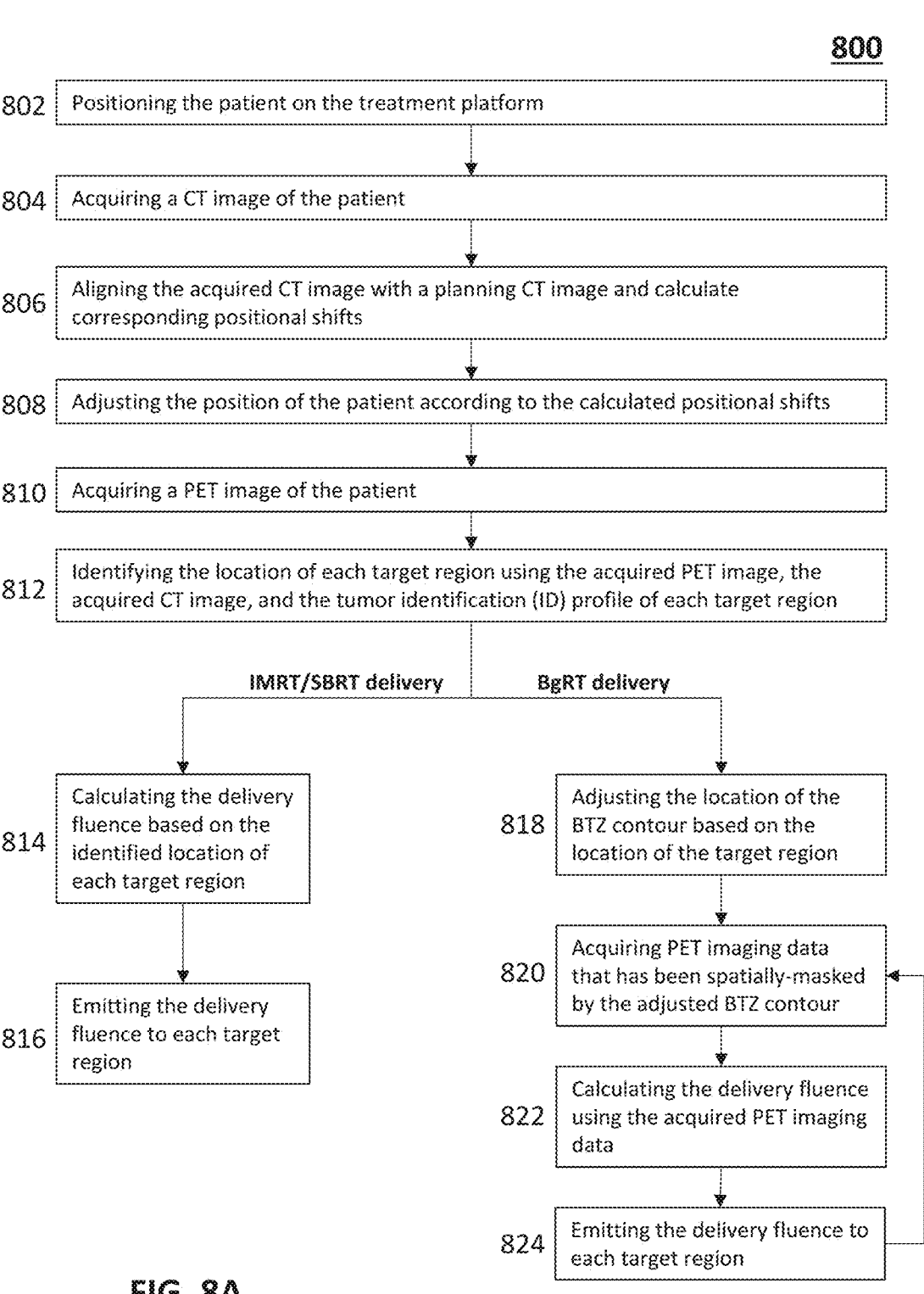
FIG. 8A depicts a flowchart representation of one variation of a method for treating one or more target regions.

Identifying the location of one or more target regions using their respective tumor ID profiles may help to streamline the workflow for radiation delivery. These methods may help reduce the number of times an operator would need to enter the radiation bunker to position (or re-position) the patient and may also help reduce the complexity of tracking the location of multiple target regions. One variation of a method for treating one or more target regions (e.g., a first target region and a second target region) is represented in the flowchart depicted in FIG. 8A. Method (800) may comprise positioning (802) the patient on the treatment platform, acquiring (804) a CT image of the patient, aligning (806) the acquired CT image with a planning CT image and calculate corresponding positional shifts, adjusting (808) the position of the patient according to the calculated positional shifts, acquiring (810) a PET image of the patient, and identifying (812) the location of each target region using the acquired PET image, the acquired CT image, and the tumor identification (ID) profile of each target region. Positioning (802) the patient may comprise positioning the patient on the couch so that they are in the same location and orientation they were in when the planning images were acquired. In some variations, this may comprise aligning patient positioning tattoos with positioning laser lights in the treatment room. For example, at the time the planning image was acquired, markers or tattoos may be placed on the patient's skin in alignment with a laser light grid, which may then be used during a treatment session to align the patient with the same laser light grid. Aligning (806) the acquired CT image with the planning CT image may comprise aligning anatomical landmarks, such as bony structures, and/or aligning OARs. Acquiring (810) the PET image may comprise acquiring PET imaging data for all of the patient's target regions. Adjusting (808) the position of the patient may be considered a physical localization for one target region. The other target regions may be virtually localized, as described above.

In some variations, one or more target regions may be irradiated according to an IMRT/SBRT plan; that is, radiation is emitted to the target region without the guidance of additionally acquired imaging data. For IMRT/SBRT delivery, method (800) may comprise calculating (814) the delivery fluence based on the identified location of each target region and emitting (816) the delivery fluence to each target region. In some variations, for IMRT/SBRT delivery, PET imaging data acquisition is omitted (i.e., steps 810 and 812 are skipped). Calculating the delivery fluence may comprise shifting the planned fluence according to any shifts calculated from the acquired CT image. Alternatively, or additionally, calculating the delivery fluence may use a virtual localization method. A virtual localization method may comprise calculating a localization function based on the identified location of a target region, and applying the localization function to a shift-invariant firing filter to calculate the delivery fluence. The identified location may correspond with a planned localization reference point for the target region, and the shift-invariant firing filter may be derived from the planned localization reference point. Virtual localization methods are further described in PCT application number PCT/US2020/40774, filed on Jul. 2, 2020, which is hereby incorporated by reference in its entirety. Since the locations of the multiple target regions are identified, they each may be virtually localized and their delivery fluence calculated accordingly. This may reduce or eliminate the need for the operator to enter the bunker to position the patient and/or couch for each target region, which may help reduce the overall treatment time. The delivery fluence to each target region may be emitted serially and/or concurrently.

Alternatively, or additionally, one or more target regions may be irradiated according to a BgRT plan; that is, radiation is emitted to the target region with the guidance of additionally acquired imaging data, such as PET imaging data. For BgRT delivery, method (800) may comprise adjusting (818) the location of the BTZ contour based on the location of the target region, acquiring (820) PET imaging data that has been spatially-masked by the adjusted BTZ contour, calculating (822) the delivery fluence using the acquired PET imaging data, and emitting (824) the delivery fluence to each target region. As described previously, calculating the delivery fluence may comprise masking the PET imaging data with the adjusted BTZ, projecting the PET imaging data to the firing position of the therapeutic radiation source, and convolving with shift invariant firing filters calculated during treatment planning Acquiring (820) PET imaging data, calculating (822) the delivery fluence, and emitting (824) the delivery fluence may be repeated throughout the treatment session. In some variations, PET imaging data may be acquired continuously and accordingly, the fluence may be calculated and delivered continuously. For example, PET imaging data may be acquired continuously (e.g., updated) in 500 ms bins, and the imaging data in the 500 ms bins may be used to continuously calculate the delivery fluence every 500 ms. In some variations, one or more of the steps in method (800) may be performed concurrently. Since the locations of the multiple target regions are identified, the BTZ contour for each target region may be adjusted accordingly, and the calculated delivery fluence may be updated to reflect the actual location of each target region. This may reduce or eliminate the need for the operator to enter the bunker to position the patient and/or couch for each target region, which may help reduce the overall treatment time. Optionally, method (800) may comprise generating a graphical representation that depicts the predicted delivery dose, a planned delivery dose for the target region(s), and outputting the graphical representation on a display device.

Example Workflow for BgRT Delivery with In-Session Safety Checks

Figure 8B:
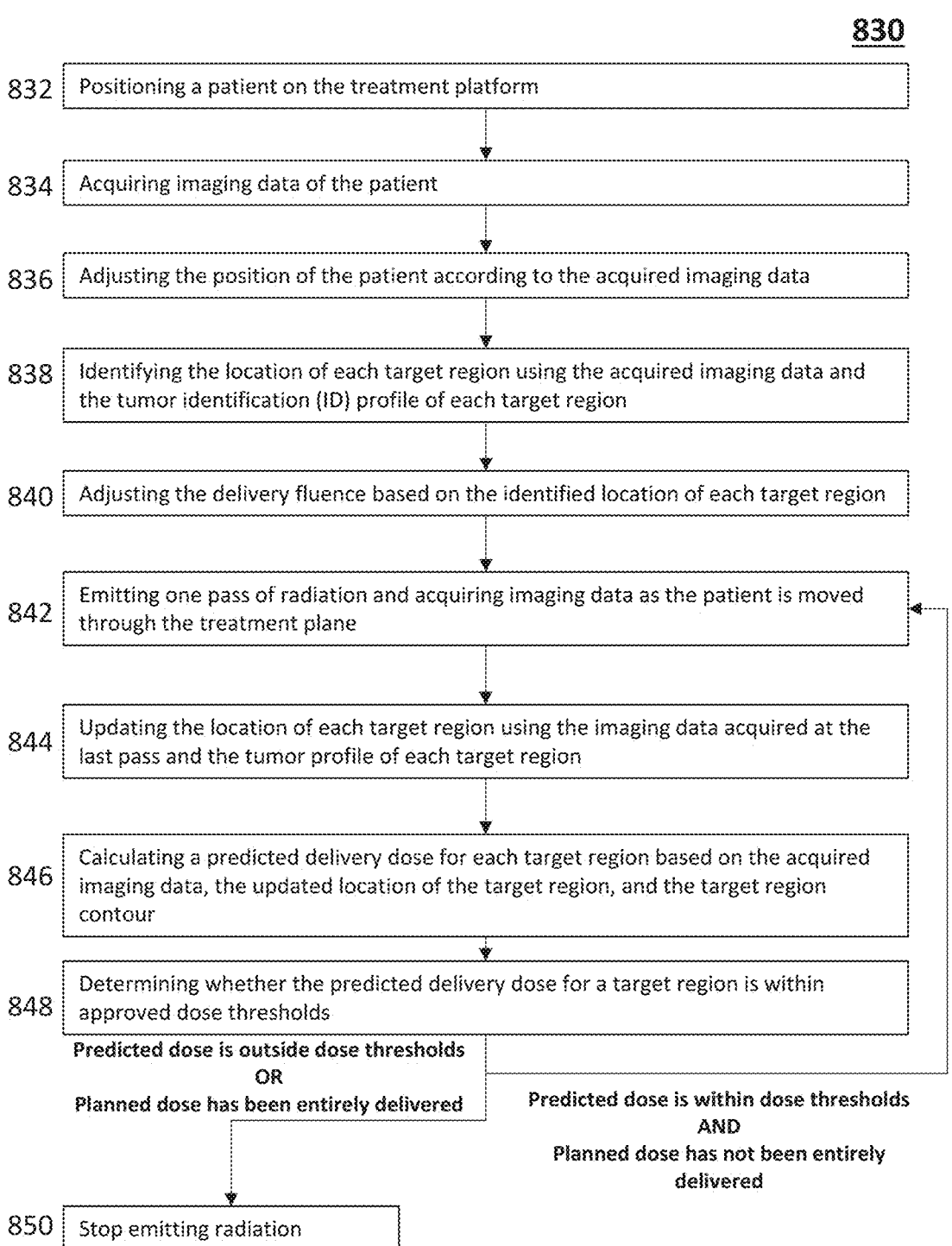
FIG. 8B depicts a flowchart representation of one variation of a workflow that includes in-session safety checks using the tumor ID profile of each target region for BgRT delivery.

FIG. 8B depicts one variation of a workflow that includes in-session safety checks using the tumor ID profile of each target region for BgRT delivery. Method (830) may comprise positioning (832) a patient on the couch or treatment platform, acquiring (834) imaging data of the patient, adjusting (836) the position of the patient according to the acquired imaging data, identifying (838) the location of each target region using the acquired imaging data and the tumor ID profile of each target region, adjusting (840) the delivery fluence based on the identified location of each target region, and emitting (842) one pass of radiation and acquiring imaging data as the patient is moved through the treatment plane. The acquired imaging data may comprise one or more of CT imaging data, MR imaging data, PET imaging data, and the like, and may be limited-time sample and/or may be full images. In some variations, as radiation is delivered to the patient, method (830) may comprise acquiring imaging data, identifying the location(s) of the one or more target regions, calculating the predicted dose to each of the target regions, and determining whether the predicted delivery dose to the one or more target regions is within approved dose thresholds.

After a pass of radiation has been emitted, method (830) may comprise updating (844) the location of each target region using the imaging data acquired at the last pass (and/or cumulative imaging data acquired over one or more shuttle passes) and the tumor profile of each target region, calculating (846) a predicted delivery dose for each target region based on the acquired imaging data, the updated location of the target region, and the target region contour, and determining (848) whether the predicted delivery dose for a target region is within approved dose thresholds. If the predicted dose is outside dose thresholds or the planned dose has been entirely delivered, then radiation emission is stopped (850). Optionally, radiation emission may be stopped if it is determined that the updated location of the target region is no longer within the BTZ (and/or PTV, CTV, GTV). In the scenario where the predicted dose is outside of dose threshold, the radiotherapy system controller may generate a notification to the operator so that they know that treatment has been stopped. The operator may then decide whether to adjust delivery parameters and continue the treatment delivery or to end the treatment session. If the predicted dose is within dose thresholds and the planned dose has not been entirely delivered, method (800) may comprise repeating steps (842-848) until the stopping conditions have been met.

In some variations, method (830) may comprise calculating (846) the predicted delivery dose may comprise calculating an updated delivery fluence using the virtual localization method described above. Virtually localizing each target region after a shuttle pass may allow a delivery fluence to "follow" the updated location of the target region without requiring the operator to enter the radiation bunker to adjust the patient's position. Optionally, method (830) may comprise generating a graphical representation that depicts the predicted delivery dose, a planned delivery dose for the target region(s), and outputting the graphical representation on a display device.

Radiotherapy Systems

Figure 9A:
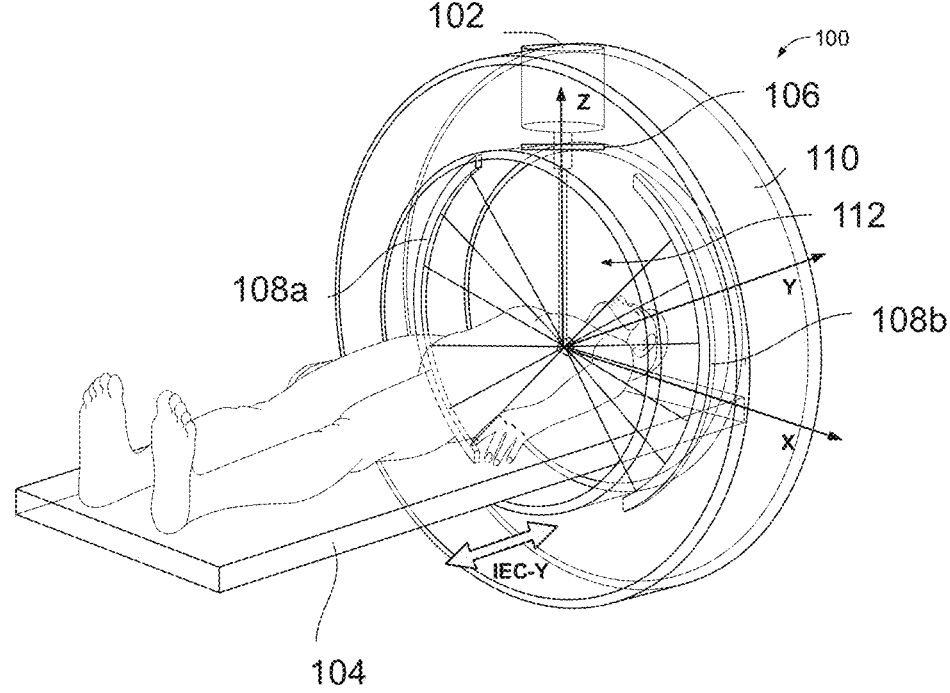
FIG. 9A depicts one variation of a radiotherapy system.

FIG. 9A depicts one variation of a radiotherapy system (100). Radiotherapy system (100) may comprise a gantry (110) rotatable about a patient treatment region (112), a therapeutic radiation source (102) mounted on the gantry, a beam-shaping module (106) disposed in the beam path of the therapeutic radiation source, and a patient platform (119) movable within the patient treatment region (112). Optionally, the radiotherapy system (100) may comprise one or more PET detectors (108) mounted on the gantry. In some variations, the gantry (110) may be a continuously-rotating gantry (e.g., able to rotate through 360° and/or in arcs with an angular spread of less than about 360°). The gantry (110) may be configured to rotate from about 20 RPM to about 70 RPM about the patient treatment region (112). For example, the gantry (110) may be configured to rotate at about 60 RPM. The gantry may also be configured to rotate at a slower rate, e.g., 20 RPM or less, 10 RPM or less, 1 RPM or less. The beam-shaping module (106) may comprise a movable jaw and a dynamic multi-leaf collimator (MLC).

The beam-shaping module may be arranged to provide variable collimation width in the longitudinal direction of 1 cm, 2 cm or 3 cm at the system iso-center (e.g., a center of a patient treatment region). The jaw may be located between the therapeutic radiation source and the MLC, or may be located below the MLC. Alternatively, the beam-shaping module may comprise a split jaw where a first portion of the jaw is located between the therapeutic radiation source and the MLC, and a second portion of the jaw is located below the MLC and coupled to the first portion of the jaw such that both portions move together. The therapeutic radiation source (102) may be configured to emit radiation at predetermined firing positions (e.g., firing angles 0°/360° to) 359° about the patient treatment region (112). For example, in a system with a continuously-rotatable gantry, there may be from about 50 to about 100 firing positions (e.g., 50 firing positions, 60 firing positions, 80 firing positions, 90 firing positions, 100 firing positions, etc.) at various angular positions (e.g., firing angles) along a circle circumscribed by the therapeutic radiation source as it rotates. The firing positions may be evenly distributed such that the angular displacement between each firing position is the same.

Figure 9B:
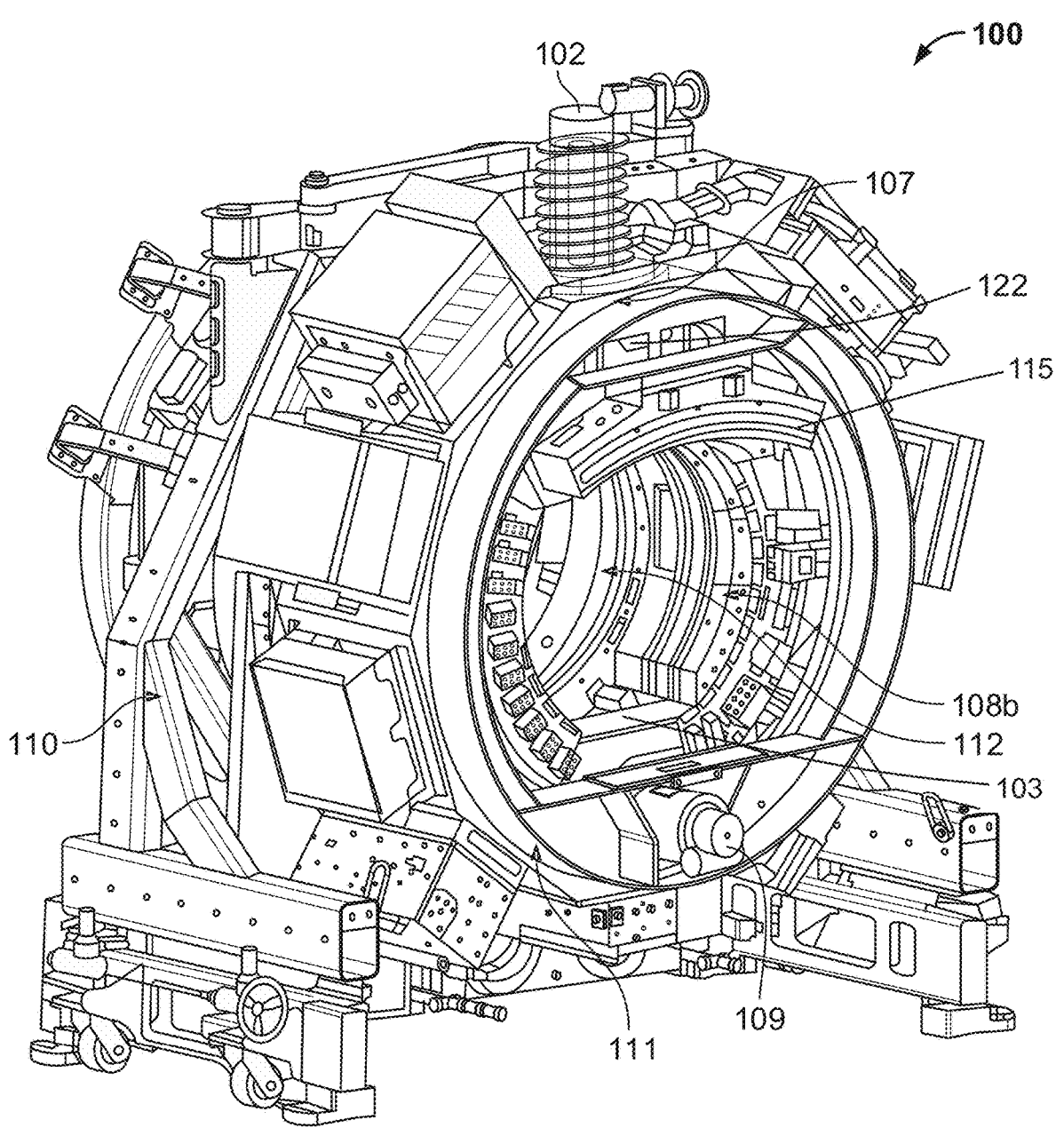
FIG. 9B is a perspective component view of the radiotherapy system of FIG. 9A.

FIG. 9B is a perspective component view of the radiotherapy system (100). As shown there, the beam-shaping module may further comprise a primary collimator or jaw (107) disposed above the binary MLC (122). The radiotherapy system may also comprise an MV X-ray detector (103) located opposite the therapeutic radiation source (102). Optionally, the radiotherapy system (100) may further comprise a kV CT imaging system on a rotatable ring (111) that is attached to the rotatable gantry (110) such that rotating the gantry (110) also rotates the ring (111). The kV CT imaging system may comprise a kV X-ray source (109) and an X-ray detector (115) located across from the X-ray source (109). The therapeutic radiation source or linac (102) and the PET detectors (108) may be mounted on the same cross-sectional plane of the gantry (i.e., PET detectors are co-planar with a treatment plane defined by the linac and the beam-shaping module), while the kV CT scanner and ring may be mounted on a different cross-sectional plane (i.e., not co-planar with the treatment plane). The radiotherapy system (100) of FIGS. 9A and 9B may have a first patient sensor system that comprises the kV CT imaging system and a second patient sensor system that comprises the PET detectors. Optionally, a third patient sensor system may comprise the MV X-ray source and MV detector. The patient sensor data acquired by one or more of these patient sensor systems may include X-ray and/or PET imaging data, and the radiotherapy system controller may be configured to store the acquired patient sensor data and calculate a radiation delivery fluence using the patient sensor data. In some variations, additional patient sensors, such as position sensors, may be included, and the controller may be configured to receive location and/or motion data from the position sensor and incorporate this data with other patient sensor data to calculate a radiation delivery fluence. Additional descriptions of radiotherapy systems that may be used with any of the methods described herein are provided in U.S. Pat. No. 10,695,586, filed Nov. 15, 2017.

The patient platform (104) may be movable in the treatment region (112) to discrete, pre-determined locations along IEC-Y. These discrete, pre-determined locations may be referred to as "beam stations". For example, a radiotherapy treatment planning system may specify 200 beam stations, where each beam station is about 2 mm (e.g., 2.1 mm) apart from its adjacent beam stations. During a treatment session, the radiotherapy treatment system may move the patient platform to each of the beam stations, and may stop the platform at a beam station while radiation is delivered to the patient. In some variations, after the platform has been stepped to each of the 200 beam stations in a first direction (e.g., into the bore), the platform may be stepped to each of the 200 beam stations in a second direction opposite the first direction (e.g., out of the bore, in reverse), where radiation is delivered to the patient while the platform is stopped at a beam station. Alternatively, or additionally, after the platform has been stepped to each of the 200 beam stations in a first direction (e.g., into the bore) where radiation is delivered at each of the beam stations, the platform may be moved in reverse so that it returns to the first beam station. No radiation may be delivered while the platform is moved back to the first beam station. The platform may then be stepped, for a second time, to each of the 200 beam stations in the first direction for a second pass of radiation delivery. In some variations, the platform may be moved continuously while radiation is delivered to the patient and may not be stopped at beam stations during the delivery of therapeutic radiation. Additional descriptions of patient platforms that may be used with any of the radiotherapy systems and methods described herein are provided in U.S. Pat. No. 10,702,715, filed Nov. 15, 2017.

Figure 9C:
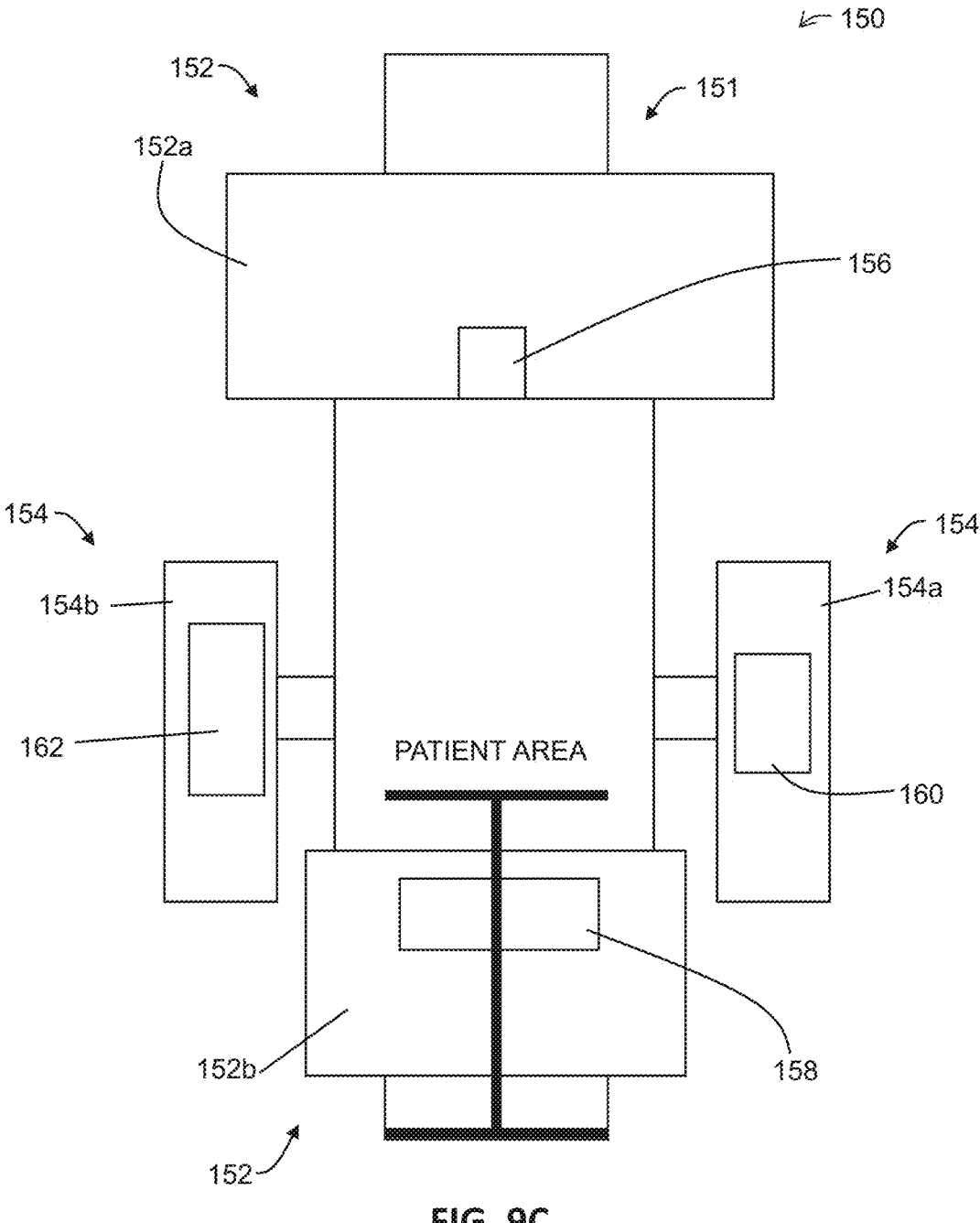
FIG. 9C depicts another variation of a radiotherapy system.

FIG. 9C depicts another variation of a radiotherapy system (150) that may be used to deliver radiation in accordance with any of the methods described herein. The radiotherapy system (150) may have the components of the radiotherapy system represented in the block diagram of FIG. 1. Radiotherapy system (150) may comprise a gantry or support structure (151) comprising a first pair of arms (152) rotatable about a patient area and a second pair of arms (154) rotatable about the patient area, an imaging system comprising a therapeutic radiation system comprising an MV radiation source (156) mounted on a first arm (152a) of the first pair of arms (152) and an MV detector (158) mounted on a second arm (152b) of the first pair of arms (152), and a kV radiation source (160) mounted on a first arm (154a) of the second pair of arms (154) and a kV detector (162) mounted on a second arm (154b) of the second pair of arms (154). The first and second arms of the first pair of arms (152) may be located opposite each other (e.g., on opposite sides of the patient area, across from each other, and/or about 180 degrees from each other), such that the MV radiation source (156) and the MV detector (158) are located opposite each other (e.g., the MV detector is located in the beam path of the MV radiation source). The first and second arms of the second pair of arms (154) may be located opposite each other (e.g., on opposite sides of the patient area, across from each other, and/or about 180 degrees from each other), such that the kV radiation source (160) and the kV detector (162) are located opposite each other (e.g., the kV detector is located in the beam path of the kV radiation source). The radiotherapy system controller may be configured to store acquired imaging data (from either or both the kV detector and the MV detector) and calculate a radiation delivery fluence. Optionally, one or more target region surrogate devices, such as a breathing sensor, may be included, and the controller may be configured to receive location and/or motion data from the target region surrogate to calculate a radiation delivery fluence.

The MV radiation source (156) (i.e., the therapeutic radiation source) may be configured to emit radiation at predetermined firing positions about the patient area. In some variations where the MV radiation source is moved around the patient area along a single plane, the firing positions may be referred to as firing angles, which may be from 0°/360° to 359°. Alternatively or additionally, the gantry and/or support structure arms may be configured to move the MV radiation source to a firing position at any coordinate(s) in 3-D space, i.e., as designated by coordinates (x,y,z). For example, the gantry arms (152, 154) may be robotic arms having articulated joints and/or one or more gimbals that may be configured to position and/or orient the MV radiation source at any desired firing position. The gantry or support structure may be configured to continuously move MV radiation source through the firing positions or may be configured to step the MV radiation source to each firing position (i.e., move the MV radiation source to a firing position and remain stationary at that firing position). Alternatively, or additionally, the MV radiation source may be configured to emit radiation only at the predetermined firing positions or may be configured to emit radiation continuously, even as it is being moved from one firing position to the next.

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments/variations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for locating a target region, the method comprising:
   acquiring imaging data of a patient region that includes a tumor;
   generating a map of pixel tumor likelihood values by calculating a tumor-likelihood value and background-likelihood value for each pixel of the imaging data; and
   determining a location of the tumor by shifting a tumor contour within the imaging data to a centroid location of the map of pixel tumor likelihood values within a BTZ contour, wherein the BTZ contour encompasses the tumor contour.

2. The method of claim 1, wherein determining the location of the tumor further comprises:
   iteratively updating the map of pixel tumor likelihood values to generate a final map of pixel tumor likelihood values such that an average pixel value within the shifted tumor contour is within a previously-defined threshold of an average pixel value within a pre-shifted tumor contour;

calculating a centroid location of the final map of pixel tumor likelihood values; and determining the location of the tumor by shifting the tumor contour to the calculated centroid location.

3. The method of claim 2, wherein generating a map of pixel tumor likelihood values comprises calculating a tumor-likelihood value and background-likelihood value for each pixel in the acquired imaging data.

4. The method of claim 3, wherein calculating a tumor-likelihood value comprises calculating an average pixel value over the pixels within the tumor contour and a standard deviation value of the pixel values within the tumor contour.

5. The method of claim 4, wherein calculating a background-likelihood value comprises calculating an average pixel value over the pixels outside the tumor contour and within the BTZ contour and a standard deviation value of the pixel values outside the tumor contour and within the BTZ contour.

6. The method of claim 5, wherein iteratively updating the map of pixel tumor likelihood values comprises:

updating the map of pixel tumor probability values by assigning pixels within the shifted tumor contour a high tumor-probability value and assigning pixels outside the shifted tumor contour a low tumor-probability value;

updating tumor-likelihood values and background-likelihood values for each pixel in the acquired imaging data; and adjusting the map of pixel tumor likelihood values using the updated map of pixel tumor probability values, updated tumor-likelihood values, and background-likelihood values.

7. The method of claim 2, further comprising generating a graphical representation that comprises the tumor contour that has been shifted to the centroid location of the final map of pixel tumor likelihood values, the acquired updated imaging data and displaying the graphical representation to a display device.

8. The method of claim 1, further comprising generating an initial map of pixel tumor probability values based on an initial image of the tumor, wherein the pixel tumor probability values are binary values and pixel likelihood values are any values greater than or equal to zero and less than or equal to one.

9. The method of claim 1, wherein the acquired imaging data of the tumor comprises one or more of PET imaging data, CT imaging data, MR imaging data, and X-ray imaging data.

10. The method of claim 1, further comprising generating an initial map of pixel tumor probability values based on an initial image of the tumor by assigning pixels within the tumor contour a high tumor-probability value and assigning pixels outside the tumor contour a low tumor-probability value.

11. The method of claim 10, wherein the high tumor-probability value is one and the low tumor-probability value is zero.

12. The method of claim 1, wherein acquiring imaging data comprises acquiring PET imaging data.

13. The method of claim 1, wherein acquiring imaging data comprises acquiring CT imaging data.

14. The method of claim 1, wherein acquiring imaging data comprises acquiring MR imaging data.

15. The method of claim 1, wherein acquiring imaging data comprises acquiring SPECT imaging data.

16. The method of claim 1, further comprising generating a graphical representation that comprises the tumor contour that has been shifted to the location of the tumor and displaying the graphical representation to a display device.

17. The method of claim 16, wherein the graphical representation further comprises the BTZ contour, and wherein the shifted tumor contour and BTZ contour are superimposed on the acquired imaging data.

18. The method of claim 1, further comprising generating a notification if a proximity of the shifted tumor contour to the BTZ contour is within a pre-determined margin.

19. A method for evaluating a PET signal for radiotherapy, the method comprising:

acquiring PET imaging data of a patient region that includes a biology targeting zone (BTZ) region and a target region within the BTZ region;

determining a location of the target region within the BTZ region based on the PET imaging data;

calculating a target region standard uptake value (SUV) for pixels of the PET imaging data within the target region;

calculating a BTZ region SUV for pixels of the PET imaging data outside the target region and within the BTZ region;

calculating a normalized PET signal metric value of the target region using the target region SUV and the BTZ region SUV; and evaluating the PET imaging data by comparing the normalized PET signal metric value with a planning PET signal metric value.

20. The method of claim 19, wherein comparing the normalized PET signal metric value with a planning PET signal metric value comprises calculating a predicted radiation dose for the target region based on the net PET signal metric value and comparing the predicted radiation dose with a prescribed radiation dose.

21. The method of claim 19, wherein determining the location of the target region comprises:

generating a map of pixel tumor likelihood values by calculating a tumor- likelihood value and background-likelihood value for each pixel of the PET imaging data;

shifting a contour of the target region to a centroid location of the map of pixel tumor likelihood values;

iteratively updating the map of pixel tumor likelihood values to generate a final map of pixel tumor likelihood values such that an average pixel value within the shifted target region contour is within a previously-defined threshold of an average pixel value within a pre-shifted tumor contour;

calculating a centroid location of the final map of pixel tumor likelihood values; and determining the target region location by shifting the target region contour to the calculated centroid location.

22. A method of tracking a target region, the method comprising:

acquiring PET imaging data of a target region;

identifying, using the acquired PET imaging data and a tumor identification (ID) profile, a location of the target region;

determining whether the location of the target region is within a target region contour; and generating a notification if the location of the target region is outside a target region contour.

23. The method of claim 22, wherein the target region contour is a biology-tracking zone (BTZ) contour.

24. The method of claim 22, wherein the target region contour is a planning target volume (PTV) contour.

25. The method of claim 22, further comprising generating an interlock to stop radiation delivery if the location of the target region is outside the target region contour.

26. The method of claim 22, wherein determining whether the location of the target region is within a target region contour comprises determining whether any portion of the target region is outside the target region contour, and the method further comprises generating an interlock to stop radiation delivery if any portion of the target region is outside the target region contour.

27. The method of claim 22, wherein the notification is a graphical user interface that comprises the location of the target region and the target region contour, and the method further comprises outputting the graphical user interface to a display device.

28. The method of claim 22, wherein the notification is an audible alert, and the method further comprises outputting the audible alert to a speaker device.

29. A method of tracking a target region, the method comprising:

acquiring PET imaging data of a target region;

identifying, using the acquired PET imaging data, a location of the target region, and wherein identifying the location of the target region comprises generating a map of pixel tumor likelihood values by calculating a tumor-likelihood value and background-likelihood value for each pixel of the PET imaging data and identifying the location of the target region by shifting a tumor contour within the PET imaging data to a centroid location of the map of pixel tumor likelihood values;

determining whether the location of the target region is within a target region contour; and generating a notification if the location of the target region is outside a target region contour.

* * * * *